(12) United States Patent
Song et al.

(10) Patent No.: US 11,426,073 B2
(45) Date of Patent: Aug. 30, 2022

(54) IMAGING NERVE FUNCTION AND PATHOLOGIES USING DIFFUSION BASIS SPECTRUM IMAGING

(71) Applicants: Sheng-Kwei Song, St. Louis, MO (US); William M. Spees, St. Louis, MO (US); Tsen-Hsuan Lin, St. Louis, MO (US); Peng Sun, St. Louis, MO (US); Chunyu Song, St. Louis, MO (US)

(72) Inventors: Sheng-Kwei Song, St. Louis, MO (US); William M. Spees, St. Louis, MO (US); Tsen-Hsuan Lin, St. Louis, MO (US); Peng Sun, St. Louis, MO (US); Chunyu Song, St. Louis, MO (US)

(73) Assignee: Washington University, St. Louis, MO (US)

( * ) Notice: Subject to any disclaimer, the term of this patent is extended or adjusted under 35 U.S.C. 154(b) by 359 days.

(21) Appl. No.: 16/398,053

(22) Filed: Apr. 29, 2019

(65) Prior Publication Data
US 2019/0328231 A1 Oct. 31, 2019

Related U.S. Application Data

(60) Provisional application No. 62/663,816, filed on Apr. 27, 2018.

(51) Int. Cl.
*A61B 5/00* (2006.01)
*A61B 5/055* (2006.01)
(Continued)

(52) U.S. Cl.
CPC ............ *A61B 5/0042* (2013.01); *A61B 5/055* (2013.01); *A61B 5/742* (2013.01); *G01R 33/5608* (2013.01); *G01R 33/56341* (2013.01)

(58) Field of Classification Search
CPC ......... A61B 5/0042; A61B 5/055; A61B 5/24; A61B 5/4041; A61B 5/742; G01R 33/4806; G01R 33/5608; G01R 33/56341
See application file for complete search history.

(56) References Cited

U.S. PATENT DOCUMENTS

2011/0218253 A1\* 9/2011 Lange .................... A61K 45/00
514/789
2012/0271148 A1\* 10/2012 Nelson ............... A61N 1/36139
600/411

(Continued)

FOREIGN PATENT DOCUMENTS

WO WO-2017190029 A1 \* 11/2017 ............. A61B 5/055

OTHER PUBLICATIONS

M. Kubicki et al. Decreased axial diffusivity within language connections: A possible biomarker of schizophrenia risk Jun. 22, 2013 Schizophrenia Research, 148, pp. 67-73 (Year: 2013).\*

(Continued)

*Primary Examiner* — Oommen Jacob
*Assistant Examiner* — Maria Christina Talty
(74) *Attorney, Agent, or Firm* — Armstrong Teasdale LLP

(57) ABSTRACT

Repetitive electrical activity produces microstructural alteration in myelinated axons. These transient microstructural changes can be non-invasively visualized via two different magnetic-resonance-based approaches: diffusion fMRI and dynamic $T_2$ spectroscopy in the ex vivo perfused bullfrog sciatic nerves. Non-invasive diffusion fMRI, based on standard diffusion tensor imaging (DTI), clearly localized the sites of axonal conduction blockage as might be encountered in neurotrauma or other lesion types. Diffusion fMRI response was graded in proportion to the total number of electrical impulses carried through a given locus. Diffusion basis spectrum imaging (DBSI) method revealed a reversible shift of tissue water into a restricted isotropic diffusion (Continued)

signal component, consistent with sub-myelinic vacuole formation.

11 Claims, 45 Drawing Sheets
(23 of 45 Drawing Sheet(s) Filed in Color)

(51) Int. Cl.
    *G01R 33/56*     (2006.01)
    *G01R 33/563*     (2006.01)

(56) References Cited

U.S. PATENT DOCUMENTS

2012/0280686 A1* 11/2012 White .............. G01R 33/56341
    324/309
2016/0022207 A1* 1/2016 Roberts ................ A61B 5/4848
    600/409
2018/0049665 A1* 2/2018 Jeong ..................... A61B 5/055

OTHER PUBLICATIONS

Robert Lindenberg, Lin L. Zhu, Theodor Ruber, Gottfriend Schlaug Predicting Functional Motor Potential in Chronic Stroke Patients Using Diffusion Tensor Imaging Apr. 29, 2011 Human Brain Mapping, 33, pp. 1040-1051 (Year: 2011).*

Rajesh Kumar et al. Regional Brain Axial and Radial Diffusivity Changes During Development 2012 Journal of Neuroscience Research, 90, pp. 346-355 (Year: 2012).*

Nader S. Metwalli et al. Utility of axial and radial diffusivity from diffusion tensor MRI as markers of neurodegeneration in amyotrophic lateral sclerosis Jun. 1, 2010 Brain Research, 1348, pp. 156-164 (Year: 2010).*

Toshihiko Aso et al., "An intrinsic diffusion response function for analyzing diffusion functional MRI time series," May 18, 2009, NeuroImage, 47, pp. 1487-1495 (Year: 2009).*

Basser, P.J. et al. "Estimation of the Effective Self-Diffusion Tensor from the NMR Spin Echo," Journal of Magnetic Resonance, Series B., 103(3): 247-254 (1994).

Beaulieu, C. et al. "Multicomponent Water Proton Transverse Relaxation and T2-Discriminated Water Diffusion in Myelinated and Nonmyelinated Nerve," Magnetic Resonance Imaging 16(10): 1201-1210 (1998).

Bengtsson, S.L. et al. "Extensive piano practicing has regionally specific effects on white matter development," Nature Neuroscience 8(9): 1148-1150 (2005).

Chiang, C-W. et al. "Quantifying white matter tract diffusion parameters in the presence of increased extra-fiber cellularity and vasogenic edema," NeuroImage 101: 310-319 (2014).

Demerens, C. et al. "Induction of myelination in the central nervous system by electrical activity," Proceedings of the National Academy of Sciences USA 93: 9887-9892 (1996).

Does, M.D. et al. "T2 Relaxation of Peripheral Nerve Measured In Vivo," Magnetic Resonance Imaging 13(4): 575-580 (1995).

Gibson, E.M. et al. "Neuronal Activity Promotes Oligodendrogenesis and Adaptive Myelination in the Mammalian Brain," Science 344(1252304): 1-12 (2014).

Ishibashi, T. et al. "Astrocytes Promote Myelination in Response to Electrical Impulses," Neuron 49(6): 823-832 (2006).

Lin, T-H. et al. "Diffusion fMRI detects white-matter dysfunction in mice with acute optic neuritis," Neurobiology of Disease 67: 1-8 (2014).

Mandl, R.C.W. et al. "Functional diffusion tensor imaging: measuring task-related anisotropy changes in the human brain along white matter tracts," PLoS One 3(11): e3631 (10 pages) (2008).

Scholz, J. et al. "Training induces changes in white-matter architecture," Nature Neuroscience 12(11): 1370-1371 (2009).

Spees, W.M. et al., "White-matter diffusion fMRI of mouse optic nerve," NeuroImage 65: 209-215 (2013).

Vasilescu, V. et al., "Water compartments in the myelinated nerve. III. Pulsed NMR result," Experientia 34(11): 1443-1444 (1978).

Wachowicz, K., et al. "Assignment of the T2 Components of Amphibian Peripheral Nerve to Their Microanatomical Compartments," Magnetic Resonance in Medicine 47(2): 239-245 (2002).

Wang Y., et al. "Quantification of increased cellularity during inflammatory demyelination," Brain 134(12): 3590-3601 (2011).

* cited by examiner

T1W

Reduced-FOV DWI

DBSI: 39% vs. baseline (average of three slices)
DTI: 12% vs. baseline (average of three slices)

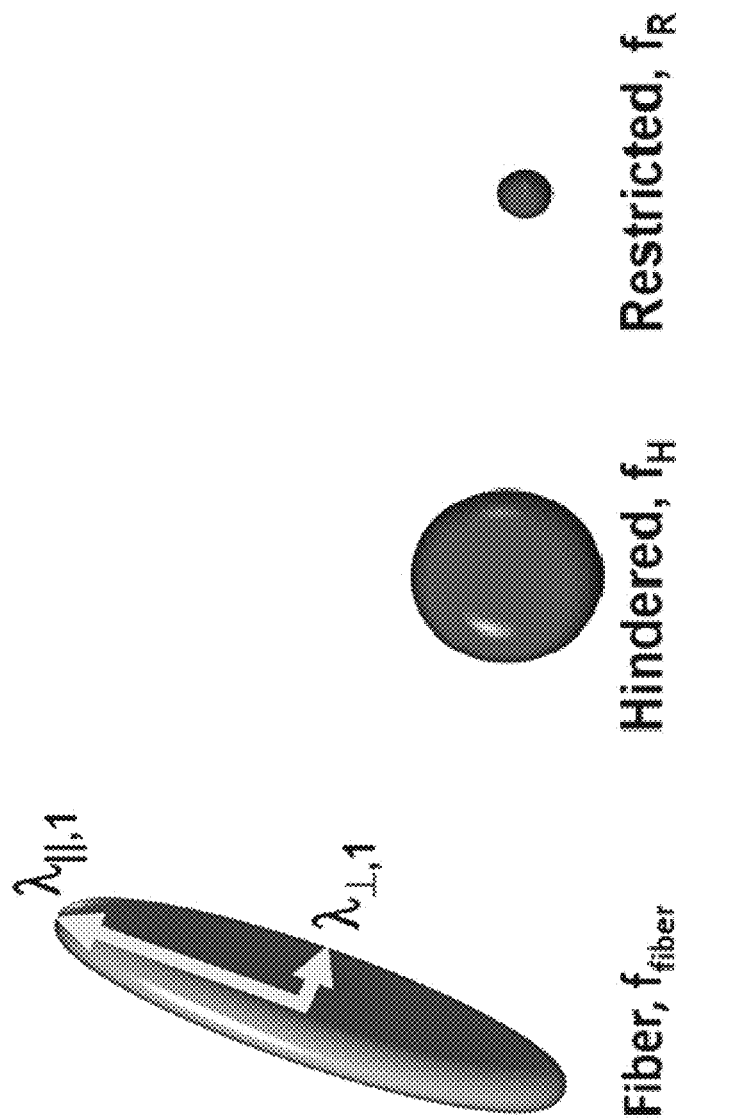

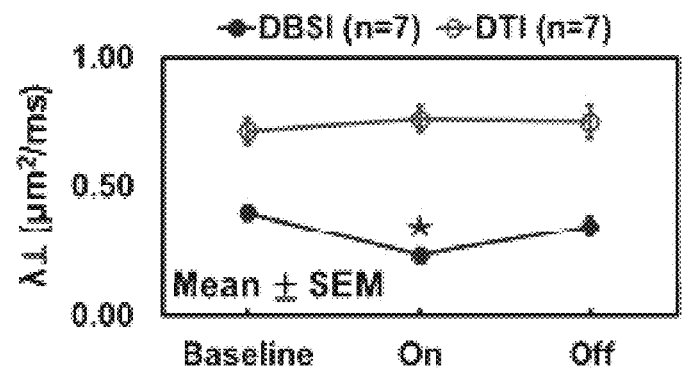
FIG. 18A
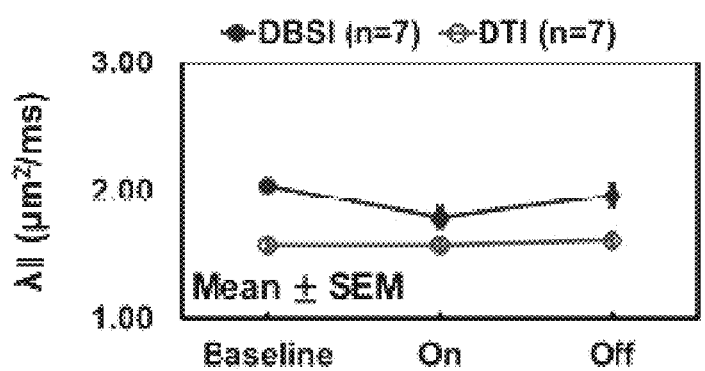
FIG. 18B
| | Baseline | On | Off |
|---|---|---|---|
| DBSI $\lambda_\perp$ | 0.40 ± 0.03 | 0.23 ± 0.02 | 0.34 ± 0.04 |
| DTI $\lambda_\perp$ | 0.7' ± 0.05 | 0.75 ± 0.05 | 0.74 ± 0.06 |
| DBSI $\lambda_\parallel$ | 2.04 ± 0.04 | 1.78 ± 0.08 | 1.96 ± 0.05 |
| DTI $\lambda_\parallel$ | 1.57 ± 0.04 | 1.57 ± 0.04 | 1.60 ± 0.05 |
FIG. 18C

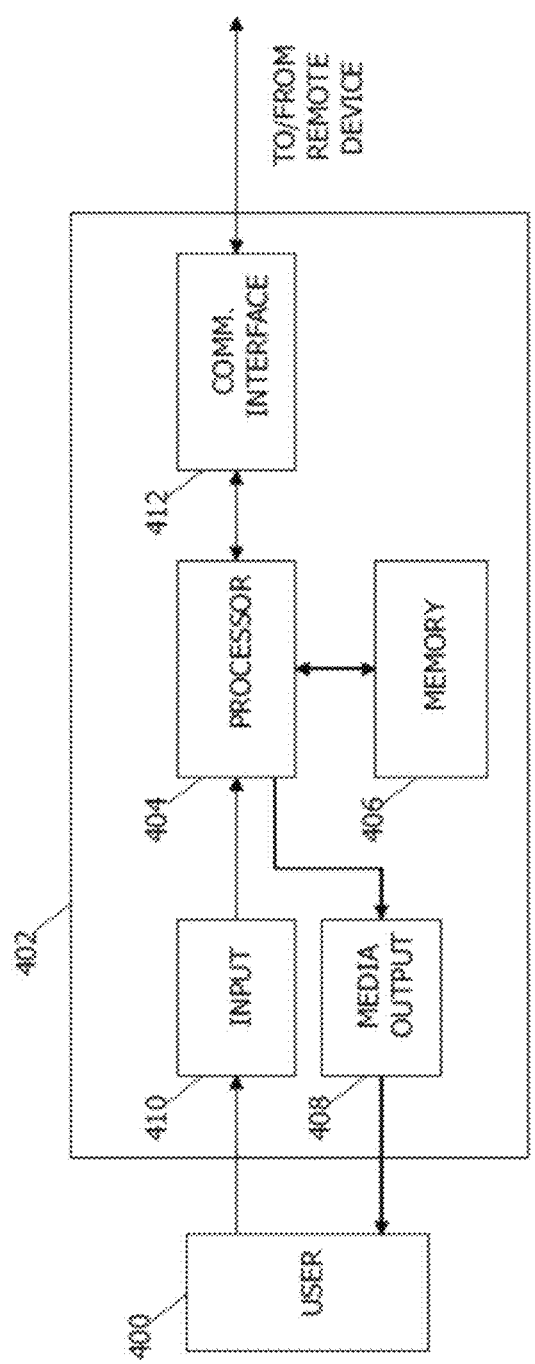

IMAGING NERVE FUNCTION AND PATHOLOGIES USING DIFFUSION BASIS SPECTRUM IMAGING

CROSS-REFERENCE TO RELATED APPLICATION

This application claims the benefit of priority to U.S. Provisional Application No. 62/663,816, filed Apr. 27, 2018, which is hereby incorporated by reference herein in its entirety.

STATEMENT OF GOVERNMENTAL SUPPORT

This invention was made with government support under grants U01EY025500, R01NS047592, and P01NS059560 awarded by the National Institutes of Health. The government has certain rights in the invention.

BACKGROUND

BOLD functional MRI has been extremely successful and forms the basis of the NIH-supported Human Connectome Project. Despite the continued success of resting-state and task-specific fMRI applications, few have demonstrated the ability to image nerve activation using BOLD fMRI. Diffusion-weighted MRI has recently been proposed to image brain function as those seen by BOLD fMRI, without a consensus in its utility or mechanisms.

Blood oxygen-level-dependent functional magnetic resonance imaging (BOLD fMRI) has revolutionized our ability to study human brain function. Because grey matter is relatively well-vascularized, the BOLD effect works exceptionally well as a means to indirectly monitor neuronal activity. By comparison, successful studies with white matter (WM) BOLD fMRI are limited because both blood volume and the tissue's capacity for physiologic modulation of blood flow are considerably less than in grey matter.

Diffusion Tensor Imaging (DTI) has been employed extensively to investigate WM structure. DTI models random thermal displacement of water as a single tensor, which can be used to encapsulate the direction-dependent behavior of water diffusion, reflecting fiber orientations in ordered tissues. Using DTI, it has been demonstrated that prolonged periods (weeks, months, years) of training activities, such as piano playing or juggling, result in detectable changes of the diffusion MRI properties of the requisite WM pathways. Presumably, the diffusion MRI changes are due to increased myelination of the chronically electrically-active axons in the WM tracts used in these coordinated behaviors.

White matter comprises approximately 50% of the volume of the human brain, and various pathologies (e.g., multiple sclerosis) directly target WM and lead to disability. Thus, non-invasive assessment of WM function, including pinpointing lesions that block conduction of action potentials, could conceivably be very powerful for understanding disease progression and monitoring therapeutic response.

White matter diffusion fMRI investigations have applied DTI, or variants thereof, to monitor short-term structural alterations with WM electrical activity. For example, functional DTI was performed to measure task-related changes in fractional anisotropy (FA) along the thalamocortical tract and optic radiation upon tactile and visual stimulation, respectively. Additional previous studies have used ion-sensitive electrodes to monitor the concentration of the tetramethylammonium ion in the extracellular space of perfused rat optic nerves, and reported a reversible decrease in the volume of the extracellular space in WM tissue with repetitive electrical stimulation.

These studies motivated an in vivo WM diffusion fMRI study, wherein we demonstrated that in healthy mice, a flashing-light visual stimulus led to a reversible decrease in the apparent diffusion coefficient of water perpendicular to the optic nerve fibers ($ADC_\perp$, also denoted as $\lambda_\perp$) of the stimulated eye. Diffusion changes were absent in the optic nerve of the contralateral, non-stimulated eye. Moreover, the $ADC_\perp$ decrease was found to be attenuated in mice with acute optic neuritis, the magnitude of the WM diffusion fMRI response being correlated with visual acuity in the affected eye As an extension of DTI, Diffusion Basis Spectrum Imaging (DBSI) models the tissue water diffusion signal as one or more discrete anisotropic tensors (reflecting one or more fiber components) and a spectrum of isotropic diffusion tensors. A pictorial overview of this model is presented in FIG. 4. Diffusion basis spectrum imaging (DBSI) signal modeling represents the diffusion-attenuated signal, measured along 25-directions and multiple diffusion-weightings (b values), as a sum of one or more anisotropic diffusion tensors and a spectrum of isotropic diffusivities (D). The overall diffusion signal can be decomposed into fiber fraction(s), and isotropic diffusion spectral components. In the disclosed method, the restricted component ($f_R$) has $D \leq 0.3$ $\mu m^2/ms$, the hindered diffusion component ($f_H$) falls in the range, $0.3 < D < 2.0$ $\mu m^2/ms$, and the free diffusion component ($f_{free}$) accounts for $D \geq 2.0$ $\mu m^2/ms$.

The isotropic diffusion spectrum can reflect more complex features of the diffusion MRI signal and tissue pathology/structure. The isotropic diffusion spectrum is typically divided into a restricted component (the lowest range of isotropic diffusion coefficients, which can reflect variation in tissue cellularity occurring with inflammation or cancer), a hindered component (the intermediate band of the isotropic diffusion spectrum, which may be elevated in vascular edema or axonal loss), and a free diffusion component (for example, when partial volume effects lead to inclusion of cerebrospinal fluid in an imaging voxel's total signal). Further details of the tissue microstructural alterations in electrically-active myelinated axons are observable with DBSI—details that are not accessible in a DTI analysis of the diffusion fMRI data.

BRIEF SUMMARY

In one aspect, a computer-implemented method of detecting nerve activity from a time series of diffusion MRI images is provided. The method includes obtaining, using an MRI scanner, a time-series of diffusion MRI datasets from a nerve. Each diffusion MRI dataset includes a plurality of voxels and associated diffusion MRI signals. The method further includes applying, using a computing device, a diffusion basis spectrum imaging (DBSI) model to each diffusion MRI dataset of the time-series to obtain a time-series of at least one DBSI parameter. The method further includes detecting, using the computing device, the nerve activity at each voxel of the plurality of voxels based on changes in at least one value within the time series of the at least one DBSI parameter according to a nerve activity detection rule. The method further includes transforming, using the computing device, the detected nerve activity into a spatial map of nerve activity at each voxel position of the diffusion MRI dataset, and displaying to a user, using a display device operatively coupled to the computing device, the spatial map of nerve activity. The nerve activity detection rule further includes detecting a nerve activity for at least one of: an increase of a fiber component ($f_{fiber}$) value above a first threshold value; an increase of a restricted component ($f_R$) value above a second threshold value; a decrease of an axial diffusivity ($\lambda_\parallel$) value below a third threshold value; a decrease of a radial diffusivity ($\lambda_\perp$) value below a fourth threshold value; a decrease of a hindered isotropic spectral component ($D_H$) value below a fifth threshold value; and an increase of a restricted isotropic spectral component ($D_R$) value above a sixth threshold value. In one aspect, the first threshold value is 1% of a total diffusion signal higher than a baseline $f_{fiber}$ value associated with a non-stimulated nerve; the second threshold value is about 0.3% of the total diffusion signal higher than a baseline $f_R$ value associated with a non-stimulated nerve; the third threshold value is about 0.06 $\mu m^2/ms$ less than a baseline $\lambda_\parallel$ value associated with a non-stimulated nerve; the fourth threshold value is about 0.02 $\mu m^2/ms$ less than a baseline $f_R$ value associated with a non-stimulated nerve; the fifth threshold value is about 0.1% $\mu m^2/ms$ less than a baseline $D_H$ value associated with a non-stimulated nerve; and the sixth threshold value is about 0.03 $\mu m^2/ms$ less than a baseline $D_R$ value associated with a non-stimulated nerve. In another aspect, the method may further include estimating, using the computing device, an intensity of nerve activation based on changes in at least one value within the time series of the at least one DBSI parameter according to a nerve activity intensity rule. The nerve activity intensity rule includes an empirically-derived relationship between a change in the axial diffusivity ($\lambda_\parallel$) value and a nerve activity intensity, wherein further increases of axial diffusivity ($\lambda_\parallel$) value below the third threshold value are indicative of increased nerve activity intensity.

In an additional aspect, a computer-implemented method of detecting optic nerve activity in a human subject from a time series of diffusion MRI images is disclosed that includes obtaining, using an MRI scanner, a time-series of diffusion MRI datasets from an optic nerve. Each diffusion MRI dataset includes a plurality of voxels and associated diffusion MRI signals. The method also includes applying, using a computing device, a diffusion basis spectrum imaging (DBSI) model to each diffusion MRI dataset of the time-series to obtain a time-series of at least one DBSI parameter. The method further includes detecting, using the computing device, the nerve activity at each voxel of the plurality of voxels based on changes in at least one value within the time series of the at least one DBSI parameter according to a nerve activity detection rule. The method also includes transforming, using the computing device, the detected nerve activity into a spatial map of nerve activity at each voxel position of the diffusion MRI dataset, and displaying to a user, using a display device operatively coupled to the computing device, the spatial map of nerve activity. In another aspect, the nerve activity detection rule includes detecting a nerve activity for at least one of: a decrease of an axial diffusivity ($\lambda_\parallel$) value below a third threshold value; and a decrease of a radial diffusivity ($\lambda_\perp$) value below a fourth threshold value. In an additional aspect, the third threshold value is about 0.2 $\mu m^2/ms$ less than a baseline $\lambda_\parallel$ value associated with a non-stimulated nerve; and the fourth threshold value is about 0.3 $\mu m^2/ms$ less than a baseline $\lambda_\perp$ value associated with a non-stimulated nerve.

In yet another aspect, a computer-implemented method of detecting optic nerve pathology in a human subject from a time series of diffusion MRI images. The method includes obtaining, using an MRI scanner, a diffusion MRI dataset from an optic nerve, the diffusion MRI dataset comprising a plurality of voxels and associated diffusion MRI signals. The method further includes applying, using a computing device, a diffusion basis spectrum imaging (DBSI) model to the diffusion MRI dataset to obtain at least one DBSI parameter. The method also includes detecting, using the computing device, the optic nerve pathology at each voxel of the plurality of voxels based on at least one value of the at least one DBSI parameter according to a optic nerve pathology detection rule. The method also includes transforming, using the computing device, the detected optic nerve pathology into a spatial map of optic nerve pathology at each voxel position of the diffusion MRI dataset, and displaying to a user, using a display device operatively coupled to the computing device, the spatial map of optic nerve pathology. In another aspect, the optic nerve pathology detection rule includes detecting an optic nerve pathology for at least one of: a decrease of an axial diffusivity ($\lambda_\parallel$) value below a third threshold value; and an increase of a radial diffusivity ($\lambda_\perp$) value above a fourth threshold value. In another aspect, the third threshold value is about 0.5 $\mu m^2/ms$ less than a baseline $\lambda_\parallel$ value associated with a non-stimulated nerve; and the fourth threshold value is about 0.1 $\mu m^2/ms$ greater than a baseline $\lambda_\perp$ value associated with a non-stimulated nerve.

BRIEF DESCRIPTION OF FIGURES

The patent or application file contains at least one drawing executed in color. Copies of this patent or patent application publication with color drawing(s) will be provided by the Office upon request and payment of the necessary fee.

FIG. 7A is a schematic illustration of the DBSI diffusion components;

FIG. 18A is a graph comparing the mean $\lambda_\perp$ obtained from the optic nerve of a living human subject before, during, and after exposure to a visual stimulus using DBSI and DTI;

FIG. 18B is a graph comparing the mean $\lambda_\parallel$ obtained from the optic nerve of a living human subject before, during, and after exposure to a visual stimulus using DBSI and DTI;

FIG. 18C is a table summarizing the $\lambda_\perp$ and $\lambda_\parallel$ values shown in the graphs of FIGS. 18A and 18B;

FIG. 28 is a block diagram of an example computing device.

Figure 1A:
FIG. 1A is an image showing a T1-weighted MRI image of a human patient with a region containing optic nerve tracts identified within an overlaid yellow rectangle.

Advantages will become more apparent to those skilled in the art from the following description of the preferred aspects which have been shown and described by way of illustration. As will be realized, the present aspects may be capable of other and different aspects, and their details are capable of modification in various respects. Accordingly, the drawings and description are to be regarded as illustrative in nature and not as restrictive.

DETAILED DESCRIPTION

In various aspects, systems and methods for monitoring electrical activity of myelinated axons using diffusion basis spectrum imaging (DBSI) are disclosed herein. Without being limited to any particular theory, repetitive electrical activity produces microstructural alteration in myelinated axons, which enables noninvasively monitoring of the function of myelinated fibers in peripheral nervous system (PNS)/CNS pathways. In various aspects, microstructural changes in myelinated axons resulting from repetitive electrical activity are assessed using noninvasive diffusion basis spectrum imaging (DBSI) analysis of diffusion functional MRI data. In one aspect, a reversible shift of tissue water into a restricted isotropic diffusion signal component is observed in myelinated axons after exposure to repetitive stimulation. As described in various examples below, this reversible shift of tissue water into the restricted isotropic diffusion signal component is thought to result from the formation of submyelinic vacuoles observed in electron-microscopy images of tissue fixed during electrical stimulation. In various aspects, the disclosed method uses correlations between electrophysiology and DBSI parameters during and immediately after stimulation to determine the electrical activity of myelinated axons non-invasively.

BOLD fMRI has proven to be extremely powerful for studying brain function, but is essentially limited to applications in gray matter. In various aspects, novel MRI-based approaches that can non-invasively monitor function of myelinated axonal fibers in PNS/CNS pathways as well as the underlying mechanisms that give rise to the observed functional MRI response are disclosed. The ex vivo perfused bullfrog sciatic nerve is an exceptionally robust model system that allows for well-defined stimulus intensity (duration and frequency of supramaximal voltage stimulus), recording of compound action potentials (CAP), and simultaneous MRI data acquisition. Electron microscopy of perfused nerves fixed resting or undergoing stimulation supports microstructural interpretations based upon electrophysiology and magnetic resonance.

Diffusion-weighted MRI (DWI) may be used to assess optic nerve response to visual stimulation in various organisms in vivo and ex vivo, including, but not limited to, vertebrates such as mice, frogs, and humans. To better understand the underlying mechanism of diffusion fMRI, a perfused isolated frog nerve system was used in conjunction with DBSI to assess nerve structural changes during repeated electrical stimulations. Through this investigation, DBSI was found to more sensitively detect nerve response than DWI or the more complicated diffusion tensor imaging (DTI) because the multi-tensor modeling offers a unique opportunity to specifically assess nerve structural changes without the confounding effects from surround environment such as CSF, inflammation, or other injuries. DBSI on living subjects undergoing visual stimulation using a flashing checkerboard was also performed. Close to 4-fold stronger optic nerve response using DBSI then conventional DTI was observed (see FIG. 1). In various aspects, this approach may be applied to all central and peripheral nervous systems with appropriate tasks.

In various aspects, "functional DBSI" assesses nerve function through dynamic measurements. The baseline DBSI measurements offer the conventional static DBSI assessment of nerve pathologies. In an aspect, "functional DBSI" may noninvasively and simultaneously assess nerve function and pathologies without the need to inject any tracers. The disclosed methods allow a direct correlation between underlying pathologies on nerve function. For example, one can assess nerve function in the presence of inflammation (likely reversible) or axonal loss (probably irreversible) facilitating stratification of patient management.

The disclosed methods can be used in various clinical applications. Functional assessment of a patient suffering neurological dysfunction is challenging and misdiagnosis is a frequent occurrence. One of the most promising neuroimaging technologies, resting-state fMRI, has shown utility to decipher connections between functional zones. However, resting-state fMRI remains incapable of determining where or how the disconnection occurs. The disclosed methods may be used to detect the connection between functional zones in brain and to provide insights to the function and pathologies of the connection. The disclosed methods offer a guide to treatment stratification allowing a more effective therapy.

For example, visual impairment may be detected by regular visual exams, RS-fMRI, or visual evoked potential. However, all of these existing detection methods reflect overall system response without the ability to pinpoint the breakpoint of the pathway. The disclosed method offers a means to detect the exact point where the signal is disrupted leading to visual impairment. With DBSI's ability to assess nerve pathologies the disclosed method will also provide the potential mechanism why the functional impairment occurs.

Conventional functional assessment methods may not be sufficient to detect subtle recovery of injured nerves. The disclosed method may detect subclinical function recovery and subclinical pathologies of a nerve. This would be crucial to allow a treatment to continue avoiding premature discontinuation for not detecting the conventional functional responses. For neurodegenerative disease such as AD, RS-fMRI and other neuroimaging technologies have been employed to predict the disease's progression. None of the current neuroimaging technologies assesses function of nerves connecting brain regions. It is likely that brain has the reserve to sustain the function in the presence of neuronal injury. Neurological impairment in AD or other neurodegenerative diseases could result from dysfunction and/or pathologies of connecting nerves.

In various aspects, a method of dynamic $T_2$ spectroscopy to monitor signatures of repetitive electrical stimulation is provided. In $T_2$ spectroscopy, the transverse magnetization signal decay in a multi-echo magnetic resonance measurement is decomposed into a spectrum of $T_2$ decay components. This approach applied in imaging mode has formed the basis of myelin water fraction (MWF) imaging, which is being pursued as a means to assess demyelination/remyelination in human brain diseases. In CNS white matter, two $T_2$ spectral components are observable, the shorter $T_2$ decay component ($T_2$<30 ms) corresponding to myelin water, and the longer component corresponding to intra- and extra-cellular water ($T_2$~200 ms). In tissue of the peripheral nervous system (PNS), three $T_2$ decay components are observable, which are attributed to myelin water ($T_2$<30 ms), extracellular water ($T_2$~50-100 ms) and intracellular water ($T_2$~200 ms). It has been suggested that the shorter extracellular than intracellular water $T_2$ in PNS is the result of efficient relaxation of transverse magnetization facilitated by the ubiquitous presence of collagen fibers. A number of investigators have successfully applied $T_2$ spectroscopy measurements to assess the myelin water fraction in ex vivo nerves.

Figure 26:
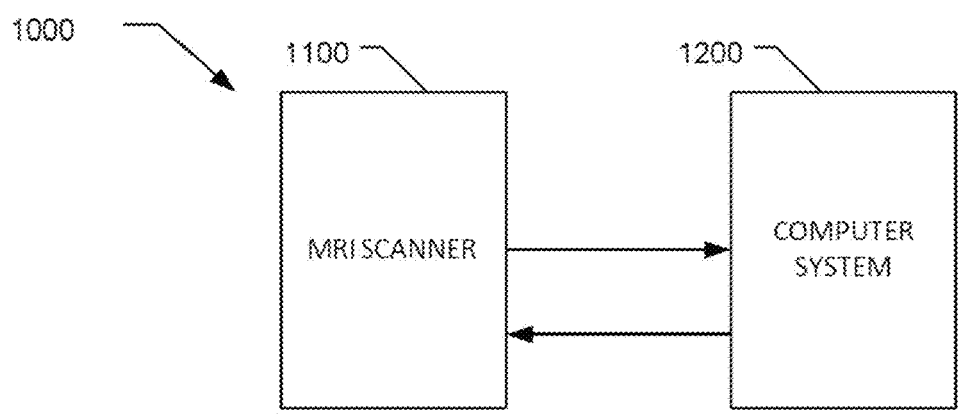
FIG. 26 is a schematic block diagram of an MRI imaging system in one aspect.

In various aspects, the methods described herein may be implemented using an MRI system. FIG. 26 is an illustration of an MRI imaging system 1000 in one aspect. As illustrated in FIG. 26, the MRI system 1000 may include an MRI scanner 1100 operatively coupled and/or in communication with a computer system 1200. In this aspect, the computer system 1200 is configured to receive data including, but not limited to, diffusion data, from the MRI scanner 1100, and is further configured to execute a plurality of stored executable instructions encoding one or more aspects of the method as described herein. In another aspect, the computer system 1200 may be further configured to operate the MRI scanner 1100 to obtain, for example, diffusion data by executing an additional plurality of stored executable instructions. The computer system 1200 may also be programmed to execute a machine learning application that learns classification of the MRI based images produced by the MRI scanner 1100 based on the method described herein. The computer system 1200 thus may detect nerve activity based on data from diffusion MRI scanning.

Although the present invention is described in connection with an exemplary imaging system environment, embodiments of the invention are operational with numerous other general purpose or special purpose imaging system environments or configurations. The imaging system environment is not intended to suggest any limitation as to the scope of use or functionality of any aspect of the invention. Moreover, the imaging system environment should not be interpreted as having any dependency or requirement relating to any one or combination of components illustrated in the exemplary operating environment. Examples of well-known imaging systems, environments, and/or configurations that may be suitable for use with aspects of the invention include, but are not limited to, personal computers, server computers, hand-held or laptop devices, multiprocessor systems, microprocessor-based systems, set top boxes, programmable consumer electronics, mobile telephones, network PCs, minicomputers, mainframe computers, distributed computing environments that include any of the above systems or devices, and the like.

Computer systems, as described herein, refer to any known computing device and computer system. As described herein, all such computer systems include a processor and a memory. However, any processor in a computer system referred to herein may also refer to one or more processors wherein the processor may be in one computing device or a plurality of computing devices acting in parallel. Additionally, any memory in a computer device referred to herein may also refer to one or more memories wherein the memories may be in one computing device or a plurality of computing devices acting in parallel.

The term processor, as used herein, refers to central processing units, microprocessors, microcontrollers, reduced instruction set circuits (RISC), application specific integrated circuits (ASIC), logic circuits, and any other circuit or processor capable of executing the functions described herein. The above are examples only, and are thus not intended to limit in any way the definition and/or meaning of the term "processor."

As used herein, the term "database" may refer to either a body of data, a relational database management system (RDBMS), or to both. As used herein, a database may include any collection of data including hierarchical databases, relational databases, flat file databases, object-relational databases, object-oriented databases, and any other structured collection of records or data that is stored in a computer system. The above examples are example only, and thus are not intended to limit in any way the definition and/or meaning of the term database. Examples of RDBMSs include, but are not limited to including, Oracle® Database, MySQL, IBM® DB2, Microsoft® SQL Server, Sybase®, and PostgreSQL. However, any database may be used that enables the systems and methods described herein. (Oracle is a registered trademark of Oracle Corporation, Redwood Shores, Calif.; IBM is a registered trademark of International Business Machines Corporation, Armonk, N.Y.; Microsoft is a registered trademark of Microsoft Corporation, Redmond, Wash.; and Sybase is a registered trademark of Sybase, Dublin, Calif.)

In one embodiment, a computer program is provided to enable the data processing of the method as described herein, and this program is embodied on a computer readable medium. In an example embodiment, the computer system is executed on a single computer system, without requiring a connection to a server computer. In a further embodiment, the computer system is run in a Windows® environment (Windows is a registered trademark of Microsoft Corporation, Redmond, Wash.). In yet another embodiment, the computer system is run on a mainframe environment and a UNIX® server environment (UNIX is a registered trademark of X/Open Company Limited located in Reading, Berkshire, United Kingdom). Alternatively, the computer system is run in any suitable operating system environment. The computer program is flexible and designed to run in different environments without compromising any major functionality. In some embodiments, the computer system includes multiple components distributed among a plurality of computing devices. One or more components may be in the form of computer-executable instructions embodied in a computer-readable medium.

The computer systems and processes are not limited to the specific embodiments described herein. In addition, components of each computer system and each process can be practiced independent and separate from other components and processes described herein. Each component and process also can be used in combination with other assembly packages and processes.

Figure 27:
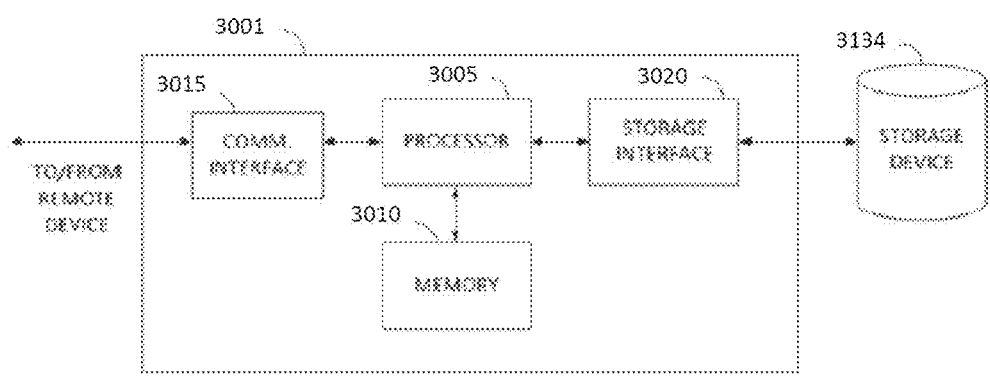
FIG. 27 is a schematic block diagram of an example server system.

In one embodiment, the computer system may be configured as a server system. FIG. 27 illustrates an example configuration of a server system 3001 used to receive measurements from the MRI scanner 1100 (not illustrated). Referring again to FIG. 27, server system 3001 may also include, but is not limited to, a database server. In this example embodiment, server system 3001 performs all of the steps used to implement the method as described herein.

In this aspect, the server system 3001 includes a processor 3005 for executing instructions. Instructions may be stored in a memory area 3010, for example. The processor 3005 may include one or more processing units (e.g., in a multi-core configuration) for executing instructions. The instructions may be executed within a variety of different operating systems on the server system 3001, such as UNIX®, LINUX, Microsoft Windows®, etc. It should also be appreciated that upon initiation of a computer-based method, various instructions may be executed during initialization. Some operations may be required in order to perform one or more processes described herein, while other operations may be more general and/or specific to a particular programming language (e.g., C, C#, C++, Java, or any other suitable programming languages).

The processor 3005 is operatively coupled to a communication interface 3015 such that server system 3001 is capable of communicating with a remote device, such as the MRI scanner 1100, a user system, or another server system 3001. For example, communication interface 3015 may receive requests (e.g., requests to provide an interactive user interface to receive sensor inputs and to control one or more devices of system 1000 from a client system via the Internet.

Processor 3005 may also be operatively coupled to a storage device 3134. Storage device 3134 is any computer-operated hardware suitable for storing and/or retrieving data. In some embodiments, storage device 3134 is integrated in server system 3001. For example, server system 3001 may include one or more hard disk drives as storage device 3134. In other embodiments, storage device 3134 is external to server system 3001 and may be accessed by a plurality of server systems 3001. For example, storage device 3134 may include multiple storage units such as hard disks or solid-state disks in a redundant array of inexpensive disks (RAID) configuration. Storage device 3134 may include a storage area network (SAN) and/or a network attached storage (NAS) system.

In some embodiments, processor 3005 is operatively coupled to storage device 3134 via a storage interface 3020. Storage interface 3020 is any component capable of providing processor 3005 with access to storage device 3134. Storage interface 3020 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 3005 with access to storage device 3134.

Memory area 3010 may include, but are not limited to, random access memory (RAM) such as dynamic RAM (DRAM) or static RAM (SRAM), read-only memory (ROM), erasable programmable read-only memory (EPROM), electrically erasable programmable read-only memory (EEPROM), non-volatile RAM (NVRAM), registers, hard disk memory, a removable disk, a CD-ROM, or any other form of computer-readable storage medium known in the art. The above memory types are exemplary only, and are thus not limiting as to the types of memory usable for storage of a computer program.

In another embodiment, the computer system may be provided in the form of a computing device, such as a computing device 402 (shown in FIG. 28). Computing device 402 includes a processor 404 for executing instructions. In some embodiments, executable instructions are stored in a memory area 406. Processor 404 may include one or more processing units (e.g., in a multi-core configuration). Memory area 406 is any device allowing information such as executable instructions and/or other data to be stored and retrieved. Memory area 406 may include one or more computer-readable media.

In another embodiment, the memory included in the computing device 402 may include a plurality of modules. Each module may include instructions configured to execute using at least one processor. The instructions contained in the plurality of modules may implement at least part of the method for simultaneously regulating a plurality of process parameters as described herein when executed by the one or more processors of the computing device. Non-limiting examples of modules stored in the memory of the computing device include: a first module to receive measurements from one or more sensors and a second module to control one or more devices of the MRI imaging system 1000.

Computing device 402 also includes one media output component 408 for presenting information to a user 400. Media output component 408 is any component capable of conveying information to user 400. In some embodiments, media output component 408 includes an output adapter such as a video adapter and/or an audio adapter. An output adapter is operatively coupled to processor 404 and is further configured to be operatively coupled to an output device such as a display device (e.g., a liquid crystal display (LCD), organic light emitting diode (OLED) display, cathode ray tube (CRT), or "electronic ink" display) or an audio output device (e.g., a speaker or headphones).

In some embodiments, client computing device 402 includes an input device 410 for receiving input from user 400. Input device 410 may include, for example, a keyboard, a pointing device, a mouse, a stylus, a touch sensitive panel (e.g., a touch pad or a touch screen), a camera, a gyroscope, an accelerometer, a position detector, and/or an audio input device. A single component such as a touch screen may function as both an output device of media output component 408 and input device 410.

Computing device 402 may also include a communication interface 412, which is configured to communicatively couple to a remote device such as server system 3001 or a web server. Communication interface 412 may include, for example, a wired or wireless network adapter or a wireless data transceiver for use with a mobile phone network (e.g., Global System for Mobile communications (GSM), 3G, 4G or Bluetooth®) or other mobile data network (e.g., Worldwide Interoperability for Microwave Access (WIMAX)).

Stored in memory 406 are, for example, computer-readable instructions for providing a user interface to user 400 via media output component 408 and, optionally, receiving and processing input from input device 410. A user interface may include, among other possibilities, a web browser and an application. Web browsers enable users 400 to display and interact with media and other information typically embedded on a web page or a website from a web server. An application allows users 400 to interact with a server application.

Exemplary embodiments of methods, systems, and apparatus for use in diffusion basis spectrum imaging are described herein. The methods, systems, and apparatus are not limited to the specific embodiments described herein but, rather, operations of the methods and/or components of the systems and/or apparatus may be utilized independently and separately from other operations and/or components described herein. Further, the described operations and/or components may also be defined in, or used in combination with, other systems, methods, and/or apparatus, and are not limited to practice with only the systems, methods, and apparatus described herein.

The order of execution or performance of the operations in the embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the disclosure.

It will be understood by those of skill in the art that information and signals may be represented using any of a variety of different technologies and techniques. For example, data, instructions, commands, information, signals, bits, symbols, and/or chips may be represented by voltages, currents, electromagnetic waves, magnetic fields or particles, optical fields or particles, or any combination thereof. Similarly, the various illustrative logical blocks, modules, circuits, and algorithm operations described herein may be implemented as electronic hardware, computer software, or a combination of both, depending on the application and the functionality. Moreover, the various logical blocks, modules, and circuits described herein may be implemented or performed with a general purpose computer, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. Exemplary general-purpose processors include, but are not limited to only including, microprocessors, conventional processors, controllers, microcontrollers, state machines, or a combination of computing devices.

When introducing elements of aspects of the invention or embodiments thereof, the articles "a," "an," "the," and "said" are intended to mean that there are one or more of the elements. The terms "comprising," "including," and "having" are intended to be inclusive and mean that there may be additional elements other than the listed elements.

In the examples described below, it was demonstrated that short-term dynamic changes in diffusion MRI and T2 relaxation properties accompany repetitive electrical activity in myelinated nerve fibers. These changes were observable on the timescale of minutes. From the MRI electrophysiology, and microscopy data (post-stimulation-fixed or quiescent-fixed tissues), a consistent picture emerges—repetitive electrical activity leads to osmotically-driven microstructural modification of the myelinated fibers. The dynamic changes in water T2 spectral components with electrical activity in WM observed using the disclosed methods may form the basis of an additional, complementary MRI-based approach to non-invasively assess WM function in vivo. Further, it was demonstrated that WM diffusion fMRI can non-invasively localize foci of electrical conduction blockage in axonal pathways, thereby providing an important clinical tool for use in management of WM neurodegenerative diseases and/or neurotrauma.

EXAMPLES

Example 0: MRI Imaging of Optic Nerve Pathology in Mice

To compare the effectiveness of the DBSI and DTI analysis models for the detection of optic nerve pathology in mice, the following experiments were conducted.

Eight 10-week-old female C57BL/6 mice underwent optic nerve DBSI, followed by a week-long recuperation prior to active immunization for experimental autoimmune encephalomyelitis (EAE). Visual acuity of all mice was assessed daily. Longitudinal DBSI was performed in mouse optic nerves at baseline (naïve, before immunization), before, during, and after the onset of optic neuritis.

Figures 19A, 19B, 19C:
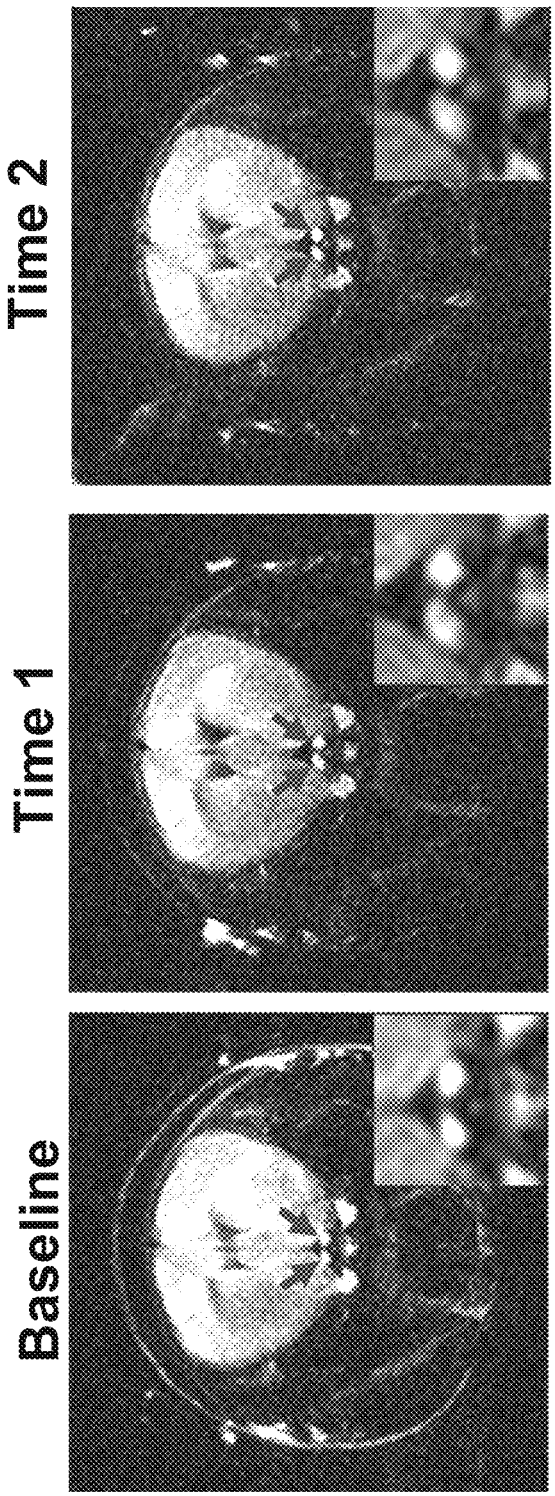
FIG. 19A is a cross-sectional MPRAGE image of an Experimental Autoimmune Encephalomyelitis (EAE) mouse brain obtained prior to the induction of EAE, in which the red arrows denote the left and right optic nerves shown enlarged in the inset.
FIG. 19B is a cross-sectional MPRAGE image of the EAE mouse brain shown in FIG. 19A obtained at a first interval after induction of EAE.
FIG. 19C is a cross-sectional MPRAGE image of the EAE mouse brain shown in FIGS. 19A and 19B obtained at a second interval after induction of EAE.

FIG. 19A is an exemplary diffusion-weighted MRI image of the optic nerves of a mouse prior to active immunization. FIGS. 19B and 19C are exemplary diffusion-weighted MRI images of the optic nerves at two stages of optic neuritis. Inset images on each of FIGS. 19A-19C shows a close-up image of the optic nerves.

Figure 20A:
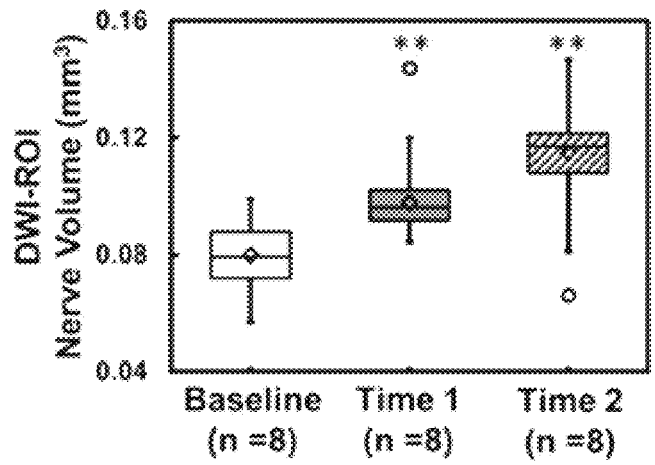
FIG. 20A is a bar graph summarizing the mean optical nerve volumes obtained from diffusion weighted images (DWI) of a population of EAE mice before and after induction of EAE.
Figure 20B:
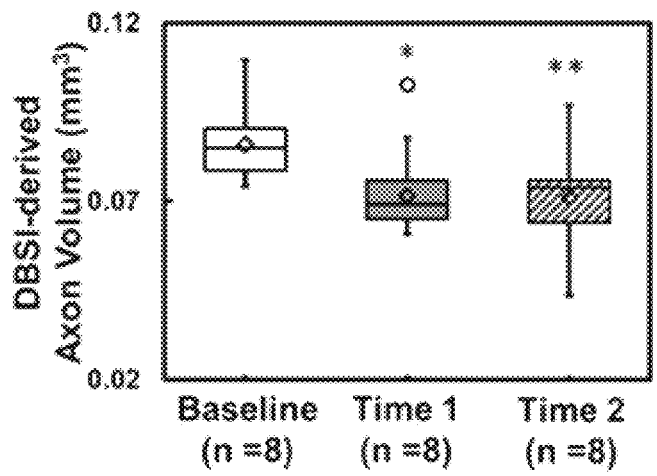
FIG. 20B is a bar graph summarizing mean axon volumes within the optical nerves obtained from DBSI analysis of a population of EAE mice before and after exposure to two intervals of a visual stimulus.
Figure 20C:
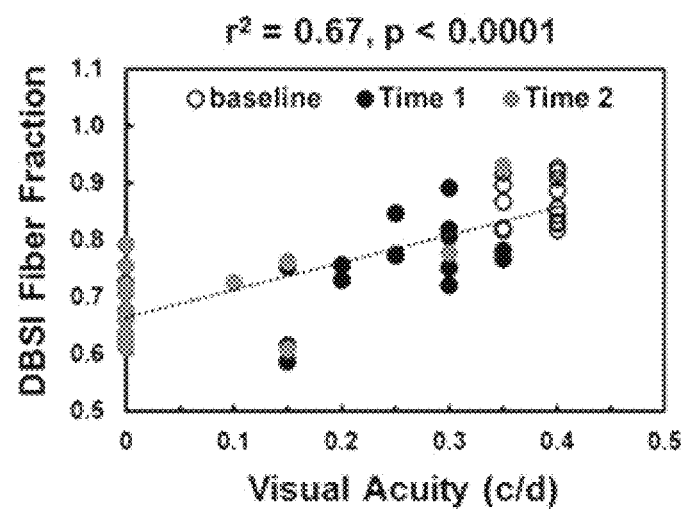
FIG. 20C is a scatter graph summarizing a relationship between the DBSI-derived fiber fractions and measured visual acuity of individual EAE mice before and after induction of EAE.
Figure 21B:
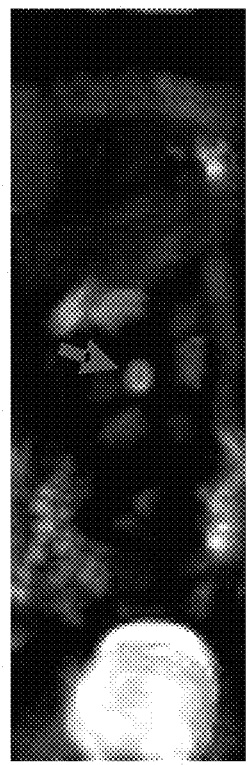
FIG. 21B is a diffusion-weighted MRI image of the brain of the human muscular dystrophy patient shown in FIG. 21A, with a red arrow denoting the optic nerve.
Figure 21C:
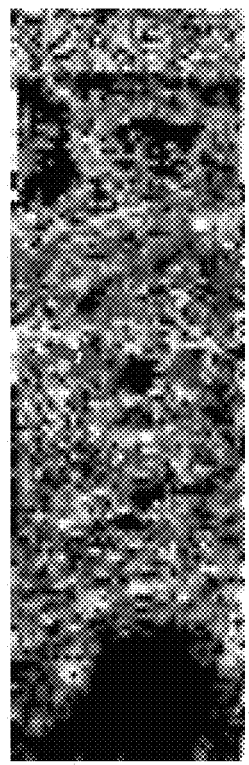
FIG. 21C is a map of DBSI-derived fiber fraction calculated using the diffusion MRI data from FIG. 21B, with a red arrow denoting the optic nerve.
Figure 21D:
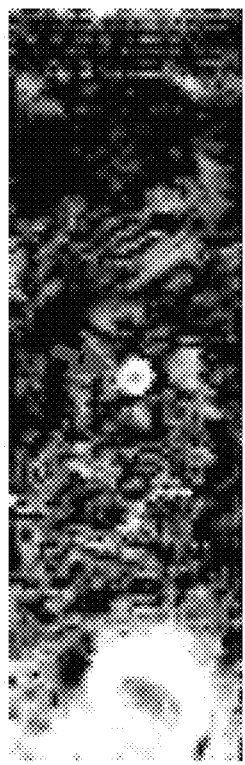
FIG. 21D is a map of DBSI-derived free diffusion fraction calculated using the diffusion MRI data from FIG. 21B, with a red arrow denoting the optic nerve.
Figure 21A:
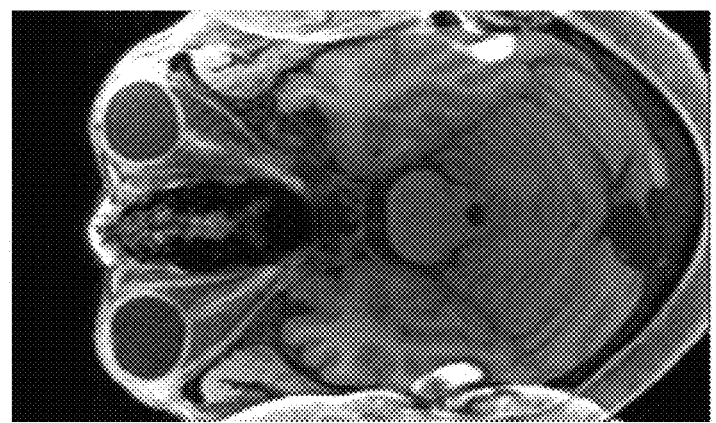
FIG. 21A is a T1-weighted MRI image of a brain of a human muscular dystrophy patient with unilateral optic neuritis characterized by axonal injury and inflammation.
Figure 22:
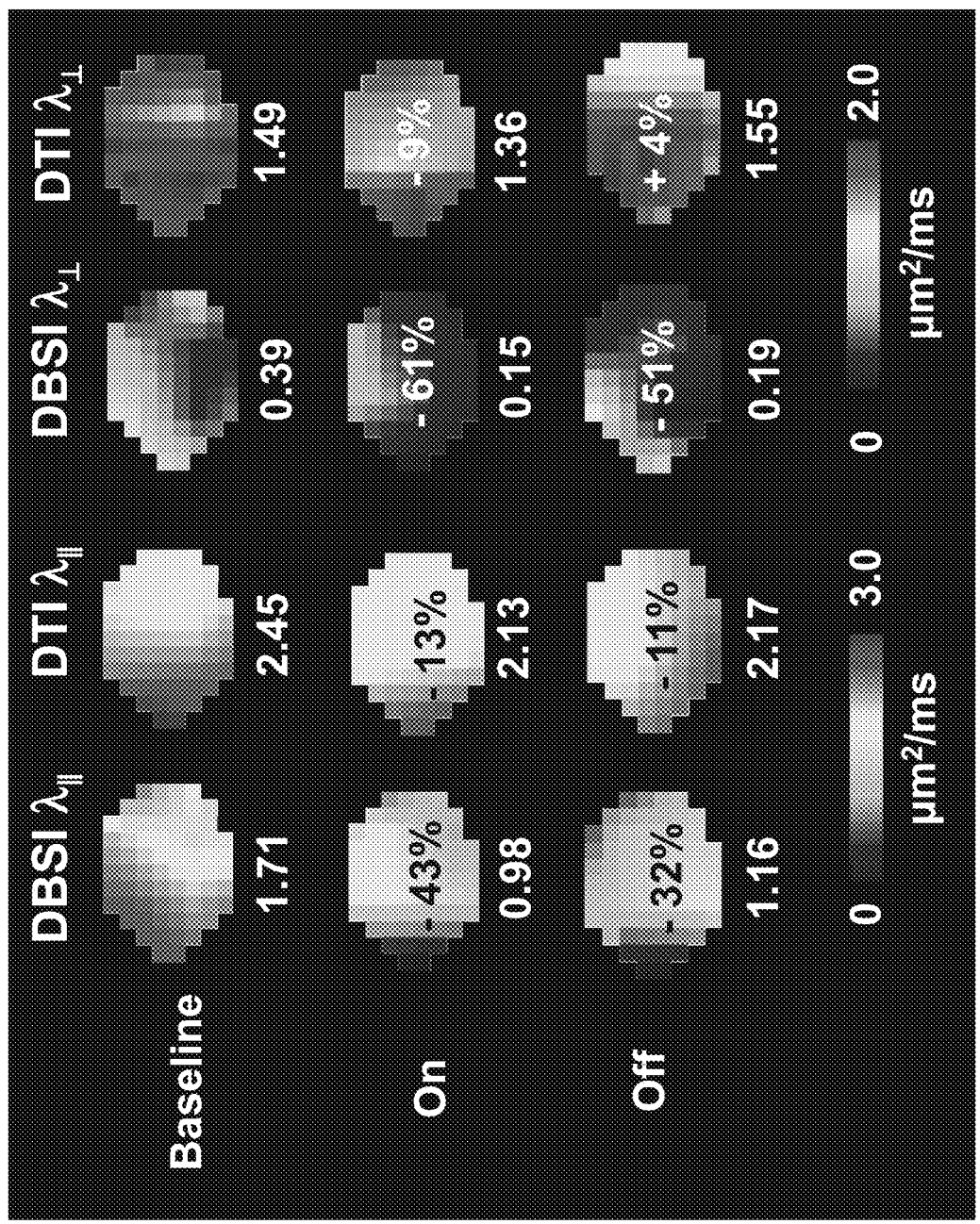
FIG. 22 is an image comparing maps of DBSI-measured and DTI-measured $\lambda_\parallel$ and $\lambda_\perp$ obtained from an optic nerve of the muscular dystrophy patient of FIGS. 21A, 21B, 21C, and 21D obtained before, during, and after exposure to a visual stimulus.

FIG. 20A is a bar graph of the mean nerve volumes estimated from the diffusion-weighted MRI images at baseline, time 1 and time 2. Nerve volume steadily increased after active immunization, indicating swelling of the optic nerves. FIG. 20B is a bar graph of the mean axon volumes estimated from the DBSI analysis of the diffusion-weighted MRI data at baseline, time 1 and time 2. Axon volumes decreased after active immunization, indicating axonal loss as a result of the induced optic neuritis. FIG. 20C is a scatter graph of the DBSI fiber fractions plotted as a function of the measured visual acuity of the mice obtained at baseline, time 1 and time 2. DBSI fiber fractions steadily decreased as the induced optic neuritis progressed, and DBSI fiber fraction decreased as visual acuity degraded.

Example 1: DBSI Analysis of Human Optic Nerve Activation and Deactivation In Vivo To compare the effectiveness of the DBSI and DTI analysis models for the detection of optic nerve function non-invasively in human subjects, the following experiments were conducted.

Single-direction diffusion functional MRI (fMRI) has been previously employed to assess activation of mouse optic nerve via decreased apparent diffusion coefficient perpendicular to axonal fibers ($\Delta ADC_\perp$) during flashing-light visual or direct electrical stimulation. Unlike blood-oxygen level dependent (BOLD) fMRI, the stimulation-induced $\Delta ADC_\perp$ was found to be independent of vascular effects using diffusion functional MRI. This functional fMRI response ($\Delta ADC_\perp$) was found to be attenuated in optic nerves from mice with optic neuritis.

In this experiment, diffusion-weighted imaging (DWI) measurements were performed in human optic nerves with visual stimulation and the data were analyzed using diffusion basis spectrum imaging (DBSI) and diffusion tensor imaging (DTI). It was hypothesized that DBSI-estimated $\Delta\lambda_\perp$ was more sensitive for detection of axonal activation than DTI-$\Delta\lambda_\perp$ or DWI-$\Delta ADC_\perp$ since DBSI enabled the exclusion of confounding effects of surrounding CSF to a relatively higher extent as compared to conventional DTI.

Figure 1B:
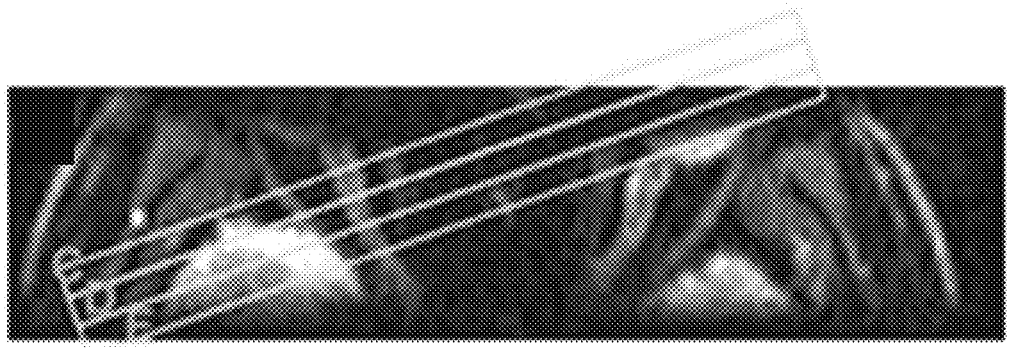
FIG. 1B is an image showing a reduced field-of-view diffusion-weighted MRI image (DWI) of a portion of the human patient imaged in FIG. 1A with slices C, D, and E identified by overlaid yellow rectangles.
Figure 1C:
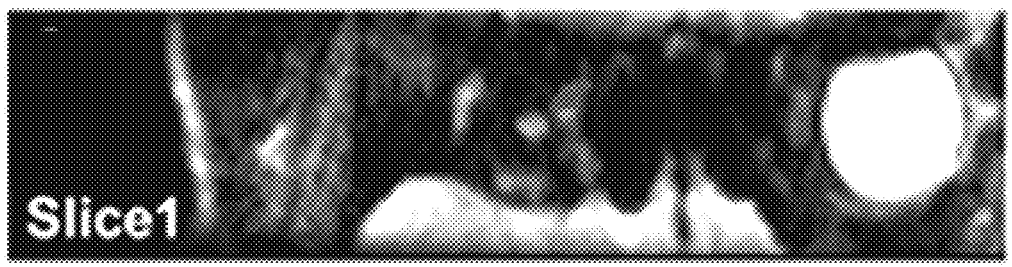
FIG. 1C is a DWI of slice 1 corresponding to the yellow rectangle marked "C" in FIG. 1B, with the a red arrow marking the optic nerve.
Figure 1D:
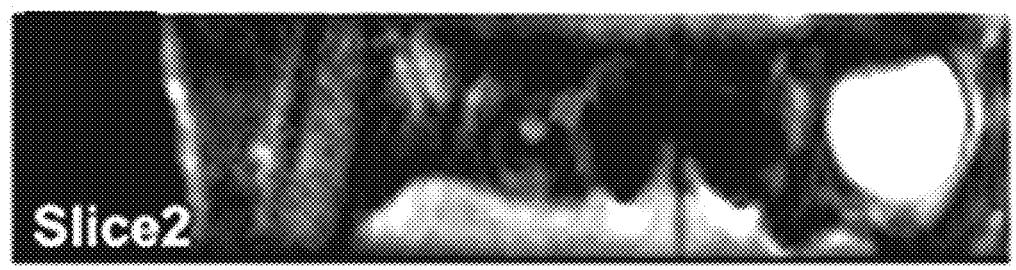
FIG. 1D is a DWI of slice 2 corresponding to the yellow rectangle marked "D" in FIG. 1B, with the a red arrow marking the optic nerve.
Figure 1E:
FIG. 1E is a DWI of slice 3 corresponding to the yellow rectangle marked "E" in FIG. 1B, with the a red arrow marking the optic nerve.

DWI (25-direction repeated with polarity reversal, max b-value=1,000 s/mm2, 3T Siemens® Prisma) was performed with inner-volume single-shot EPI using a 64-channel head coil: TR=2.5 s, TE=53.8 ms, $\Delta$=18 ms, d=6 ms, in-plane resolution=1.1×1.1 mm, slice thickness=4 mm, echo-train length=30, and acquisition time=2.4 minutes. Imaging slices were perpendicular to optic nerve (FIGS. 1B, 1C, and 1D). A 32-year-old healthy female subject had four separate visits. Each diffusion fMRI measurement consisted of a series of three baseline images, three stimulation images (8 Hz flashing checkerboard, FIGS. 1F and 1G), and three stimulation-off images. DBSI-$\lambda_\perp$ and DTI-$\lambda_\perp$ were derived using lab-developed software.

Figure 2:
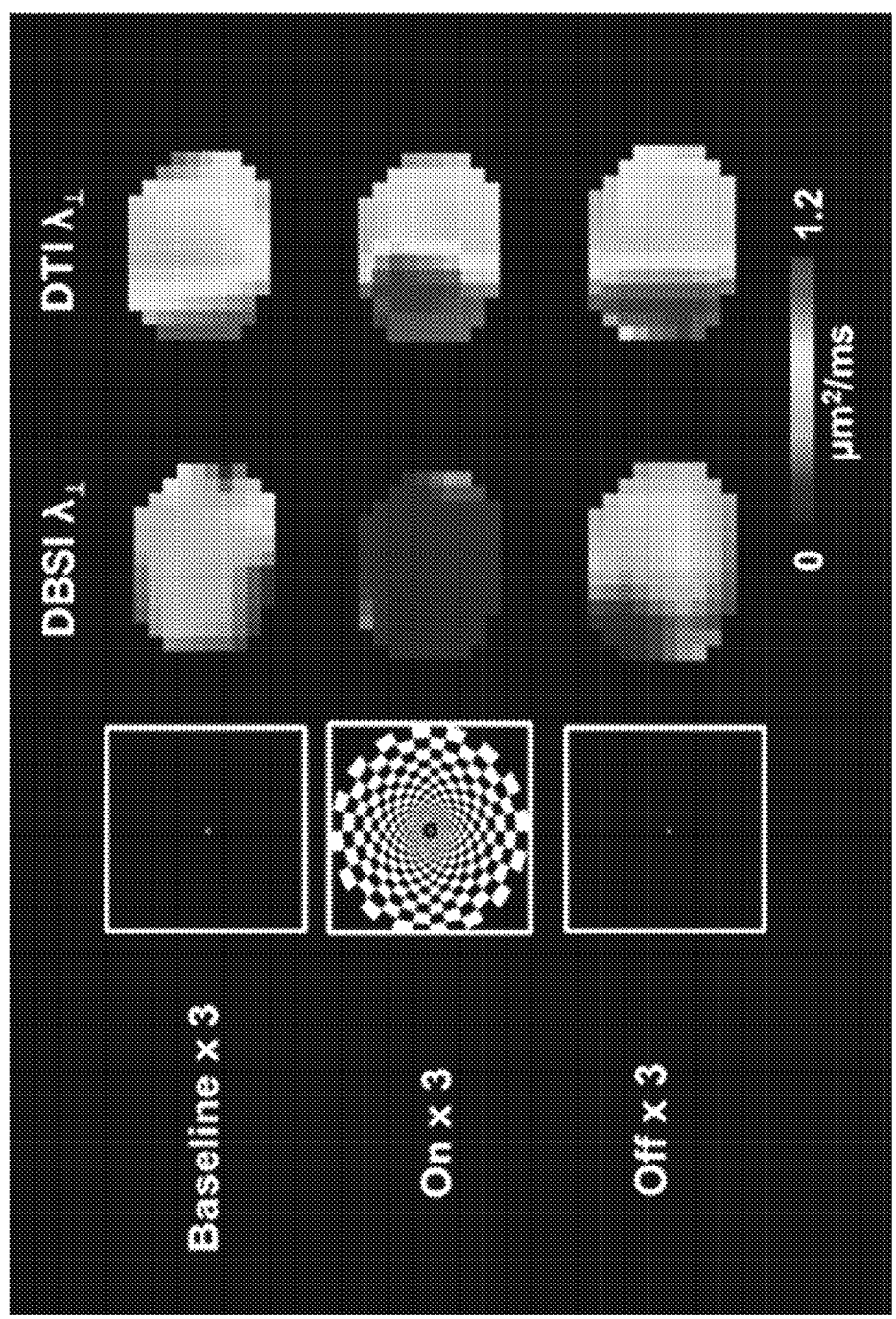
FIG. 2 is an image showing maps of DBSI-measured $\lambda_\perp$ and DTI-measured $\lambda_\perp$ obtained from an optic nerve of a living human subject before, during, and after exposure to a visual stimulus.
Figure 3A:
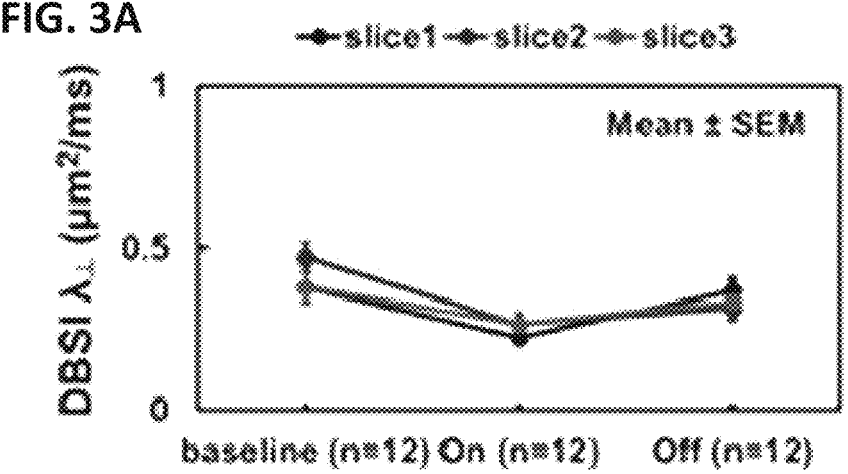
FIG. 3A is a graph showing DBSI-measured $\lambda_\perp$ for slices 1, 2, and 3 of FIGS. 1B, 1C, and 1D, respectively, obtained from an optic nerve of a living human subject before, during, and after exposure to the visual stimulus of FIG. 1G.
Figure 3B:
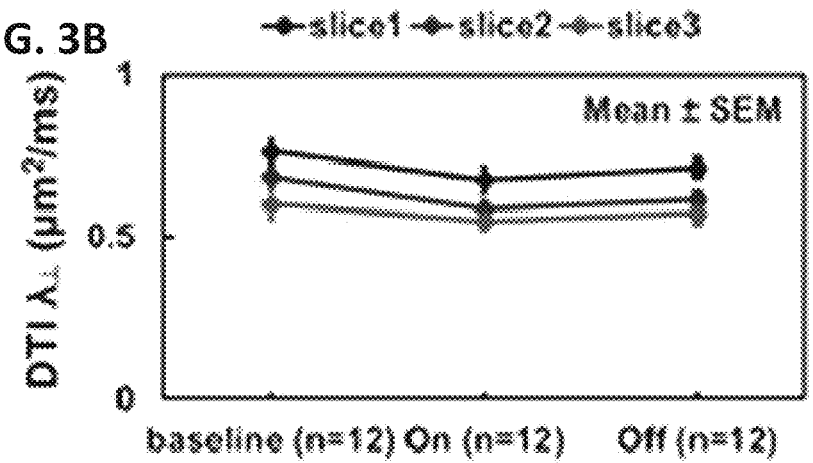
FIG. 3B is a graph showing DTI-measured $\lambda_\perp$ for slices 1, 2, and 3 of FIGS. 1B, 1C, and 1D, respectively, obtained from an optic nerve of a living human subject before, during, and after exposure to the visual stimulus of FIG. 1G.
Figure 3C:
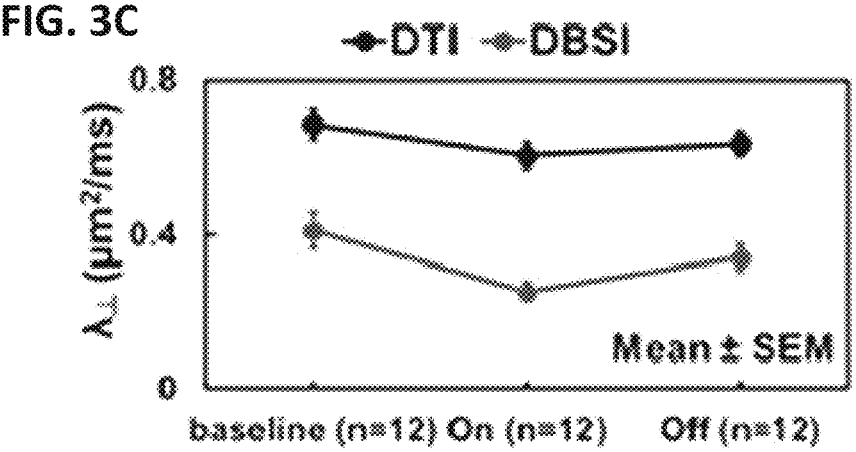
FIG. 3C is a graph comparing the mean DBSI-measured $\lambda_\perp$ from FIG. 3A and the mean DTI-measured $\lambda_\perp$ from FIG. 3B.
Figure 4:
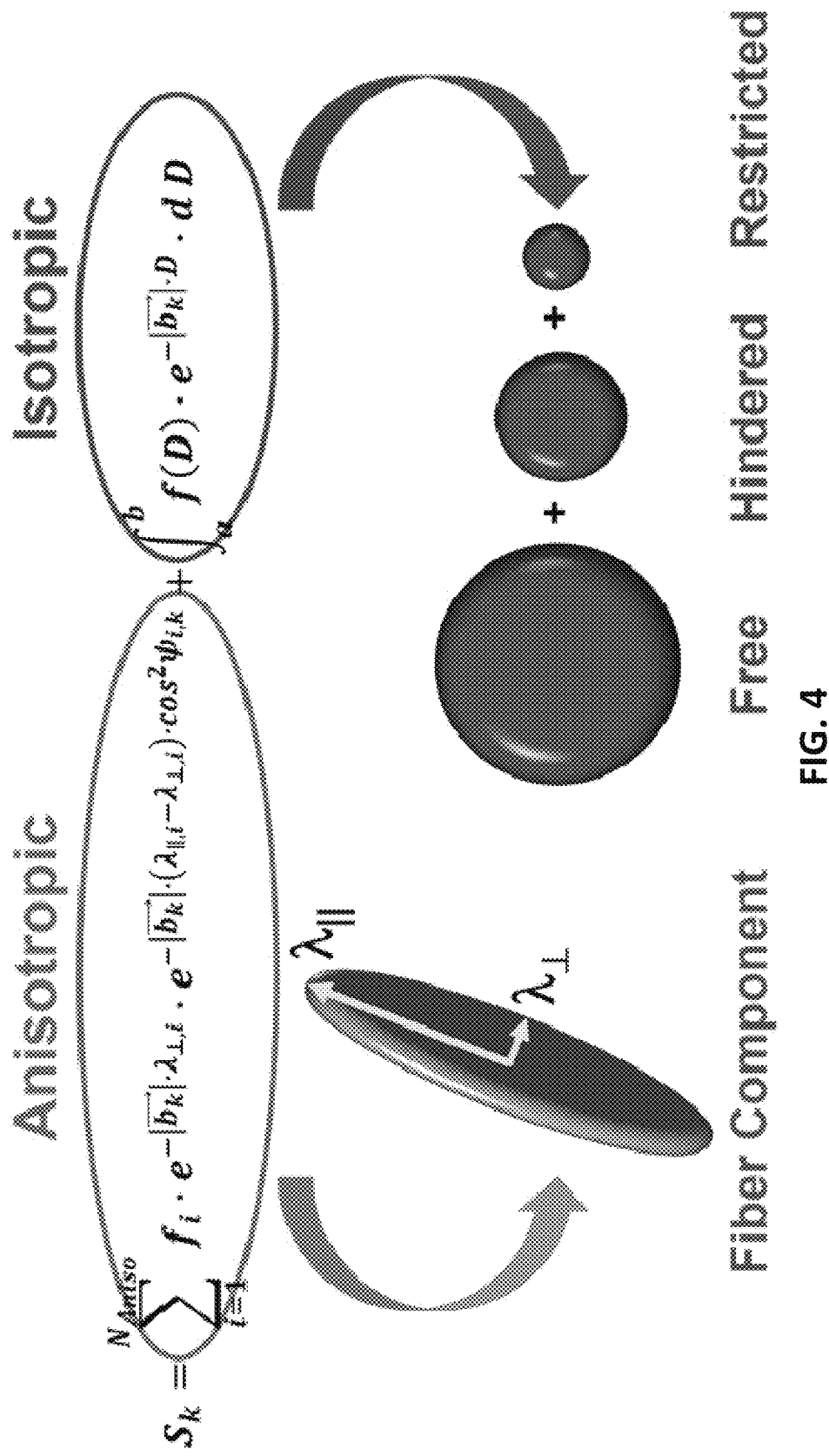
FIG. 4 is a pictorial schematic diagram summarizing the diffusion basis spectrum imaging (DBSI) signal modeling.

As illustrated in FIG. 2, the baseline DBSI-$\lambda_\perp$ was lower than DTI-$\lambda_\perp$, suggesting that DBSI minimized the confounding effects of the surrounding CSF. During visual stimulation, DBSI-$\lambda_\perp$ and DTI-$\lambda_\perp$ significantly decreased comparing to its baseline in all image slices (see FIGS. 3A and 3B) by 39% (0.41±0.04 baseline vs. 0.25±0.02 On, Mean±SEM) and 12% (0.68±0.04 baseline vs. 0.60±0.03 On, Mean±SEM), respectively (average of 4 visits, FIG. 3C). Across the 4 visits, the results were highly consistent.

In another experiment, seven healthy subjects were recruited. Three had normal vision uncorrected, and four wore contact lenses. Scans were performed on a 3T Siemens® Prisma scanner. A 64-channel head coil was used with a mirror to allow the subject to see the flashing checkerboard while in the scanner. One eye was covered by gauze and taped shut with medical tape.

Figure 1F:
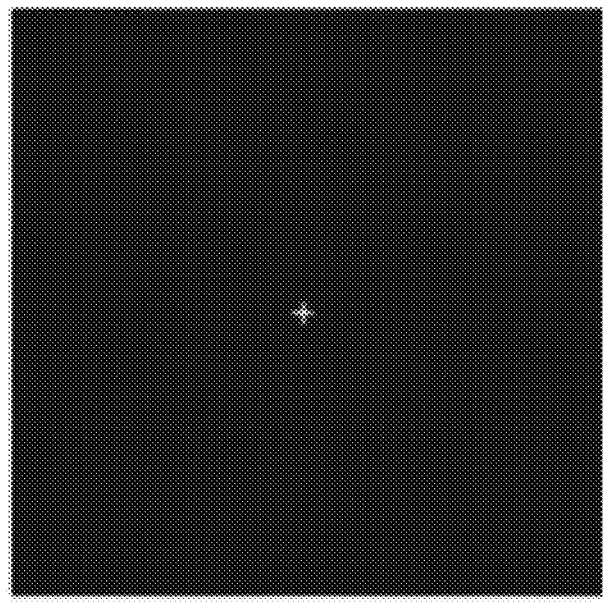
FIG. 1F is an image showing the visual stimulus shown to the human subjects during a resting condition of the optical nerve.
Figure 1G:
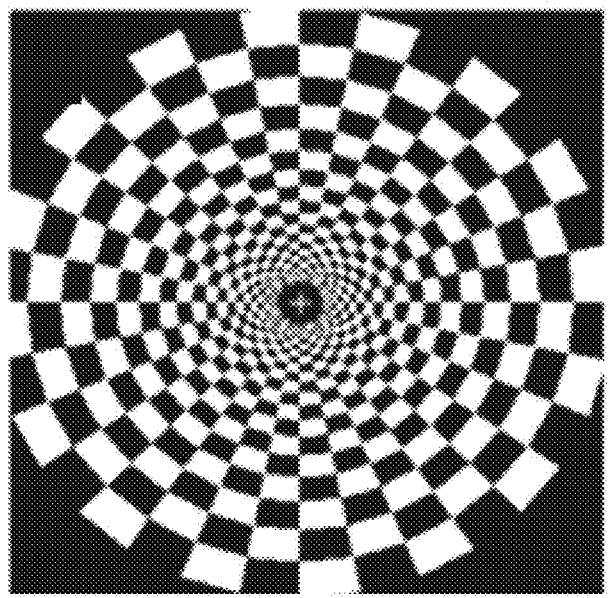
FIG. 1G is an image showing the visual stimulus shown to the human subjects during an activation condition of the optical nerve.
Figure 16A:
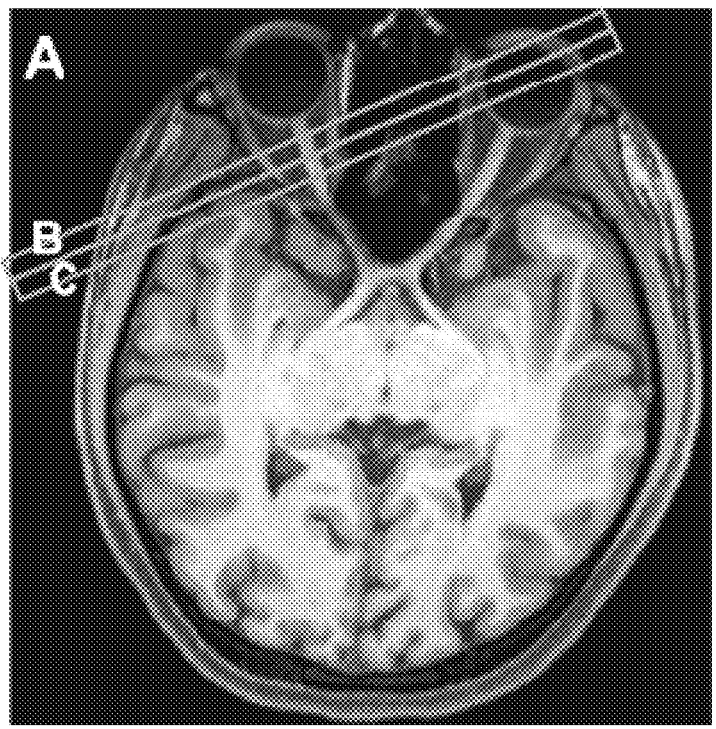
FIG. 16A is a representative MPRAGE image depicting two optic nerves with two rectangles superimposed to denote two adjusted imaging planes defined perpendicular to the right optic nerve.
Figure 16B:
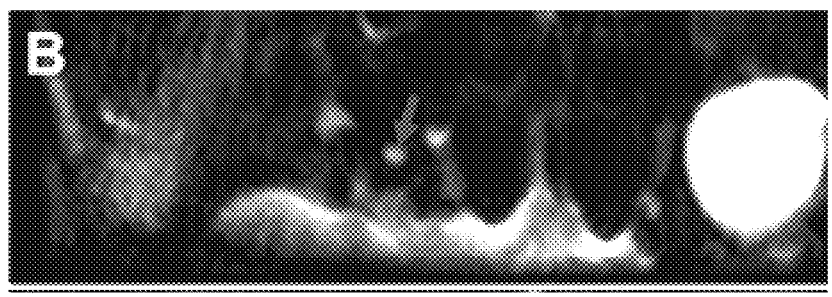
FIG. 16B is a cross-sectional MPRAGE image defined within the adjusted imaging plane marked 'B' in FIG. 16A, in which a red arrow denotes the right optic nerve.
Figure 16C:
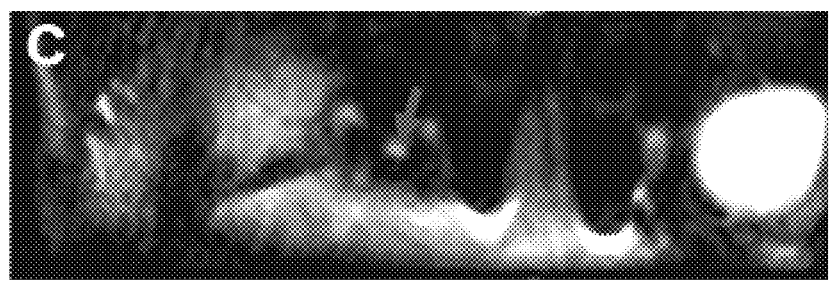
FIG. 16C is a cross-sectional MPRAGE image defined within the adjusted imaging plane marked 'C' in FIG. 16A, in which a red arrow denotes the right optic nerve.
Figure 17:
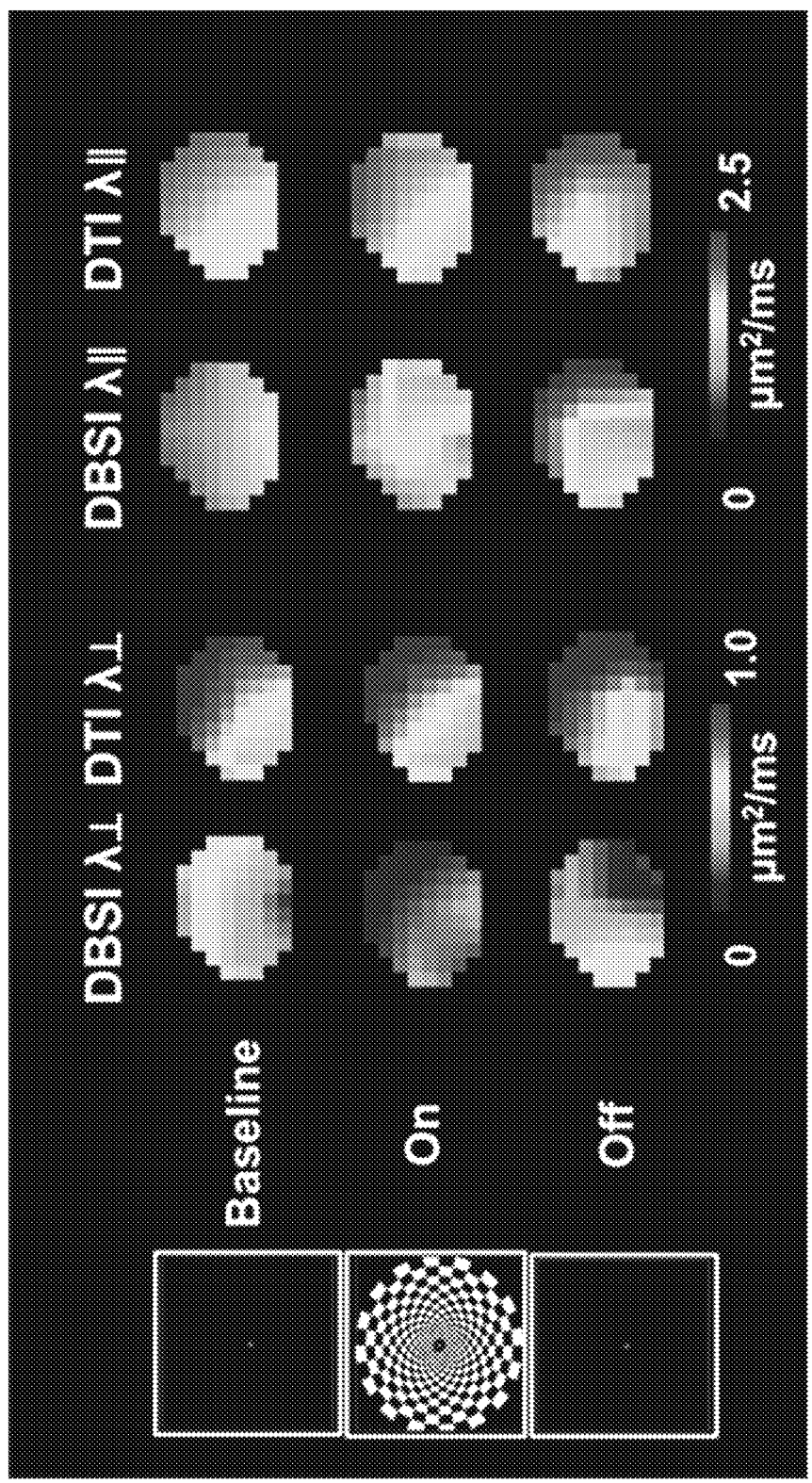
FIG. 17 is an image comparing maps of DBSI-measured and DTI-measured $\lambda_\perp$ and $\lambda_\parallel$ obtained from an optic nerve of a living human subject before, during, and after exposure to a visual stimulus.

Whole brain MPRAGE was acquired to precisely locate the optic nerves (FIG. 16A). Two image slices (FIG. 16B and FIG. 16C) were adjusted perpendicular to the tested optic nerve (FIG. 1A, blue rectangles). Imaging was performed in 31 directions with 31 b-values (max b-value=1,000 s/mm$^2$) including one b=0 diffusion-weighted image using inner-volume single-shot EPI: TR=2.5 s, TE=53.8 ms, $\Delta$=18 ms, $\delta$=6 ms, in-plane resolution=1.1×1.1 mm, slice thickness=4 mm, echo-train length=30, and acquisition time=1.26 minutes. Each diffusion fMRI measurement consisted of a series of three baseline, three stimulation (8 Hz flashing checkerboard), and three stimulation-off images (FIGS. 1F and 1G). Thus, three measurements were averaged for each condition.

Raw DWIs were post-processed and coregistered before DBSI-$\lambda_\perp$ and DTI-$\lambda_\perp$ were derived using lab-developed software. Measurements from both image slices were averaged for each subject.

Baseline DBSI-$\lambda_\perp$ was lower and $\lambda_\parallel$ was higher than baseline DTI-$\lambda_\perp$ and $\lambda_\parallel$, respectively (FIGS. 17, 18A, 18B, and 18C). This suggested that DBSI minimized the confounding effects of surrounding CSF and resident cells. During visual stimulation, DBSI-$\lambda_\perp$ and -$\lambda_\parallel$ were 43% (p<0.05, FIG. 18A) and 13% (p=0.05, FIG. 18B) lower than their baseline values. After stimulation, both DBSI-$\lambda_\perp$ and -$\lambda_\parallel$ normalized toward the baseline value (FIGS. 18A, 18B, and 18C). Meanwhile, DTI-$\lambda_\perp$ and $\lambda_\parallel$ were not changed during visual stimulation, suggesting that changes may have been masked by confounding partial-volume effects or that DTI is less sensitive to change than DBSI (FIGS. 18A, 18B, and 18C).

The results of these experiments demonstrated that DBSI-$\Delta\lambda_\perp$ detected greater axonal activation-induced changes than DTI-$\Delta\lambda_\perp$. These experiments are the first to detect axonal function-associated diffusion changes in a living human subject.

Example 2: Comparison of DTI, DBSI and T2 Spectral Analysis of Frog Sciatic Nerve Activation and Deactivation Ex Vivo To demonstrate the ability to perform function imaging of neuronal activity using DBSI and T2 spectral methods, the following experiments were conducted. The experiments were carried out on perfused, ex vivo frog sciatic nerves, which due to their extreme robustness have been the subject of numerous electrophysiology and MRI studies.

Methods

Frog Nerve Preparation

Jumbo bullfrogs (*Rana catesbeiana*) were purchased from Rana Ranch (Twin Falls, Id.) and housed in a climate-controlled environment with a 12/12 hr-light/dark cycle. The animal housing consisted of a standard clear plastic container [18"(1)×10"(w)×10"(h)] holding 1.5 L of water and tipped at an angle to provide a dry area within the cage. Frogs were fed pelleted chow (5LP3, Lab Diet, St. Louis, Mo.) three times per week.

Frogs were anesthetized in a solution of tricaine methanesulfonate (Sigma-Aldrich, St. Louis, Mo.), 0.5 g/L in dechlorinated tap water with pH adjusted to 7.4. Once immobilized, frogs were decapitated and pithed. After removal of the skin, the body was pinned into a dissecting tray and a 4-5 cm segment of the sciatic nerve was dissected from the lower back to just proximal to its branching into peroneal and tibial nerves. During dissection, the surgical field was irrigated frequently with frog Ringer's solution without glucose (see below) to maintain tissue moisture content. After gently debriding fat and surrounding connective tissue from the sciatic nerve, the nerve segment was tied off first at the proximal and then at the distal end with 2-0 silk suture and cut out. Twitching of the gastrocnemius muscle upon tying off the nerve at the proximal end served as verification that the sciatic nerve has not been damaged during the dissection procedure. Once dissected, the tied-off nerve was placed in a Petri dish of oxygenated frog Ringer's solution containing glucose at room temperature.

The frog Ringer's solution recipe used in these experiments was intended to match the ionic composition and osmolarity of *Rana catesbeiana* blood as nearly as possible. Frog Ringer's solution with glucose contained: 100 mM Na$^+$, 2.6 mM K$^+$, 99.6 mM Cl$^-$, 1 mM Mg$^{2+}$, 1 mM Ca$^{2+}$, 1 mM SO$_4^{2-}$, 2.5 mM HPO$_4^{2-}$, and 2 mM glucose, pH adjusted to 7.4. The glucose-free Ringer's solution used for tissue irrigation during dissection was the same, except for the omission of glucose and the addition of one extra mmol/L of NaCl to maintain the same solution osmolarity. The frog Ringer's solution used in perfused nerve experiments was oxygenated by heating the solution to 55° C. to displace any inert dissolved gases, and then the solution was bubbled with O$_2$ via a submerged gas dispersion tube at a rate of 2 L/min during the time required for the solution temperature to drop to 30° C. (>1 hr.). Further thermal equilibration to room temperature occurred without bubbling of the solution. The solution, thus oxygen-saturated at 30° C., contained ~1.15 µmol/mL of dissolved O$_2$. In the case of perfused *Rana pipiens* sciatic nerves undergoing 100 Hz electrical stimulation at 20° C., oxygen consumption by the nerve tissue was previously reported to increase to 1.15 µmol O$_2$/hr.·g wet weight. The typical fresh jumbo bullfrog sciatic nerve weighed ~15 mg/cm length. Assuming roughly similar O$_2$ consumption in *Rana catesbeiana* sciatic nerves with electrical activity, at a perfusate flow rate of 3 mL/hr., the oxygen supply (3.5 µmol O$_2$/hr.) would well exceed the tissue oxygen requirement of the perfused nerve (~0.07 µmol O$_2$/hr.) with the most vigorous electrical stimulation frequency employed in these experiments.

Electrophysiology Flow Cell for MRI

Figure 5:
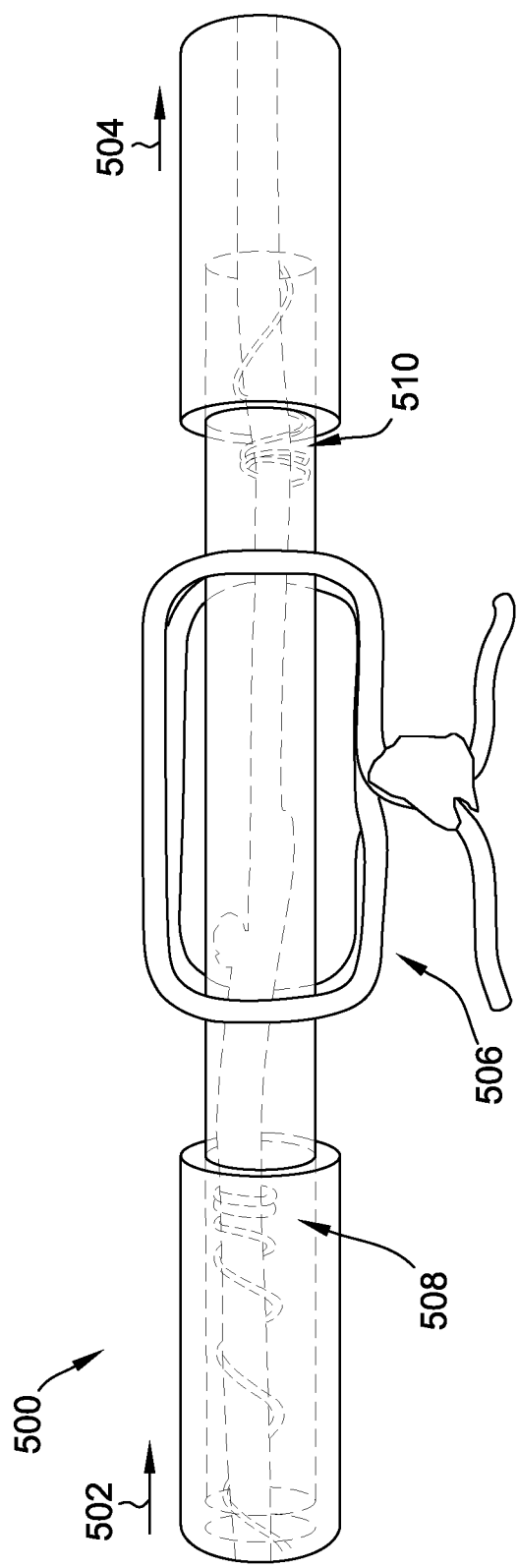
FIG. 5 is an image showing a close-up side view of the flow cell used for perfused nerve MRI studies with in-magnet electrophysiology recording (scale bar: 1 cm)

A perfusion flow cell was constructed from readily-available materials, holding the excised nerve immobilized at the two ends with retractable suction electrodes used for electrical stimulation and recording of the compound action potential. As illustrated in FIG. 5, the perfusion flow cell 500, the nerve was held in place at the two ends by a pair of suction electrodes, a stimulating electrode 508 and a recording electrode 510. The stimulating electrode 508 delivers electrical stimulation to the excised nerves and the recording electrode 510 records the compound action potential (CAP) from the perfused nerve. The perfusion flow cell 500 is shown with the single Helmholtz transmit/receive RF coil 506. The construction of the flow cell allows the nerve to be drawn into the perfusion apparatus without air bubbles, and the electrodes to be separated by a distance corresponding to the nerve's native length (estimated by measuring the length of the extracted nerve tissue under the straightening-force of gravity on its own weight, ~60 mg). Several minutes prior to drawing the nerve into the flow cell, fresh cuts were made at the ends of the nerve to remove the sutures. The cut nerve end would be expected to rapidly heal in $Ca^{2+}$-containing frog Ringer's solution. Once positioned into the flow cell, nerves were continuously perfused with oxygenated frog Ringer's solution at a rate of 3.0 mL/hr between an inflow end 502 and an outflow end 504. The nerve was allowed 1-2 hours of quiescent perfusion before the start of the MRI measurement series.

Electrical stimulation was delivered as 100 μs voltage pulses from a Pulse/Function Generator (model 33210A, Agilent Technologies, Santa Clara, Calif.) into an Analog Stimulus Isolation Unit (model 2200, A-M Systems, Sequim, Wash.). The DC stimulus/compound action potential (CAP) signals were carried to/from the magnet via shielded triax-cables. Suction electrodes were used for nerve stimulation and CAP recording. Placement of the recording amplifier grounding electrode in close proximity to the tip of the stimulating electrode was found to significantly reduce interference artifacts. The compound action potential signal was amplified (1000×) and filtered (high-pass cutoff: 160 Hz, low-pass cutoff: 20 kHz) via a home-built two-stage amplifier before passing to a digital oscilloscope (model TBS1052B, Tektronix, Beaverton, Oreg.) for signal averaging (128 averages). The signal-averaged CAP waveform was ported to a laptop pc and saved for offline processing and analysis.

For one set of the nerves studied (the diffusion fMRI studies carried out with 40-minute temporal resolution, described below), the electrical stimulation consisted of super-maximal stimulation delivered at 100 Hz frequency for a period of 40 minutes. In the other set of nerves, imaged with 20-minute temporal resolution, the nerves were stimulated first at 50 Hz×24 minutes, followed by a resting period of 3 hours, before undergoing a second round of electrical stimulus 100 Hz×24 minutes.

Figure 9A:
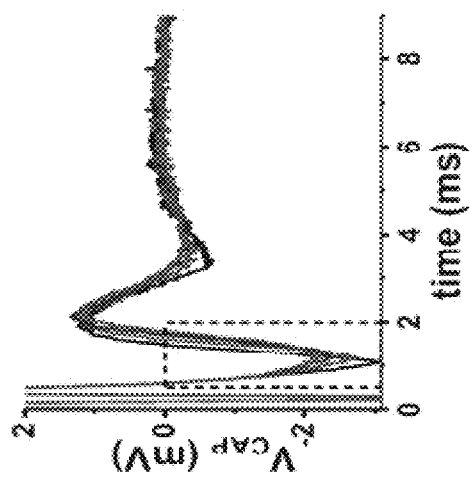
FIG. 9A is a graph showing individual CAP recordings at selected times during the stimulation period: black=1 min, red=10 min, blue=20 min, green=30 min)
Figure 9B:
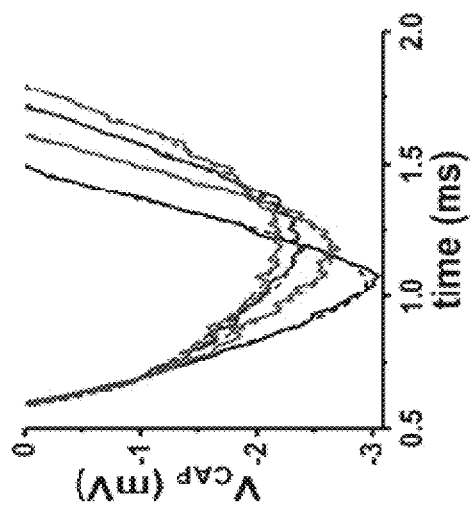
FIG. 9B is a zoomed-in view of the data from FIG. 9A shown in the dashed rectangle, in which solid curves denote the recorded data and dashed lines denote the model fit of the CAP.
Figure 9C:
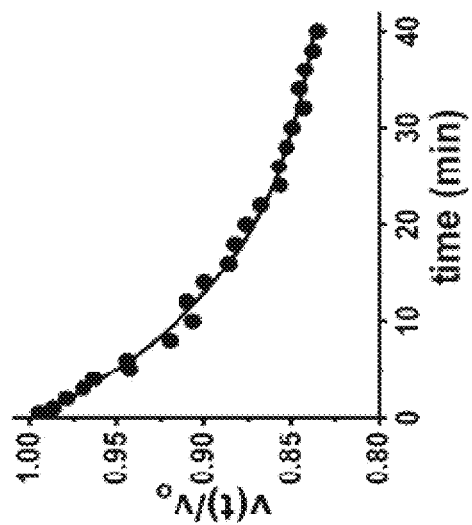
FIG. 9C is a graph summarizing the normalized conduction velocities plotted vs. time during the stimulation period.

FIG. 9A is a graph showing individual CAP recordings obtained at various times during repetitive electrical stimulation of the perfused bullfrog sciatic nerve at 100 Hz×40 min., and FIG. 9B is a zoomed-in graph of the data shown in the graph of FIG. 9A. The solid curves in FIGS. 9A and 9B show the recorded data, and the dashed lines show the model fit of the CAP. The CAP fitting was used to reduce variations in the estimated waveform peak amplitude and latency. FIG. 9C shows the normalized conduction velocities as a function of time during the stimulation period. The conduction velocities in FIG. 9C were normalized to remove the effect of conduction length. Because conduction velocities $v(t)=1/\tau_{latency}(t)$ and the initial conduction velocity $v_o=1/\tau_{latency,init}$, then $v(t)/v_o=\tau_{latency,init}/\tau_{latency}(t)$, where 1 represents the length of the perfused axon $\tau_{latency,init}$ represents the waveform latency of the axon prior to stimulation, and $\tau_{latency}(t)$ represents the waveform latency of the axon at various times during the stimulation. The broadening (decreased $V_{peak-peak}$) and slowing of the CAP are well represented by exponential kinetics. In the example depicted in FIG. 9C, the conduction velocity slowed to 84% of its initial value over the course of 40 min. The quantity $V_{CAP,40\,min}/V_{CAP,o}$ was used to describe slowing of the CAP conduction velocity during repetitive electrical stimulation in subsequent analyses.

Magnetic Resonance Imaging

MRI measurements were carried out in a 4.7 Tesla Agilent small-animal imaging system using home-built RF coils for signal transmit/receive.

Diffusion fMRI data was acquired with a multi-echo spin-echo diffusion-weighted imaging sequence. Acquisition parameters included TR=1.5 s, 3-echoes ($TE_1$=28.8 ms, $TE_2$=8.3 ms). A maximum diffusion-weighting b value of 3 ms/μm², was employed with a 25-direction diffusion-encoding scheme, and diffusion timings Δ=18 ms, δ=5 ms. A 1.5-mm slice thickness with a 0.5 mm gap between slices was used. The imaging field-of-view was 7×7 mm² with an acquisition matrix size of 32×32 (20 minutes per image) or 64×64 (40 minutes per image).

The RF coil setup was modified during the course of these experiments. An actively-decoupled transmit/receive coil pair was employed in earlier experiments (32×32) with a Helmholtz transmit coil and hemi-cylindrical surface receive coil for signal detection. For later experiments, with higher spatial resolution, a single transmit/receive coil was used (see FIG. 5). Generally, the more open nature of the single coil setup and one fewer cable made experimental setup less cumbersome. With the two-coil system, the image SNR in the processed $b_o$ (b=0 ms/μm²) images was 298±45 (mean±SD, 32×32 datasets) vs. 168±8 for the single-coil setup (64×64 datasets). Thus, the single-coil arrangement provided improved RF performance, since even though imaging voxels acquired in the 64×64 datasets (single coil) contained one-fourth as many spins as in the 32×32 datasets (two-coil arrangement), image signal-to-noise was only reduced by a factor of 2.

Carr-Purcell-Meiboom-Gill Multi-Echo Acquisition ($T_2$ Relaxation Spectra) was used to conduct a non-localized spectroscopy experiment. Trains of 4,096 echoes were acquired with a 1 ms inter-echo spacing. A repetition time of 20 s was used between the start of consecutive echo trains, and data from sixteen echo trains were averaged, thus the total measurement time was 5.3 minutes.

After setup in the magnet and verifying electrical activity of the perfused nerve, two baseline diffusion MRI scans were acquired, followed by a series of interleaved $T_2$ spectroscopy (5.3 min) and diffusion MRI (40 min) acquisitions. The second $T_2$ spectroscopy dataset was acquired just prior to commencement of repetitive electrical stimulation (100 Hz×40 min). One diffusion dataset was acquired during application of repetitive electrical stimulation. Upon completion of electrical stimulation, the interleaved $T_2$ and diffusion MRI acquisitions continued. Measurements terminated at 5 hours after the start of electrical stimulation.

MRI Data Analysis

For DBSI analysis, the raw k-space image data was multiplied by a Hamming window filter prior to zero-filling to a 128×128 matrix and denoising, with signal-averaging of the three acquired echoes. The resulting image data was then analyzed via the diffusion basis spectrum imaging (DBSI) package developed in-house and running in Matlab® 2015b (MathWorks, Natick, Mass.). The 25-direction diffusion-weighted signal (k: 1-25) was modeled as contributions from a basis set of anisotropic, cylindrically-symmetric diffusion tensors (i: 1–$N_{Aniso}$) with axial and radial diffusivities ($\lambda_{\parallel,i}$ and $\lambda_{\perp,i}$, respectively) and a spectrum of isotropic diffusion with amplitude f(D) at diffusivity D, as summarized in Equation [1].

$$S_k = \sum_{i=1}^{N_{Aniso}} f_i \cdot e^{-|\overrightarrow{b_k}| \cdot \lambda_{\perp,i}} \cdot e^{-|\overrightarrow{b_k}| \cdot (\lambda_{\parallel,i} - \lambda_{\perp,i}) \cdot \cos^2 \psi_{i,k}} +$$
$$\int_a^b f(D) \cdot e^{-|\overrightarrow{b_k}| \cdot D} \cdot dD$$
Eqn. [1]

Since the frog sciatic nerve was composed of a single, coherent axonal fiber bundle (i.e., no crossing fibers), the anisotropic modeling was limited to a single anisotropic tensor ($N_{Aniso}=1$), referred to as the fiber component ($f_{fiber}$). The isotropic spectral components were differentiated based upon diffusivity and denoted as restricted, ($0 < D_R \leq 0.3$ µm²/ms), hindered, ($0.3 < D_H \leq 2.0$ µm²/ms), or free ($D > 2.0$ µm²/ms).

Voxel-wise prescriptions of regions of interest (ROIs) for inclusion in diffusion MRI metric measurement for a given nerve at a given imaging time-point were based solely on the DBSI $f_{fiber}$ parameter map. Contiguous imaging voxels within each slice that satisfied the cutoff $f_{fiber} \geq 0.67$ were included in the nerve ROI. The nerve ROIs, prescribed in this manner and outlined using ITK-Snap software [ITK-SNAP, version 3.6.0, University of Pennsylvania] were saved and the average diffusion parameter values in the nerve ROI for each slice were extracted from the DTI and DBSI parameter image maps using an in-house script running in Python™ 2.7 (python.org).

DTI analysis of the same 25-direction diffusion-weighted imaging data sets was performed using existing methods known in the art.

To perform the $T_2$ spectral analysis, the CPMG echo data was decomposed into $T_2$ spectral components via non-negative least square fitting (NNLS) with a first-derivative smoothing term. In this approach, echo-decay data was assumed to be described by the form Equation [2]:

$$y_i = \sum_{j=1}^{M} s_j \cdot e^{-t_i T_{2,j}}; i = 1, 2, \ldots, N$$
Eqn. [2]

For the $T_2$ spectral analysis, N=4,068 echoes were used ($t_i$: 8-4,076 ms), and the spectrum was calculated as the set of amplitudes ($s_j$) at M=1,001 log-spaced $T_2$ grid points ($T_{2,j}$: 2-5000 ms), minimizing the least-squares misfit subject to the first-derivative smoothing constraint. The extent of smoothing employed for each dataset [i.e., the coefficient µ] was determined based upon the F-statistic for the sum of squares of the data/model misfit as compared to the misfit with no smoothing term applied (µ=0). The value of µ employed for the final accepted $T_2$ spectral modeling was the minimum value which resulted in p<0.10. This statistical-threshold was found to produce consistent results for estimated $T_2$ and component amplitudes amongst independent data sets, and values similar to those reported previously in the literature for ex vivo sciatic nerve of various frog species.

Results

Diffusion fMRI DTI Time-Course

Figure 6A:
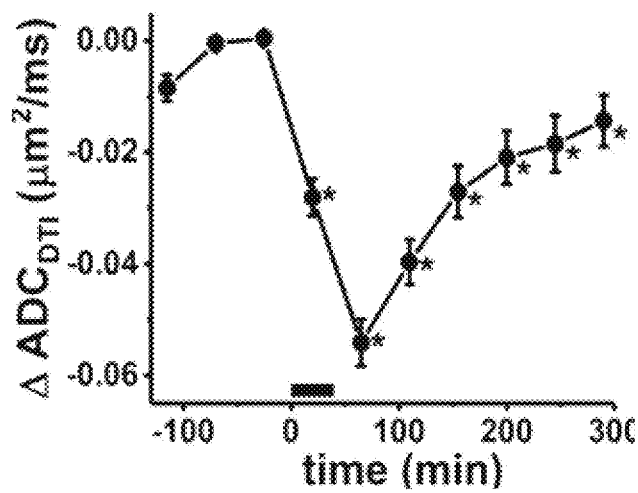
FIG. 6A is a graph showing the time-course change of the apparent diffusion coefficient ($\Delta ADC_{DTI}$), as compared to the average of the ADC measured at the two time-points prior to stimulation (n=6, error bars represent sample SEM)
Figure 6B:
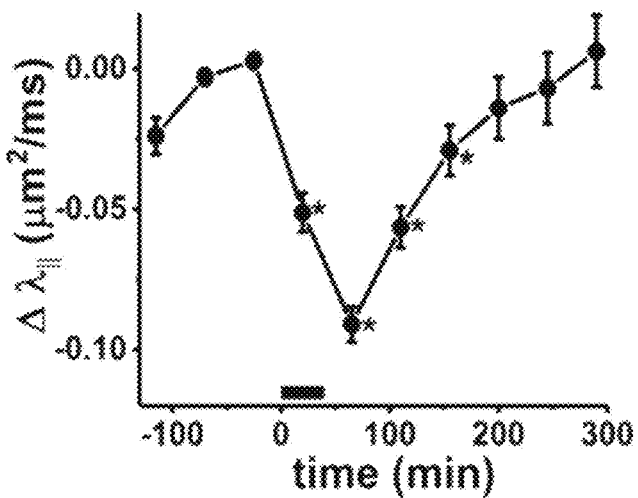
FIG. 6B is a graph showing the time-course change of axial diffusivity ($\Delta\lambda_\parallel$), as compared to the average of the $\lambda_\parallel$ measured at the two time-points prior to stimulation (n=6, error bars represent sample SEM)
Figure 6C:
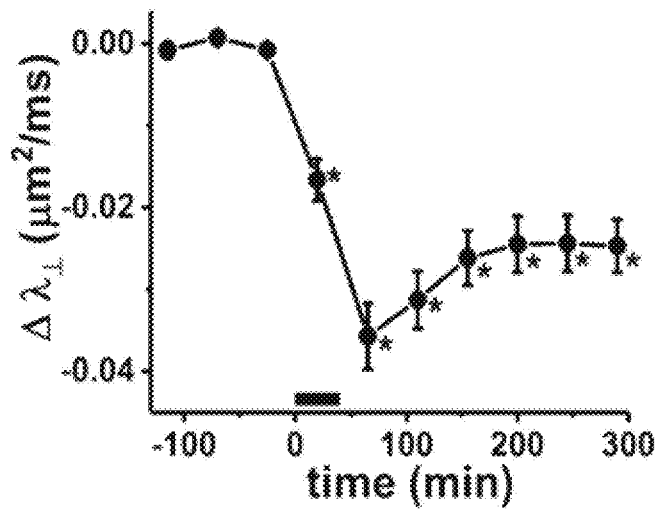
FIG. 6C is a graph showing the time-course change of radial diffusivity ($\Delta\lambda_\perp$), as compared to the average of the $\Delta\lambda_\perp$ measured at the two time-points prior to stimulation (n=6, error bars represent sample SEM)

FIGS. 6A, 6B, and 6C illustrate the time-course behavior of DTI parameters following a 40-minute period of stimulation at 100 Hz. The response of diffusion parallel to the axonal fibers exhibited a different response to the stimulation as compared to the response of diffusion perpendicular to the axonal fibers.

As illustrated in FIG. 6A, the mean apparent diffusion coefficient ($ADC_{DTI}$) showed a maximum decrease from baseline, $\Delta ADC_{DTI}=-0.054\pm0.004$ µm²/ms (mean±SEM, n=6), at the time-point immediately post-stimulus (FIG. 5A). This amounted to a 6.2% decrease, recovering towards baseline over the next several hours. In absolute terms, the pre-stimulus $ADC_{DTI}$ of $0.88\pm0.02$ µm²/ms (mean±SEM) fell to a nadir value of $0.83\pm0.02$ µm²/ms at the post-stimulation time-point. The period of electrical stimulation in FIG. 6A is depicted by a black bar along the x-axis from 0-40 minutes.

The principal eigenvalue of the DTI diffusion tensor represented axial diffusivity ($\lambda_\parallel$) of the diffusion ellipsoid. With the assumption of cylindrical symmetry, the radial diffusivity is taken as the average of the other two eigenvectors. Time-points which were statistically-significantly different than the pre-stimulus measurement, as determined via repeated-measures ANOVA/Tukey post-hoc testing, are indicated by an asterisk.

As illustrated in FIG. 6B, the recovery in $ADC_{DTI}$ was largely driven by the parallel diffusivity ($\lambda_\parallel$), which showed a large decrease ($\Delta\lambda_\parallel$) between the baseline and the post-stimulus time-points ($\Delta\lambda_\perp=-0.091\pm0.006$ µm²/ms, $-5.4\pm0.4\%$) and recovered fully to baseline over the course of 4 hours post-stimulation. The pre-stimulus $\lambda_\parallel$ of $1.68\pm0.06$ µm²/ms decreased to a minimum of $1.59\pm0.06$ µm²/ms before rebounding to $1.69\pm0.06$ µm²/ms at the last time-point. Time-points which were statistically-significantly different than the pre-stimulus measurement, as determined via repeated-measures ANOVA/Tukey post-hoc testing, are indicated by an asterisk.

As illustrated in FIG. 6C, the radial diffusivity $\lambda_\perp$ exhibited a smaller absolute drop $\Delta\lambda_\perp$ of $-0.036\pm0.004$ µm²/ms which was larger as a percentage of its initial value ($-7.4\pm0.8\%$). The radial diffusivity, which showed some tendency to recover over the course of 3 hours post-stimulation, appeared to finally stabilize at a level decreased from the pre-stimulus value. The initial $\lambda_\perp$ of $0.48\pm0.01$ µm²/ms decreased to $0.44\pm0.01$ µm²/ms, before achieving a post-stimulus plateau at $0.45\pm0.01$ µm²/ms. Time-points which were statistically-significantly different than the pre-stimulus measurement, as determined via repeated-measures ANOVA/Tukey post-hoc testing, are indicated by an asterisk.

While the decrease in $\lambda_\parallel$ appeared to be transient and recovered to baseline values, decreases in $\lambda_\perp$ and $ADC_{DTI}$ were more sustained over ~5 h post stimulation.

Figure 24A:
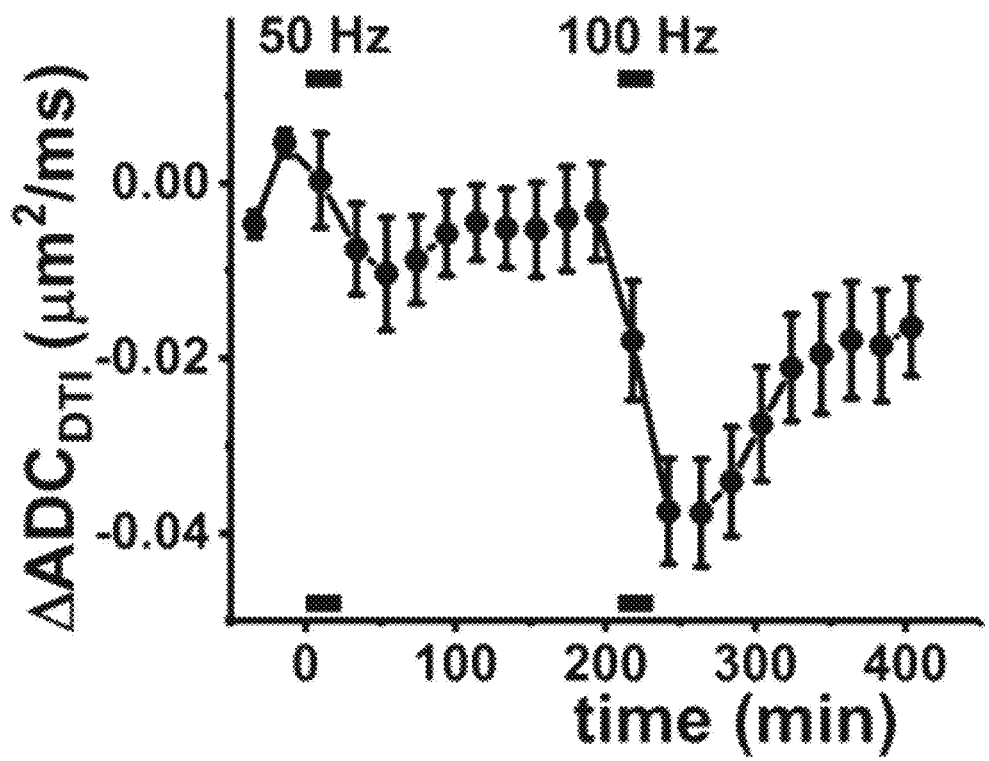
FIG. 24A is a graph showing the time-course change of the apparent diffusion coefficient ($\Delta ADC_{DTI}$), relative to the average of the ADC measured at the two time-points prior to two rounds of electrical stimulation (n=6, error bars represent sample SEM)
Figure 24B:
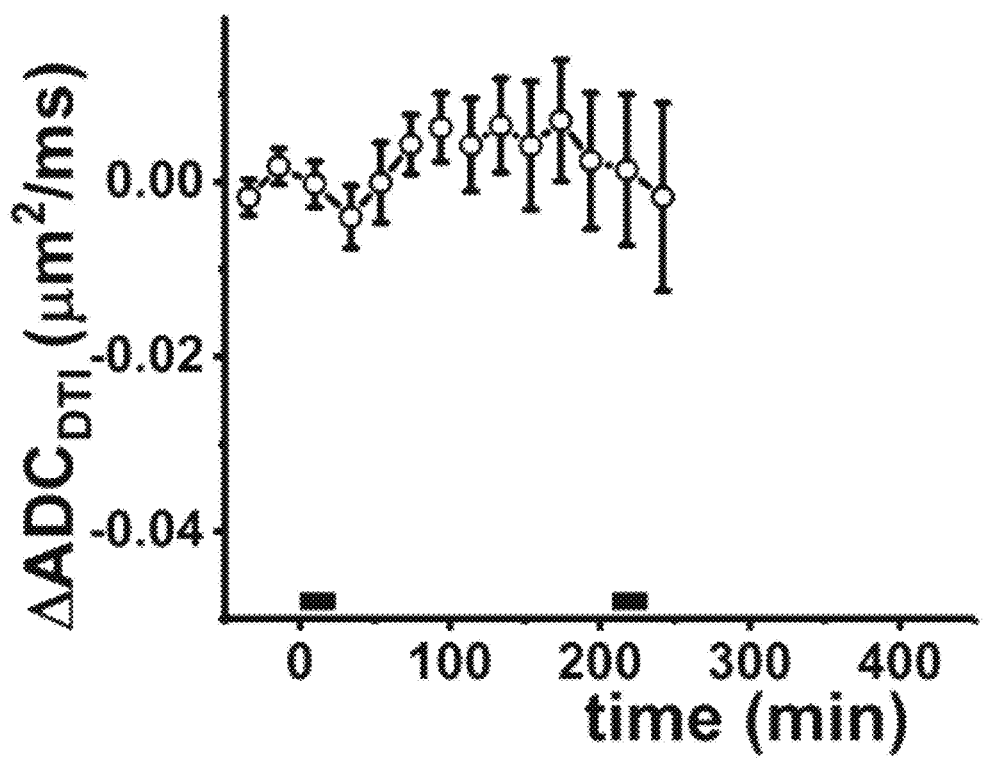
FIG. 24B is a graph showing the time-course change of the DTI apparent diffusion coefficient ($\Delta ADC_{DTI}$) for a perfusion-only treatment over a comparable time period to that of FIG. 24A.
Figure 24C:
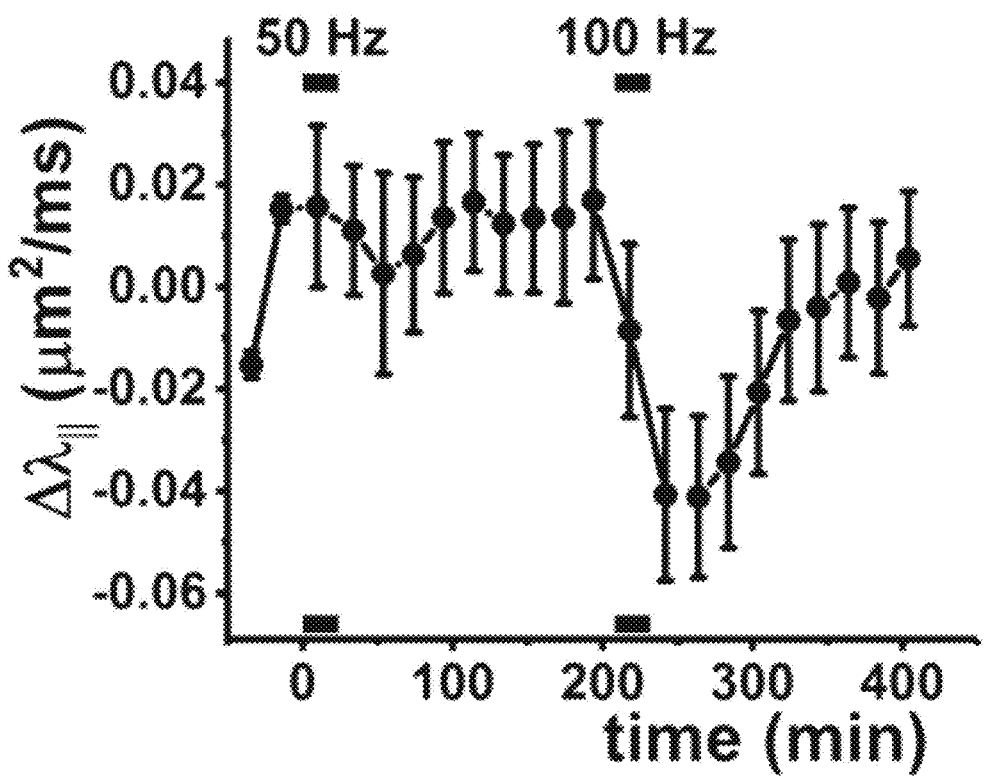
FIG. 24C is a graph showing the time-course change of the DTI axial diffusivity ($\Delta\lambda_\parallel$), relative to the average of the $\lambda_\parallel$ measured at the two time-points prior to two rounds of electrical stimulation (n=6, error bars represent sample SEM)
Figure 24D:
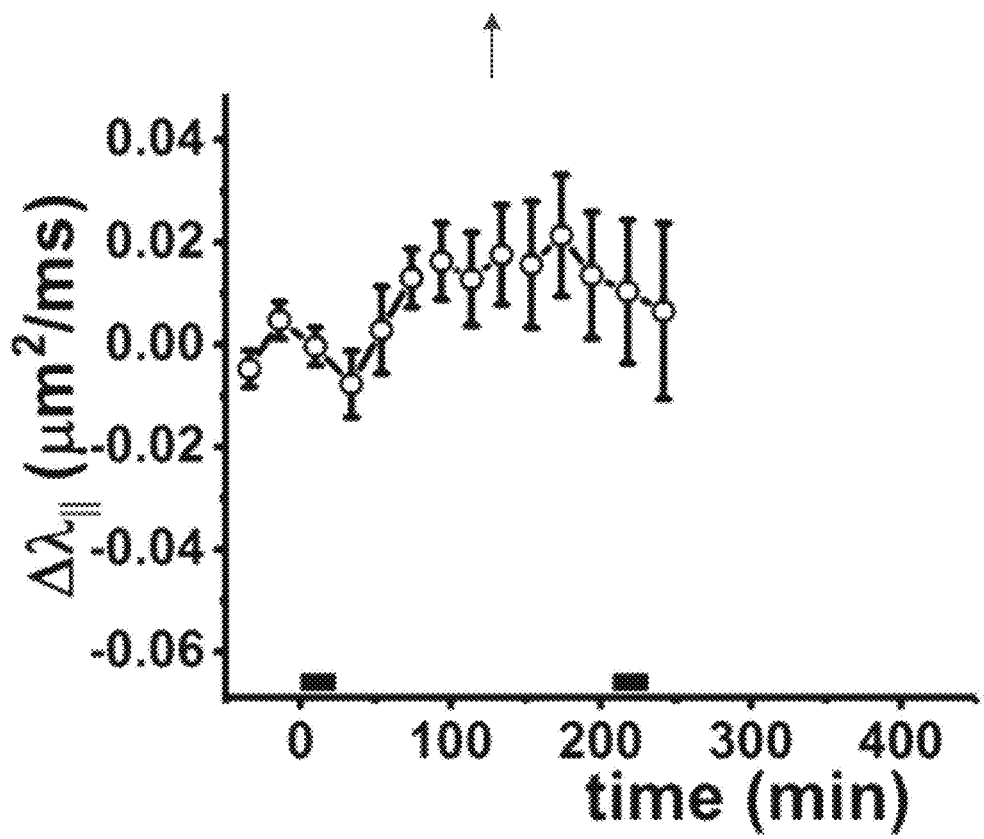
FIG. 24D is a graph showing the time-course change of the DTI axial diffusivity ($\Delta\lambda_\parallel$) for a perfusion-only treatment over a comparable time period to that of FIG. 24C.
Figure 24E:
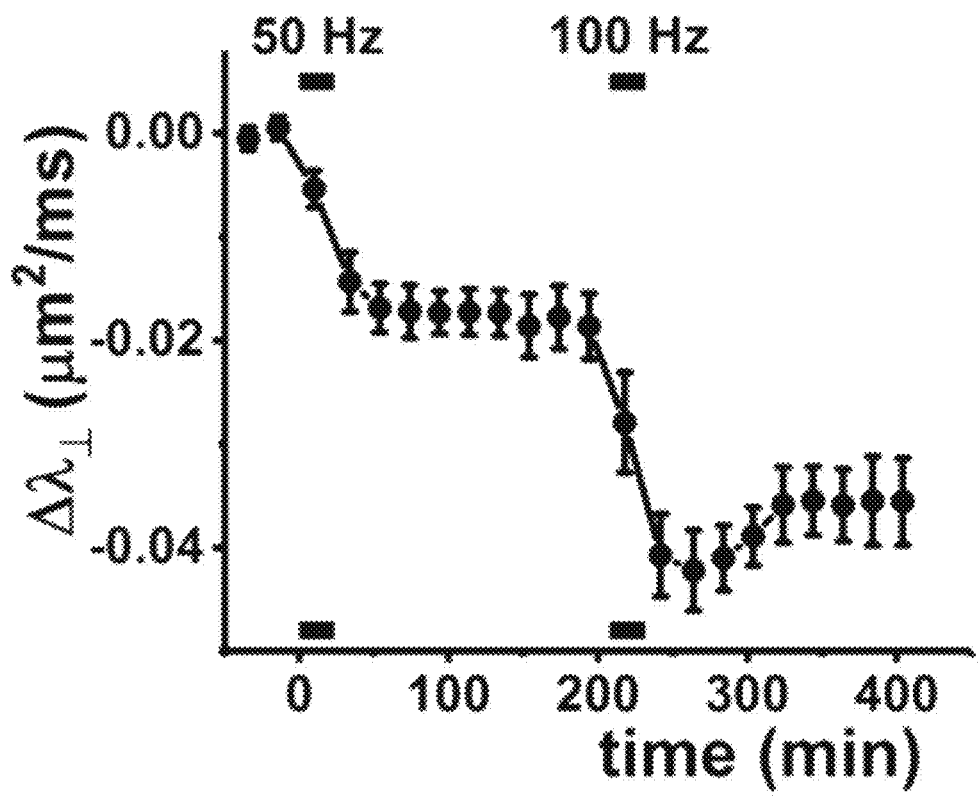
FIG. 24E is a graph showing the time-course change of the DTI radial diffusivity ($\Delta\lambda_\perp$), relative to the average of the $\lambda_\perp$ measured at the two time-points prior to two rounds of electrical stimulation (n=6, error bars represent sample SEM)
Figure 24F:
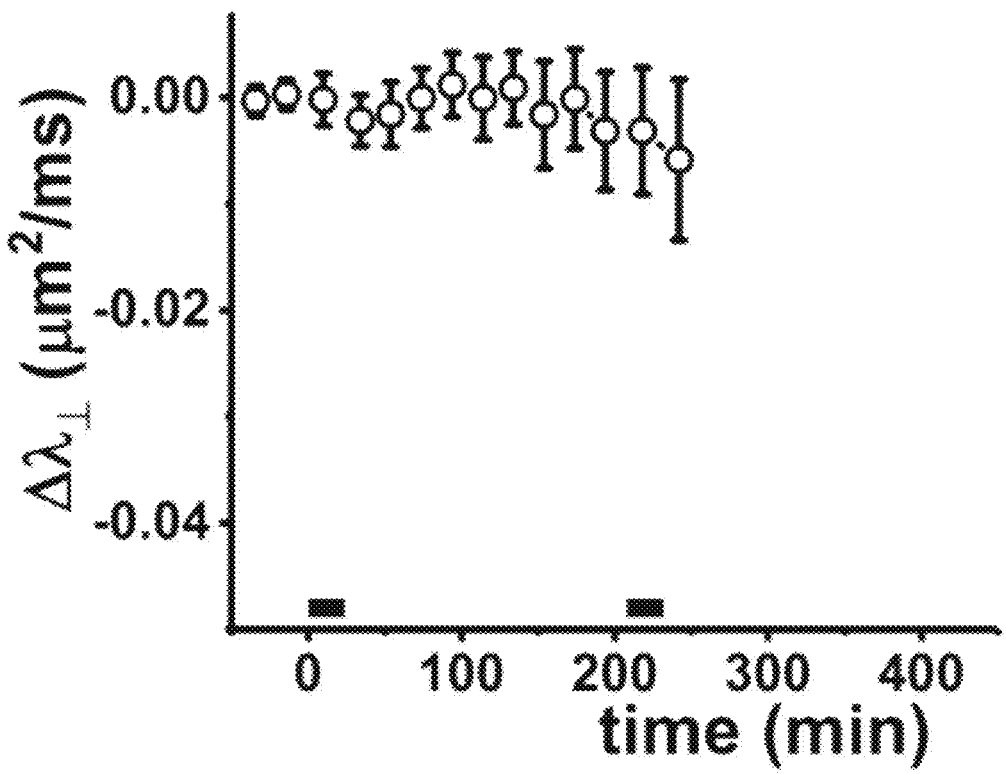
FIG. 24F is a graph showing the time-course change of the DTI radial diffusivity ($\Delta\|_\perp$) for a perfusion-only treatment over a comparable time period to that of FIG. 24E.
Figure 25A:
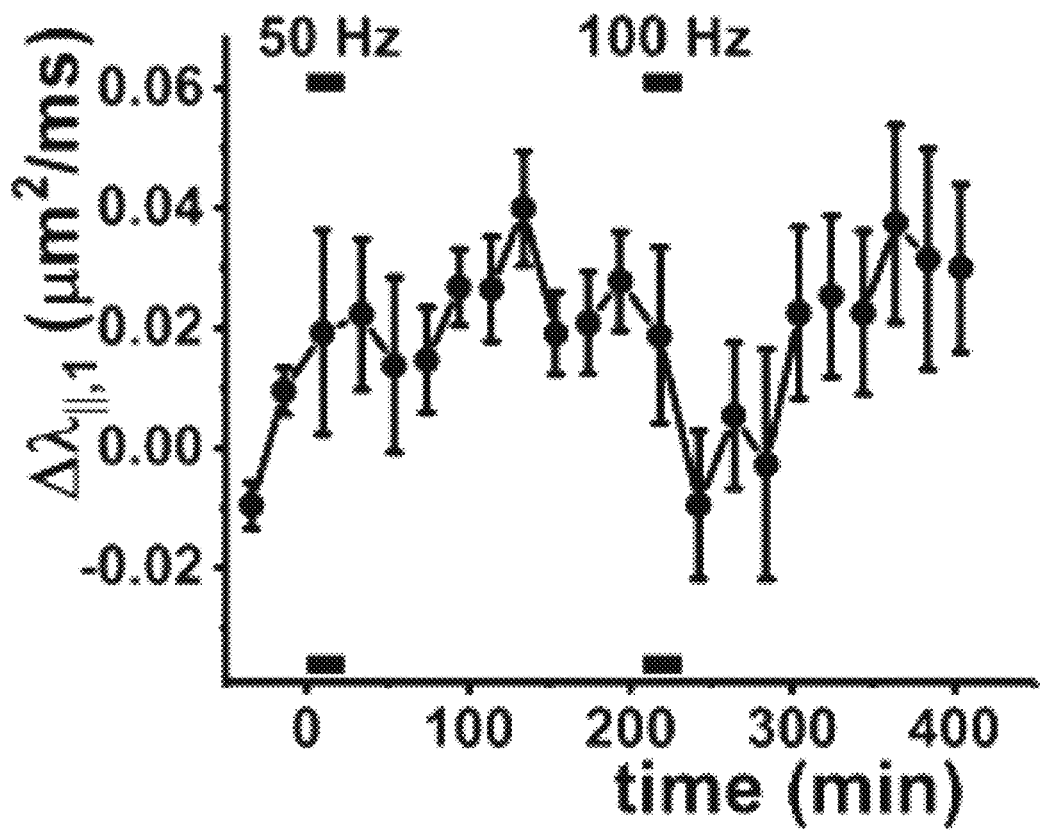
FIG. 25A is a graph showing the time-course change of the DBSI axial diffusivity ($\Delta\lambda_{\parallel,1}$), relative to the average of the $\lambda_{\parallel,1}$ measured at the two time-points prior to two rounds of electrical stimulation (n=6, error bars represent sample SEM)
Figure 25B:
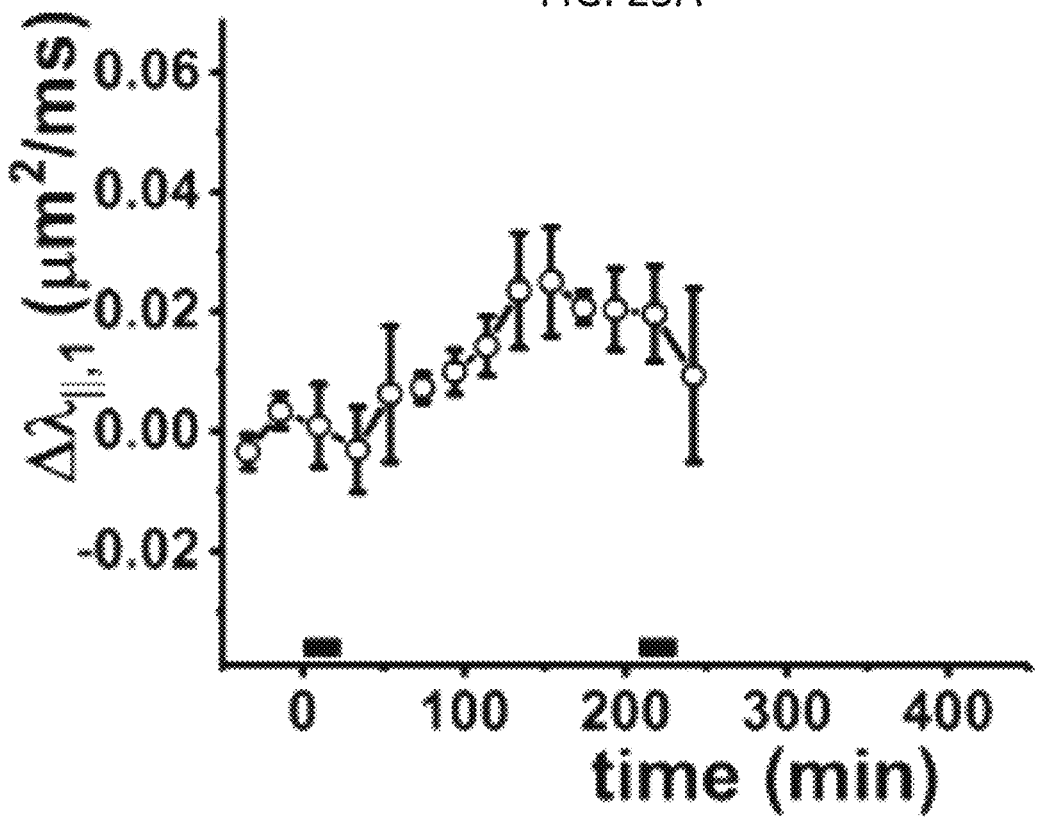
FIG. 25B is a graph showing the time-course change of the DBSI axial diffusivity ($\Delta\lambda_{\perp,1}$) for a perfusion-only treatment over a comparable time period to that of FIG. 25A.
Figure 25C:
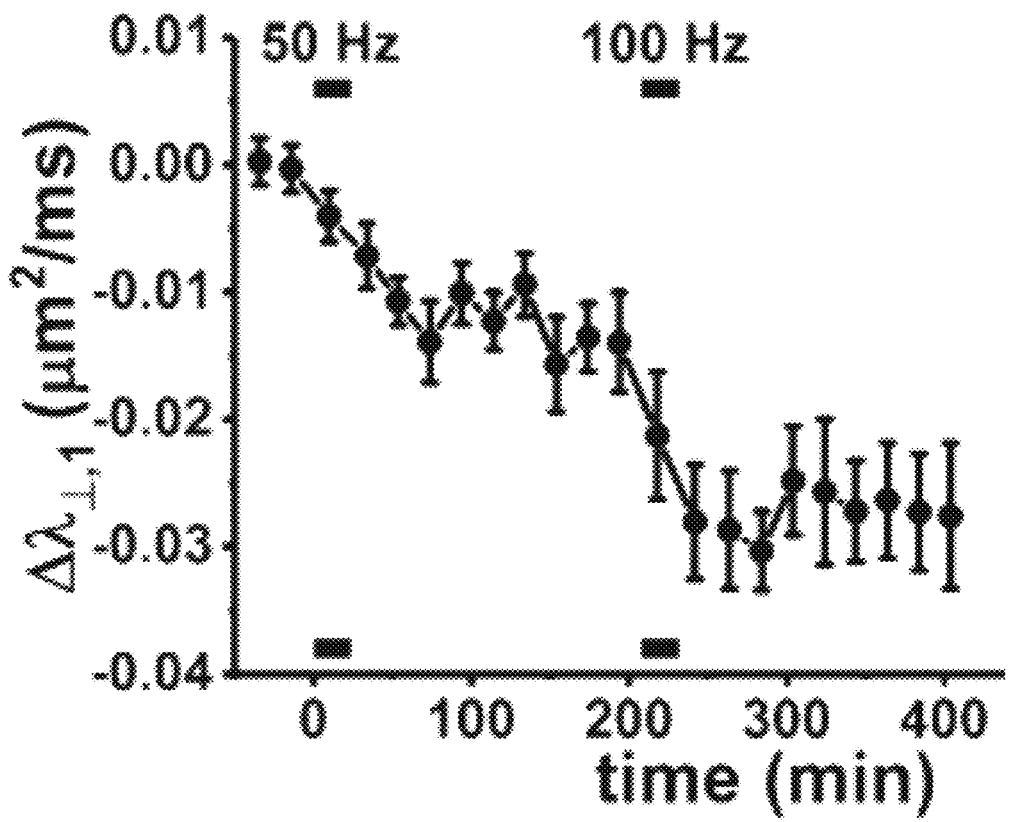
FIG. 25C is a graph showing the time-course change of DBSI radial diffusivity ($\Delta\lambda_{\perp,1}$), relative to the average of the $\lambda_{\perp,1}$ measured at the two time-points prior to two rounds of electrical stimulation (n=6, error bars represent sample SEM)
Figure 25D:
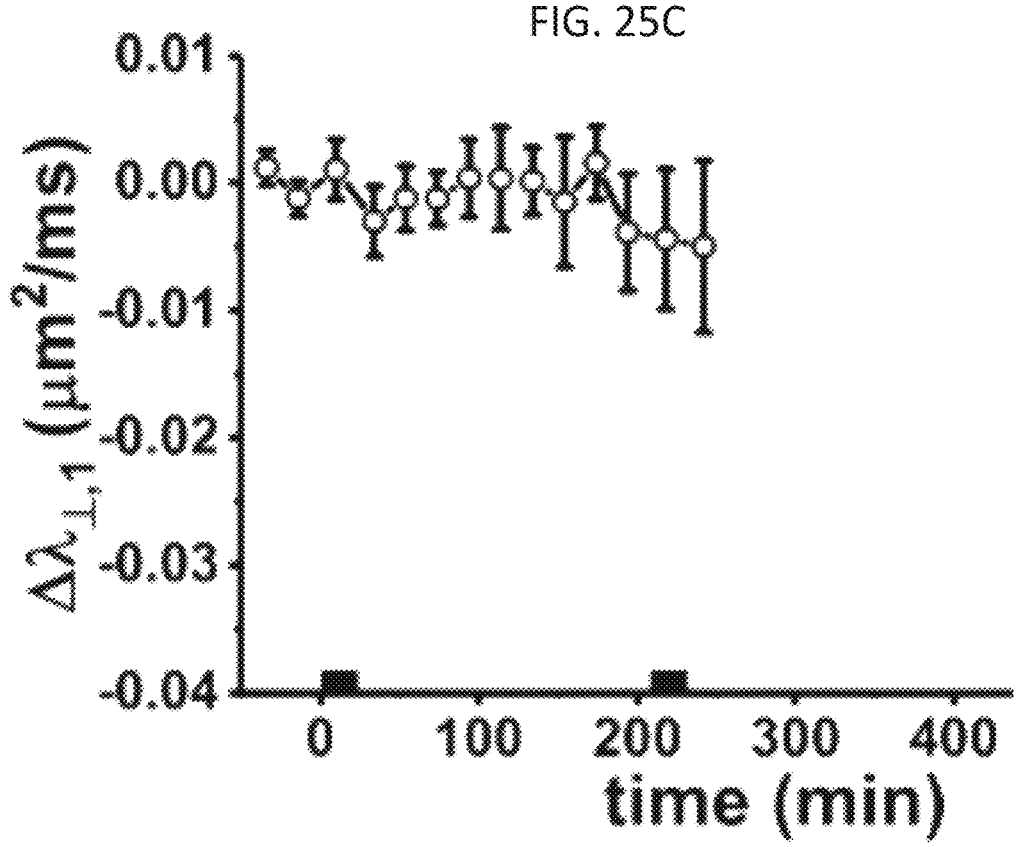
FIG. 25D is a graph showing the time-course change of the DBSI axial diffusivity ($\Delta\lambda_{\perp,1}$) for a perfusion-only treatment over a comparable time period to that of FIG. 25C.
Figure 25E:
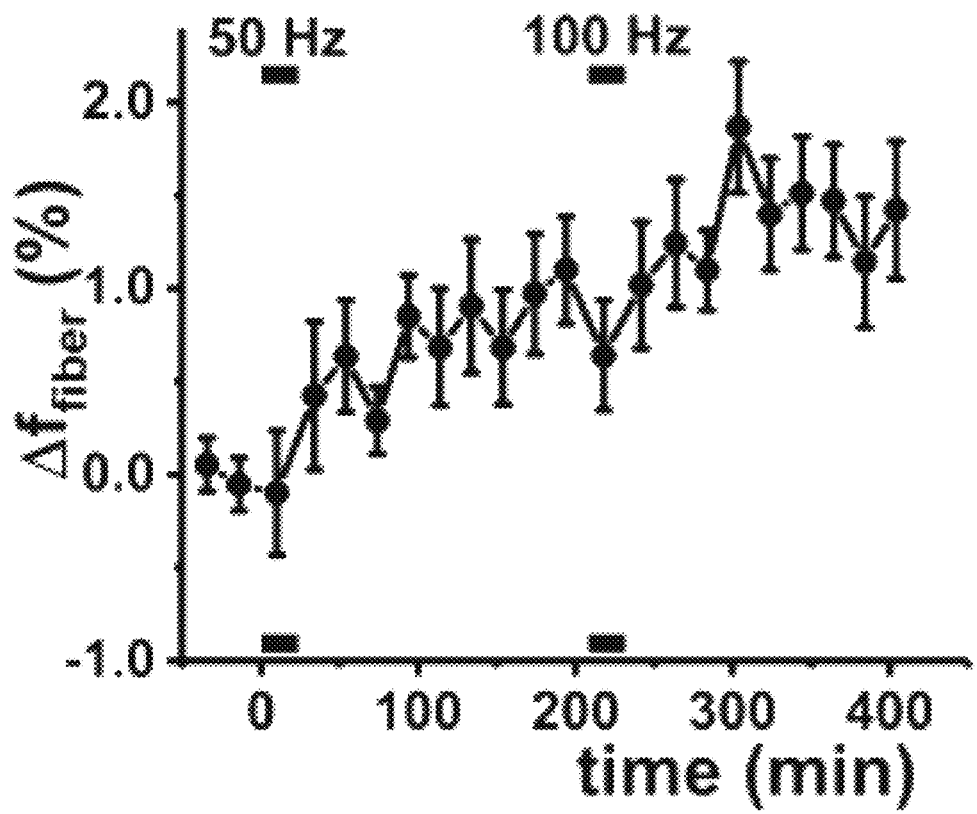
FIG. 25E is a graph showing the time-course change of the DBSI fiber fraction ($\Delta f_{fiber}$), relative to the average of the $f_{fiber}$ fiber measured at the two time-points prior to two rounds of electrical stimulation (n=6, error bars represent sample SEM)
Figure 25F:
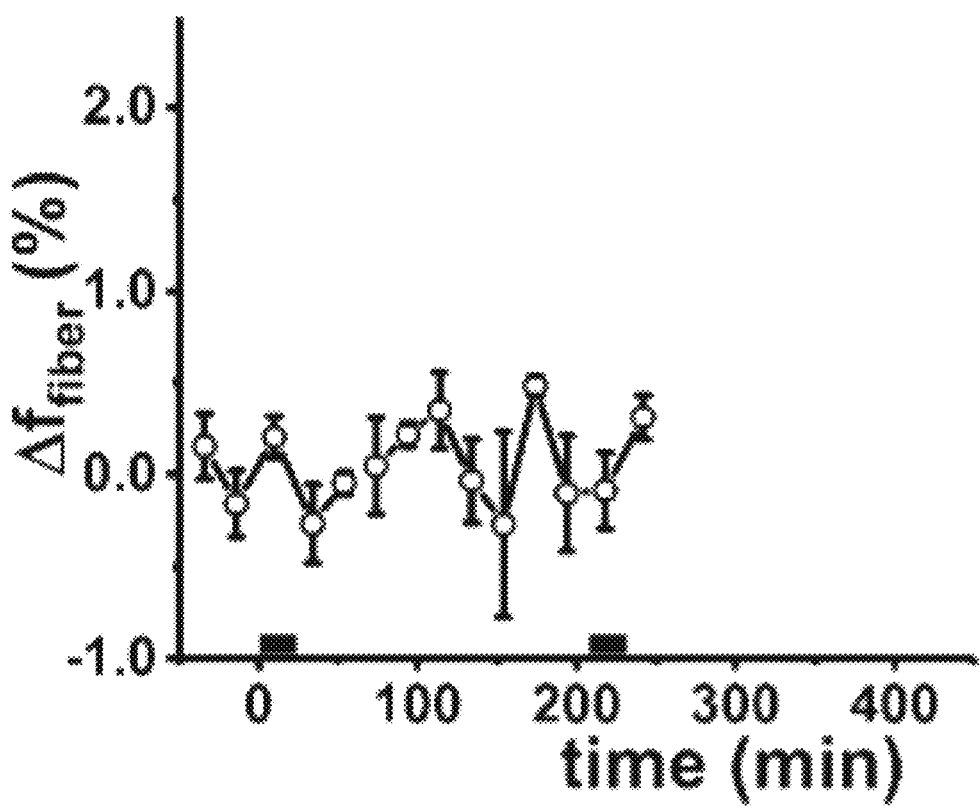
FIG. 25F is a graph showing the time-course change of the DBSI fiber fraction ($\Delta f_{fiber}$) for a perfusion-only treatment over a comparable time period to that of FIG. 25E.
Figure 25G:
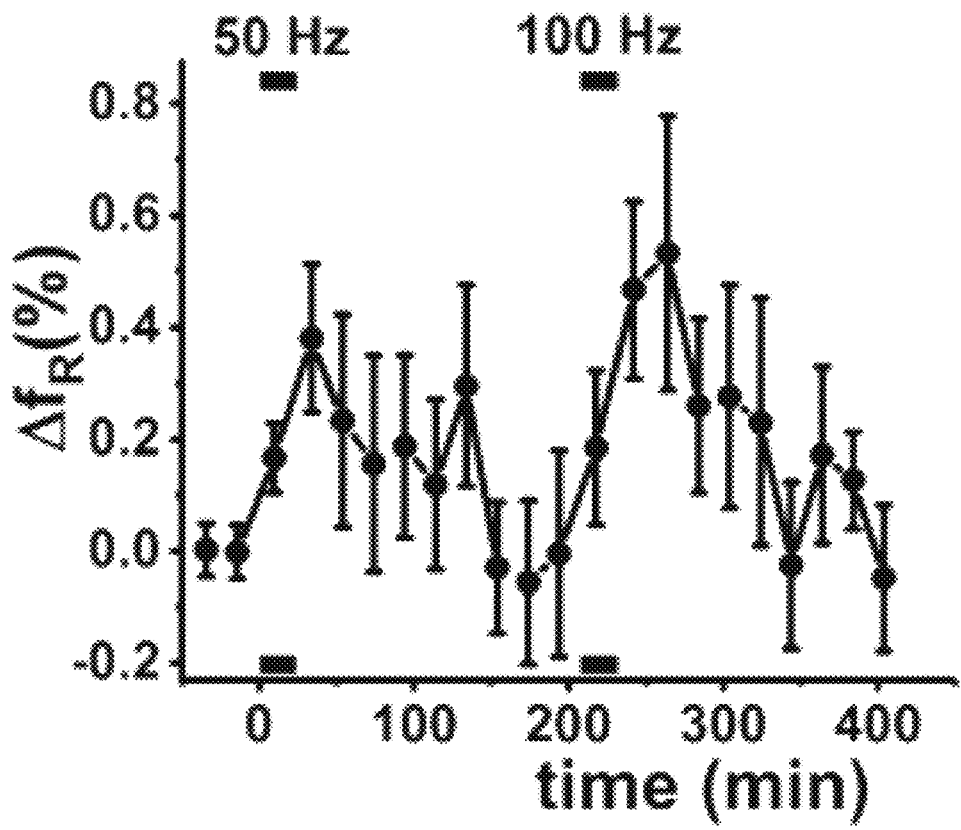
FIG. 25G is a graph showing the time-course change of the DBSI restricted component ($\Delta f_R$) of the isotropic ADC spectrum, relative to the average of the $f_R$ measured at the two time-points prior to two rounds of electrical stimulation (n=6, error bars represent sample SEM)
Figure 25H:
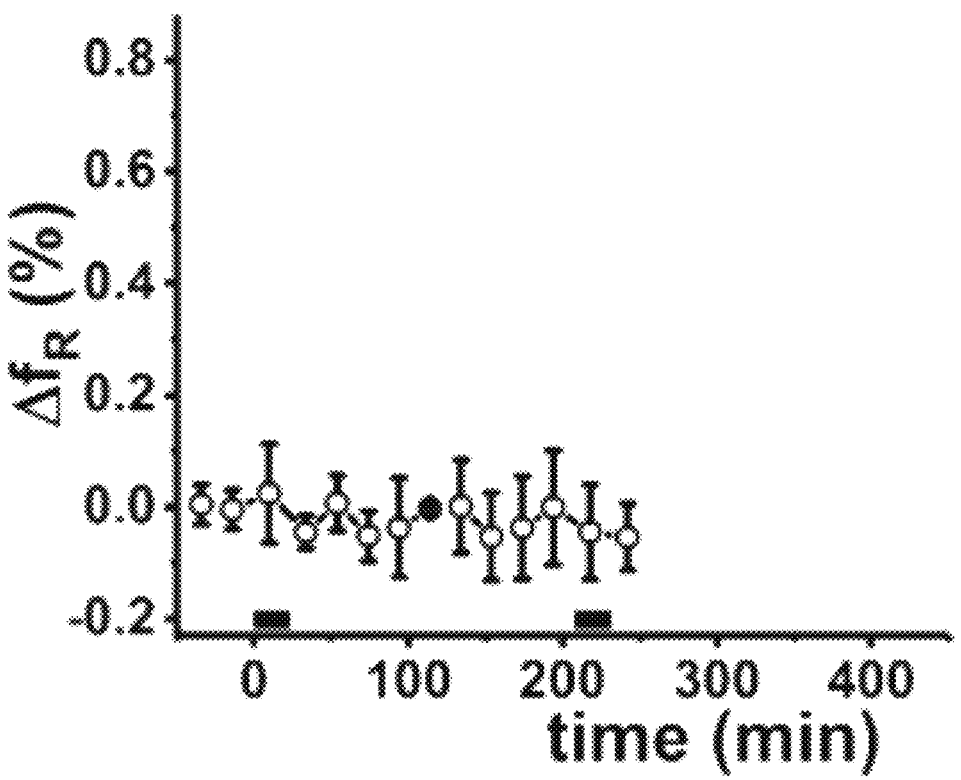
FIG. 25H is a graph showing the time-course change of the DBSI restricted component ($\Delta f_R$) for a perfusion-only treatment over a comparable time period to that of FIG. 25G.
Figure 25I:
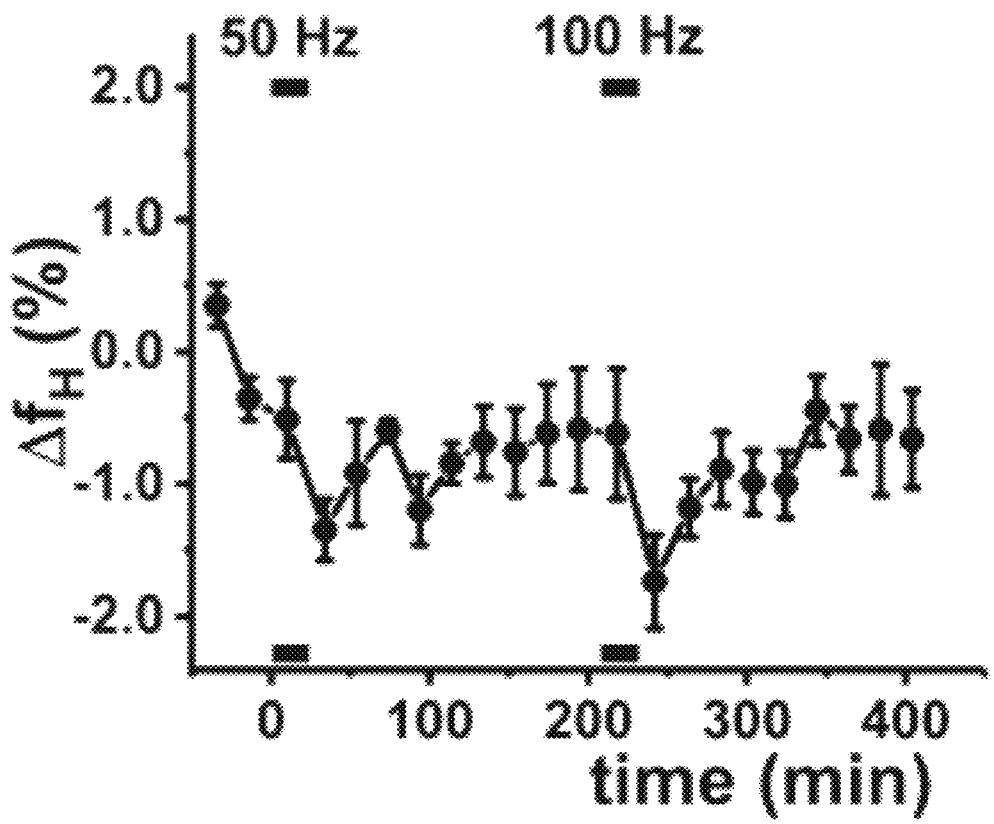
FIG. 25I is a graph showing the time-course change of the DBSI hindered component ($f_H$) of the isotropic ADC spectrum, relative to the average of the $f_H$ measured at the two time-points prior to two rounds of electrical stimulation (n=6, error bars represent sample SEM)
Figure 25J:
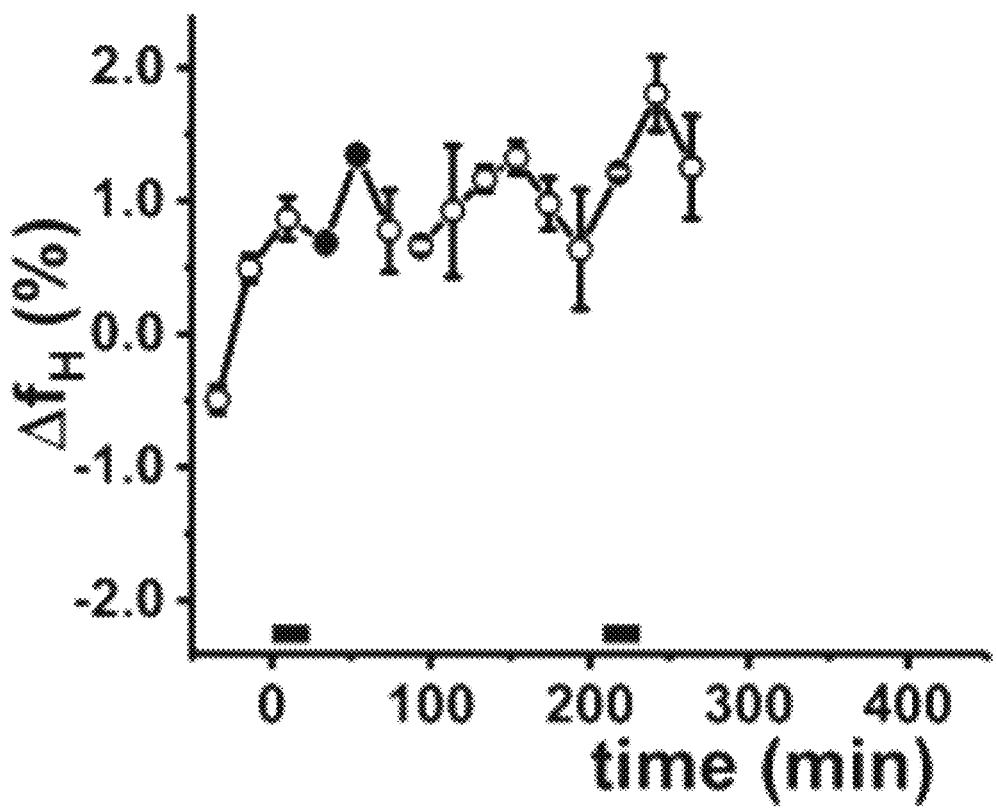
FIG. 25J is a graph showing the time-course change of the DBSI hindered component (fH) for a perfusion-only treatment over a comparable time period to that of FIG. 25A.

Similar DTI measurements of the perfused frog axon were derived from image data acquired with a 32×32 image matrix (20-minute temporal resolution). FIGS. 24A, 24C, and 24E depict DTI-model parameter results for perfused nerves (n=6, mean±sem) that underwent two rounds of electrical stimulation (24 minutes at 50 Hz and 24 minutes at 100 Hz) separated by a 3-hour recovery period. For comparison, the bottom row of panels (FIGS. 24B, 24D, and 24F) depict results for nerves (n=3, mean 4±sem) that underwent perfusion-only (no electrical stimulation) in a shorter time-course—ending at the time-point corresponding to the second post-stimulus time-point. Periods of electrical stimulation are depicted by the black bars in the top row. For reference, the corresponding times are also indicated in the perfusion-only figures.

Diffusion Functional DBSI Time-Course

The readouts on fiber-component axial ($\lambda_{\parallel,fiber}$) and radial ($\lambda_{\perp,fiber}$) diffusivities from DBSI were similar to those provided by DTI modeling (FIGS. 7E and 7F, respectively), with the DBSI fiber component ($f_{fiber}$) accounting for >70% of the total diffusion signal. FIGS. 7B, 7C, 7D, 7E, 7F, and 7G summarize changes in the various DBSI diffusion signal components shown in FIG. 7A ($f_{fiber}$=fiber fraction; $f_H$=Hindered isotropic diffusion fraction; $f_R$=Restricted isotropic diffusion fraction). All changes in DBSI diffusion components are presented as a percent of the total sciatic nerve signal. Time-points that were significantly different from the pre-stimulus values, based on a repeated-measures ANOVA/Tukey test, are indicated by an asterisk.

Figure 7B:
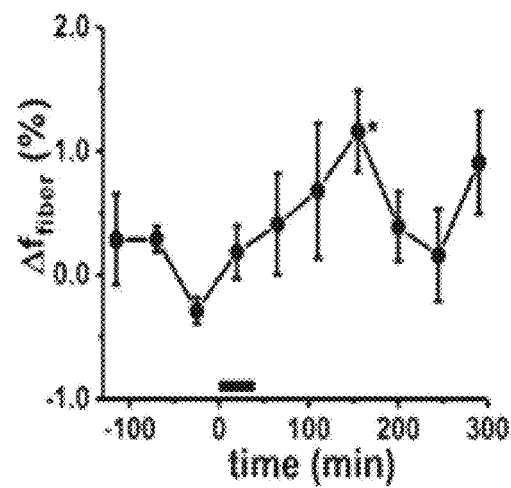
FIG. 7B is a graph showing time-course changes in DBSI fiber fraction ($\Delta f_{fiber}$) from initial value (n=6)

As illustrated in FIG. 7B, repetitive electrical stimulation resulted in a mild, non-statistically-significant increase in $f_{fiber}$, on the order of 1%. Fiber fraction exhibited an increase from an initial $f_{fiber,init}$ of 0.778±0.009 to a maximum of 0.789±0.008. This increase became statistically significant starting at the 4th time-point after the start of stimulation. This increase suggested a shift of 1.1% ($\Delta f_{fiber}$=1.1±0.3) into the fiber signal component of the DBSI model.

Figure 7C:
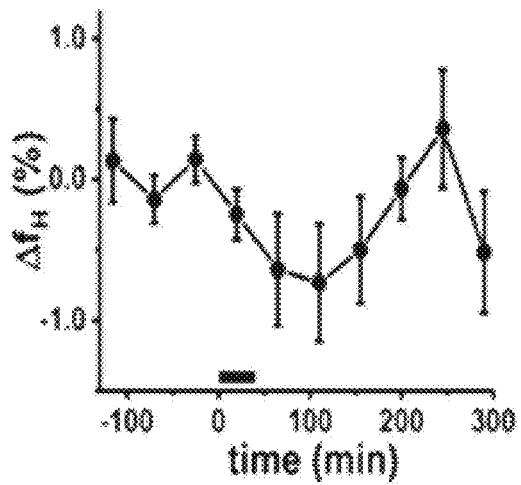
FIG. 7C is a graph showing time-course changes in DBSI hindered component ($f_H$) of the isotropic ADC spectrum from initial value (n=6)

As illustrated in FIG. 7C, a decrease in the hindered fraction, $f_H$, was observed. The hindered component ($f_H$) of the isotropic ADC spectrum indicated a maximum post-stimulus shift of 0.7±0.3% of tissue water out of the hindered isotropic diffusion component.

Figure 7D:
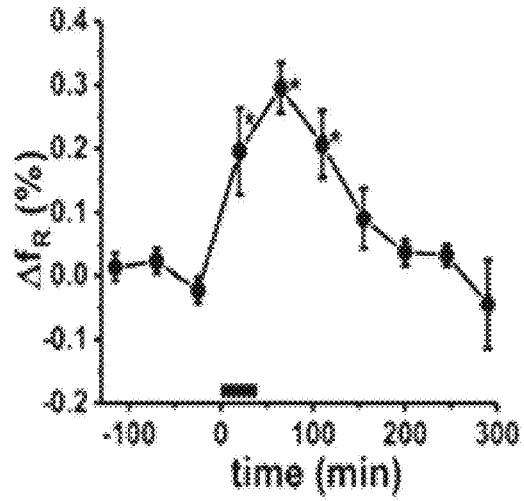
FIG. 7D is a graph showing time-course changes in DBSI restricted component ($f_R$) of the isotropic ADC spectrum from initial value (n=6)
Figure 7E:
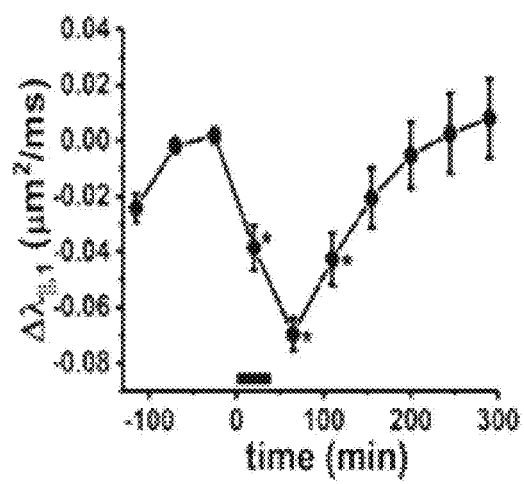
FIG. 7E is a graph showing time-course changes in DBSI axial diffusivity ($\lambda_{\parallel,fiber}$) from initial value (n=6)
Figure 7F:
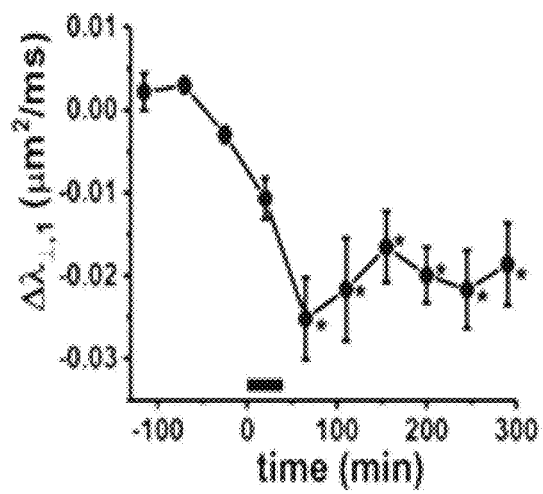
FIG. 7F is a graph showing time-course changes in DBSI radial diffusivity ($\lambda_{\perp,fiber}$) from initial value (n=6)

As illustrated in FIG. 7D, a small portion of the water in the perfused-nerve ($\Delta f_R$) (0.30±0.03% of the total isotropic diffusion), transiently shifted into a compartment with restricted isotropic diffusion. Pre-stimulation, the restricted diffusion component accounted for 0.2±0.1% of the total signal in the nerve. Relative to baseline $f_R$ levels, $f_R$ transiently increased by 230%.

Figure 7G:
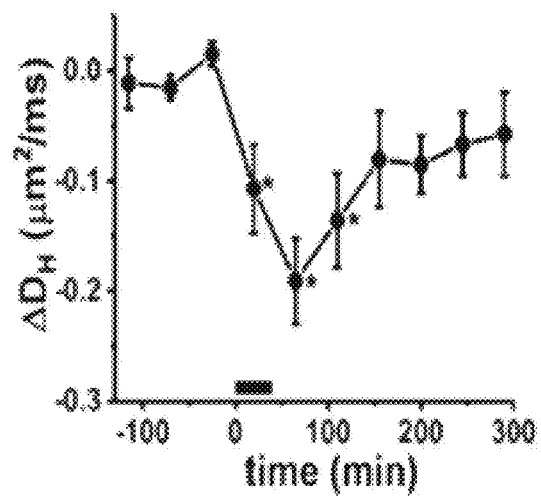
FIG. 7G is a graph showing time-course changes in DBSI hindered diffusivity ($\Delta D_H$) from initial value (n=6)

As illustrated in FIG. 7G, a decrease in the hindered component's apparent diffusivity, $D_H$ was observed. Post-stimulus, =–0.19±0.04 μm²/ms, from an initial pre-stimulus $D_H$ of 1.30±0.06 μm²/ms. Time-points that are statistically-significantly different from the pre-stimulus value via repeated-measures ANOVA/Tukey test are indicated by an asterisk.

Figure 7H:
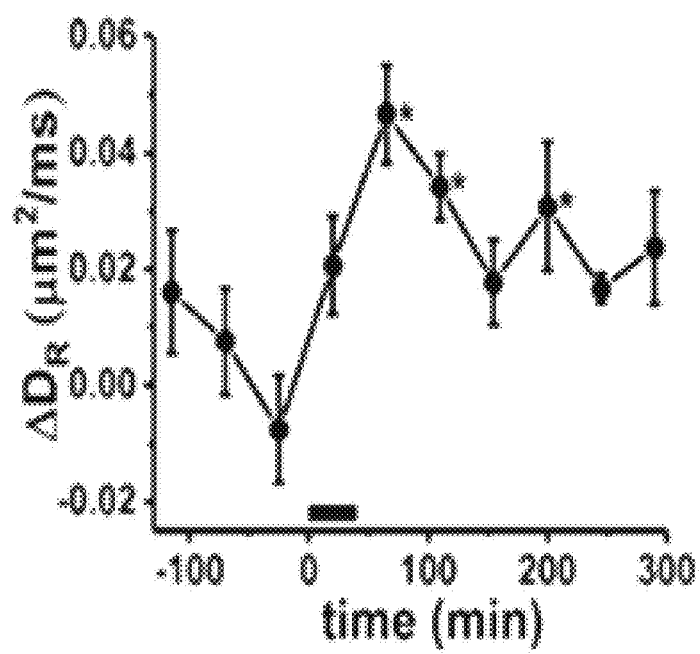
FIG. 7H is a graph showing time-course changes in DBSI restricted diffusivity ($D_R$) from initial value (n=6)

As illustrated in FIG. 7H, a transient increase in the diffusion signal component associated with the most restricted diffusivity ($D_R$<0.3 μm²/ms) was observed. In all cases studied here, the restricted diffusion fraction ($f_R$) accounted for less than 1% of the total sciatic nerve water. On average, 0.3% of the water shifted into this restricted DBSI signal component after 40 min×100 Hz electrical stimulation. The pre-stimulus $D_R$ increased from 0.11±0.02 μm²/ms to 0.15±0.02 μm²/ms. The observation that $D_R$ appeared to remain elevated while $f_R$ returned nearly to baseline suggested that the restricted diffusion compartment was representative of the largest sub-myelinic vacuoles that were the least transient in nature.

While some of the DBSI signal components exhibited only transient changes ($f_R$, $D_H$, $D_R$, and $\lambda_{\parallel,1}$), the induced change in DBSI fiber radial diffusivity ($\lambda_{\perp,1}$) was sustained over the post stimulus observation period.

$T_2$ Spectral Changes

To determine whether dynamic $T_2$ spectroscopy could non-invasively detect structural changes accompanying repetitive electrical activity, dynamic $T_2$ spectra were successfully acquired from five perfused nerves.

For the $T_2$ spectral analysis, N=4,068 echoes were used ($t_i$: 8-4,076 ms), and the spectrum was calculated as the set of amplitudes ($s_j$) at M=1,001 log-spaced $T_2$ grid points ($T_{2,j}$: 2-5000 ms), minimizing the least-squares misfit subject to the first-derivative smoothing constraint. The extent of smoothing employed for each dataset [the coefficient μ] was determined based upon the F-statistic for the sum of squares of the data/model misfit as compared to the misfit with no smoothing term applied (μ=0). The value of μ employed for the final accepted $T_2$ spectral modeling was the minimum value which resulted in p<0.10. This statistical-threshold was found to produce consistent results for estimated $T_2$ and component amplitudes amongst independent data sets, and values similar to those reported previously in the literature for ex vivo sciatic nerve of various frog species.

Figure 10A:
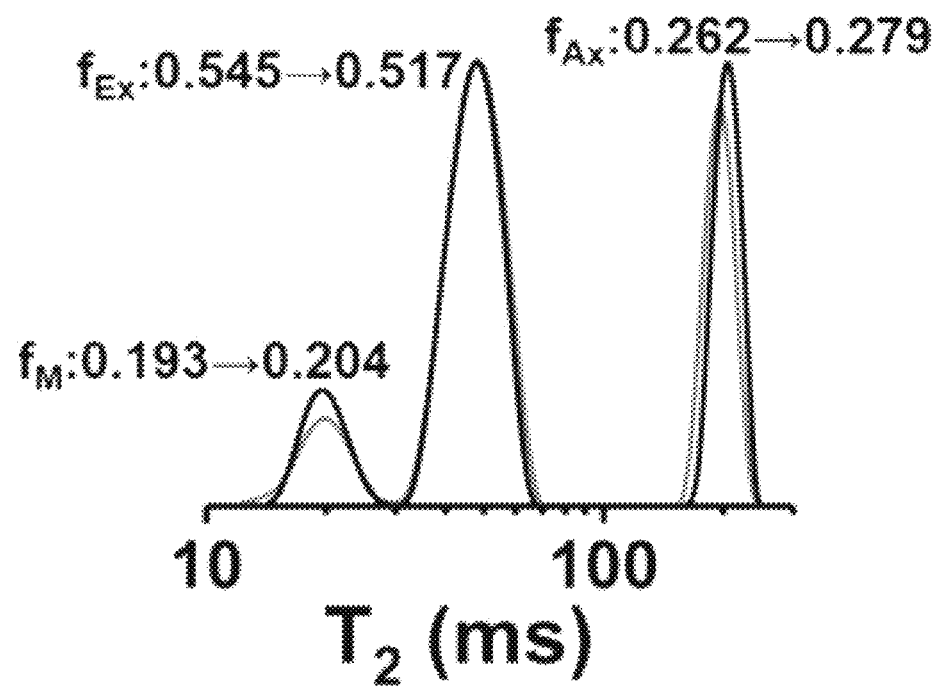
FIG. 10A is a graph showing an example of pre-(gray) and post-stimulation (black) $T_2$ spectra acquired from a perfused frog sciatic nerve.

The pre-stimulus $T_2$-spectroscopy-based signal fractions [$f_M$=0.173±0.009 (myelin), $f_{Ex}$=0.568±0.011 (extracellular), $f_{Ax}$=0.259±0.011 (axonal), mean±SEM] were in reasonably good agreement with existing literature reports for in vivo and ex vivo sciatic nerves of various frog species. FIG. 10A shows pre- and post-stimulation $T_2$ spectra for a perfused bullfrog sciatic nerve. The cpmg echo-trains acquisitions (4,096 echoes spaced by 1 ms, TR=20 s, sixteen averages, 5 min and 20 sec per measurement) were interleaved between the diffusion fMRI time-points. $T_2$-based signal fractions $f_M$ (myelin), $f_{Ex}$ (extracellular), and $f_{Ax}$ (axonal).

Figure 10B:
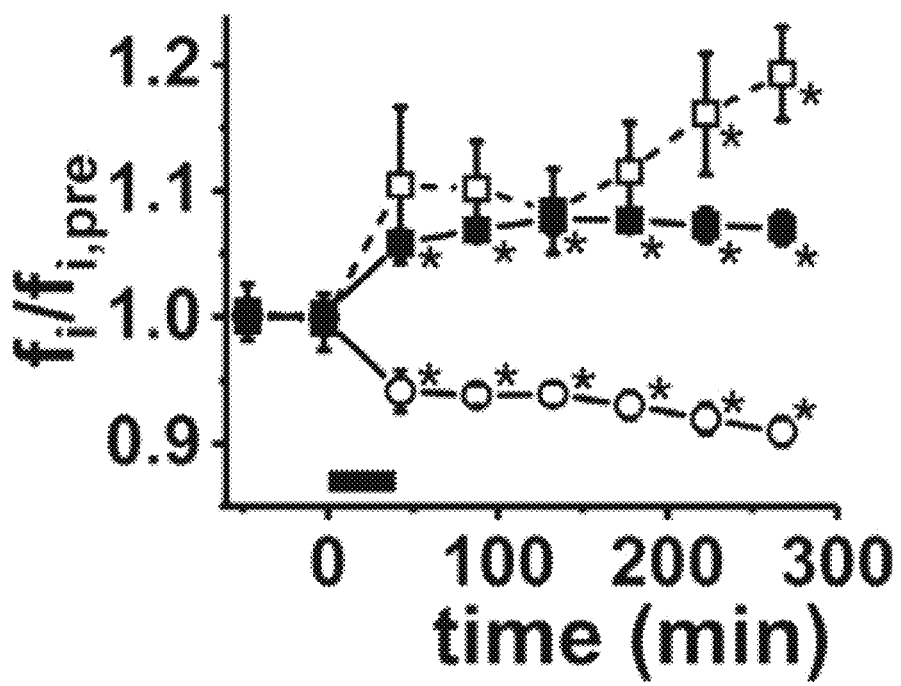
FIG. 10B is a graph showing the group-averaged evolution of the $T_2$ signal components vs. time revealed by dynamic $T_2$ spectroscopy (n=5, error bars represent SEM)

In FIG. 10B, the nerve $T_2$ signal fractions, $f_i$, were normalized such that their pre-stimulus average is 1, so the dynamics of the three signal components can be displayed in a single plot ($f_M/f_{M,pre}$: open squares, $f_{Ax}/f_{Ax,pre}$: closed circles, $f_{Ex}/f_{Ex,pre}$: open circles). The period of applied electrical stimulation (100 Hz×40 min) is represented by the black bar from 0 to 40 min along the x-axis in FIG. 10B. Statistically-significant differences from the pre-stimulus measurement (repeated-measures ANOVA/Tukey post-hoc testing) are indicated by asterisks. A general feature in the $T_2$ spectral measurements, as illustrated in FIG. 10B, is that sustained electrical stimulation produces an increase in the myelin-water fraction (+8.7±1.2%) and the intra-axonal water fraction (+7.3±1.0%) with a shrinkage of the extracellular water fraction (–5.9±0.7%). For the $T_2$ time-course analysis, only 5 of the 6 nerves were included, one of the datasets exhibiting 60 Hz interference (signal oscillations) superimposed upon the $T_2$ decay envelope.

Diffusion fMRI Dose-Response

To assess diffusion fMRI responses to stimuli of reduced duration and/or frequency of applied super-maximal electrical stimulation, the following experiments were conducted.

Figure 11A:
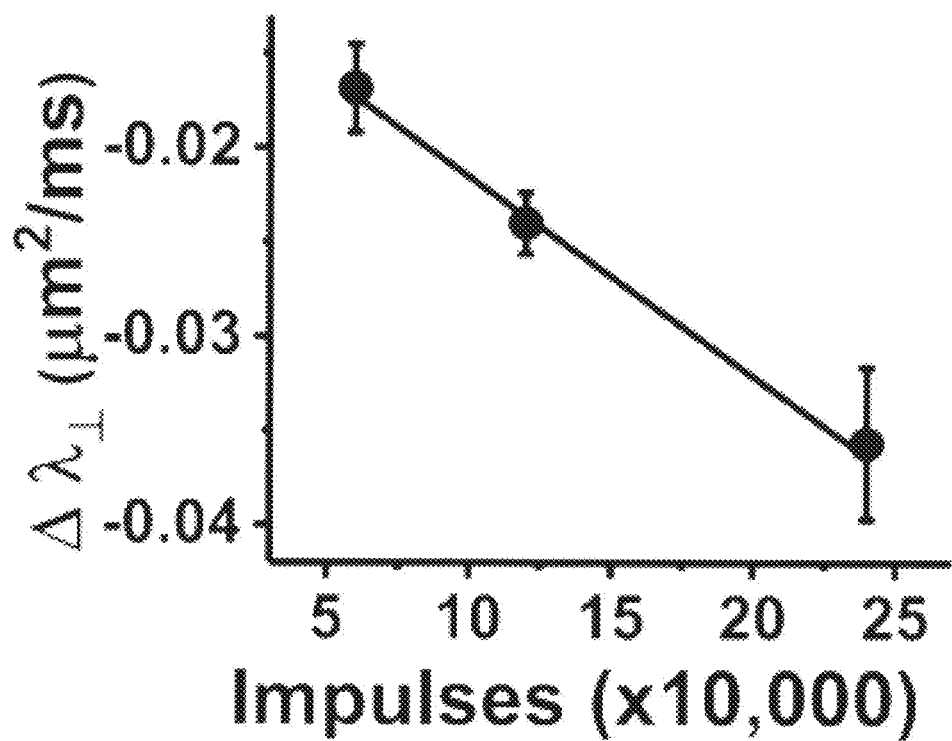
FIG. 11A is a graph of the magnitude of the diffusion fMRI response, $\Delta\lambda_\perp$ as a function of the number of electrical impulses.
Figure 11B:
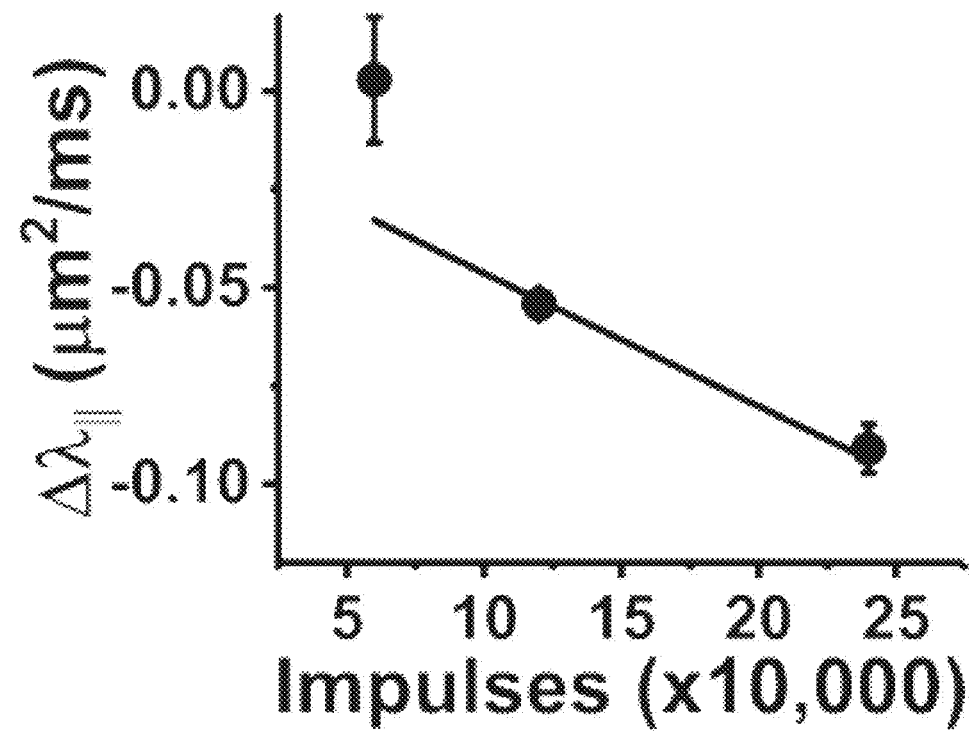
FIG. 11B is a graph of the magnitude of the diffusion fMRI response, $\Delta\lambda_\parallel$ as a function of the number of electrical impulses.

In FIG. 11A, the diffusion fMRI response in terms of the pre- to post-stimulus changes in radial diffusivity are presented for three different intensities of electrical stimulation- 50 Hz×24 min, 100 Hz×24 min, and 100 Hz×40 min. Stimuli of 50 Hz×24 min and 100 Hz×24 min were applied to the same set of nerves in series, separated by a 3-hour rest period (n=5). A separate set of nerves, described in the preceding sections, underwent the more vigorous 100 Hz×40 min stimulation regimen (n=6). The magnitude of the diffusion fMRI response, $\Delta\lambda_\perp$, increased in proportion to the number of electrical impulses carried by the nerve fibers during periods of sustained electrical activity (error bars represent SEM). The magnitude of the diffusion fMRI response appeared to be proportional to the overall electrical activity (total number of impulses carried by the nerve) during sustained repetitive stimulation. As illustrated in FIG. 11B, the axial diffusivity ($\lambda_\parallel$) exhibited a similar trend of increased magnitude during periods of sustained electrical activity.

Starting from the DTI results, the simplest interpretation, considering differences between pre-stimulus and post-stimulus values of $\lambda_\perp$ and assuming the diffusion behavior is dominated by the diffusivity of the extracellular volume fraction, would be that the bout of sustained electrical stimulus leads to swelling of the axonal fibers and shrinkage of the extracellular space. This presumed shift of water out of the extracellular space did not appear to be fully reversible within the time-frame of the current measurements. With this rationale, however, the observed dynamics of $\lambda_{\|}$ were not as obvious. Possibilities included changes of the axonal microstructure and/or differences in the free diffusivities/viscosities of intra-axonal and extracellular water. This may be understood more fully in light of the DBSI and microscopy results (see below).

In DBSI modelling, the behavior of $f_R$ suggested the formation of a transient membrane-bounded vesicular structure, induced by repetitive electrical stimulation, within the perfused frog sciatic nerve. While this phenomenon cannot be revealed by DTI modeling of the diffusion fMRI data, it may account for some of the observed decrease in $\lambda_{\|}$ from DTI.

Figure 8A:
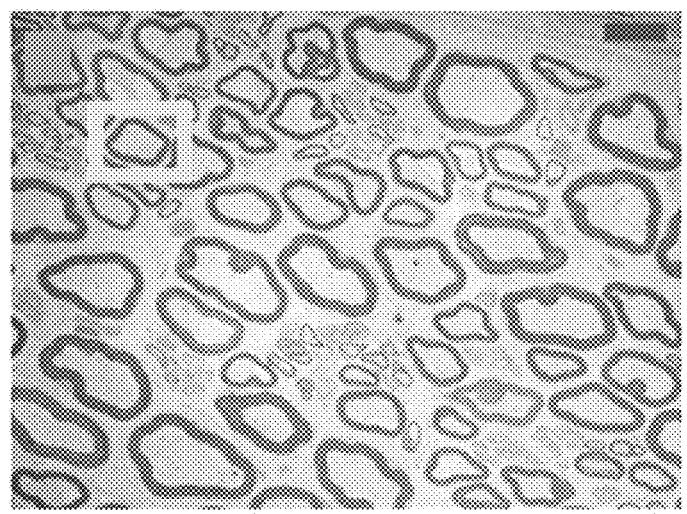
FIG. 8A is an image containing a low-magnification (600×) axial electron micrograph (EM) of a stimulation-fixed perfused frog sciatic nerve (scale bar: 10 µm)
Figure 8B:
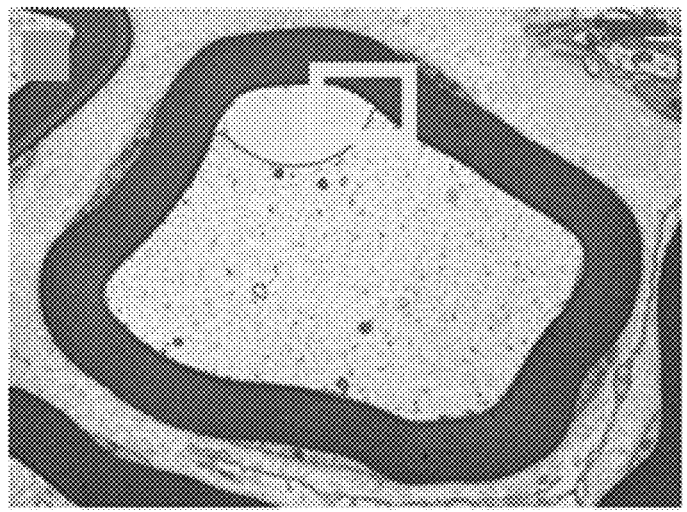
FIG. 8B is an image containing a close-up (6,000×) of the region with the yellow box superimposed on the image of FIG. 8A (Scale bar: 1 µm)

From the perspective of the dynamic $T_2$ data, considering the nature of the sub-myelinic vacuoles (FIGS. 8A, 8B, and 8C), a relatively longer $T_2$ relaxation time constant (as compared to compact myelin) would be expected for the fluid-filled sub-myelinic vacuoles observed via EM (FIGS. 8A and 8B). Thus, some unknown amount of the "axonal" water increase registered in the $T_2$ spectra, may be due to sub-myelinic vacuoles.

The results from dynamic $T_2$ spectroscopy suggested that an increase in myelin water, which was uniformly observed for the electrically-stimulated nerves, may merit future investigation as a complementary approach to non-invasively visualize rapid structural changes associated with electrical activity in white-matter or PNS. The measurements obtained in these experiments, which used non-localized CPMG echoes, were less demanding than in vivo imaging-mode implementation of dynamic myelin-water assessment. Further, the correlations between the $T_2$ axonal water fraction and DBSI restricted fraction may be challenging to study in the context of the CNS, since typically $T_2$ axonal and extracellular fractions are distinctly separated only in PNS tissue. However, application of exogenous $T_2$ relaxation agents may enable additional study of the observed correlations between the $T_2$ axonal water fraction and DBSI restricted fraction.

The diffusion fMRI results of this experiment further highlight differences between the perfused frog sciatic nerve and previously published in vivo mouse optic nerve results. For example, in the optic nerve diffusion fMRI studies, there was no observable change in the axial diffusivity with repetitive axonal activation. Further, although the mouse optic nerve the observable diffusion fMRI response in $\Delta ADC_{\perp}$ was rapidly reversible, the perfused frog sciatic nerve, $\Delta\lambda_{\perp}$ was not rapidly reversible. It is to be note, however, that the perfused sciatic nerve required vigorous electrical stimulation to achieve a smaller relative $\Delta\lambda_{\perp}$ than was seen in $\Delta ADC_{\perp}$ for the in vivo mouse optic nerve after more modest stimulation.

Further, some of these differences likely arise from the markedly different tissue geometry in the two nerves. For instance, the extracellular space in the frog sciatic nerve tissue accounts for at least 50% of the total water content of the frog sciatic nerve, based upon $T_2$ spectroscopy measurements, hence the axonal packing density is reduced in the frog PNS tissue as compared with mouse CNS. Without being limited to any particular theory, the extracellular space typically accounts for 20% of tissue volume in normal CNS. Thus, a shift of water out of the extracellular space would be expected to have a larger impact on the overall diffusion characteristics in mouse CNS. The demand for highly-interconnected neurons in CNS of higher organisms is often cited as the selective pressure that spurred the evolutionary development of dense packing and smaller gauge axons in CNS tissue. Typical mouse optic nerve axons are on the order of 1 μm in diameter and are uniformly myelinated in healthy tissue. In addition to very small unmyelinated axons, the frog PNS contains myelinated axons with a distribution of outer diameters whose upper limit is ~16 μm.

The mouse optic nerve and the frog sciatic nerve further differ with respect to the myelin itself. The larger PNS axons tend to be blanketed by very thick myelin wrapping, sometimes over 100 layers deep, whereas for the smaller axons in the CNS, fewer total layers of myelin are the rule. Additionally, the internodal spacing in mouse optic nerve is much shorter [138 μm, on average] than that in frog sciatic nerve axons [wherein, it ranges up to 1.5 mm].

The experiments described above performed using perfused frog sciatic nerves were relatively large and robust compared to corresponding CNS nerves, such as perfused mouse optic nerves. This may pose a challenge for any additional experiments performed using perfused mouse optic nerves, including in animal models of optic neuritis and/or trauma, which represent a natural next step for mechanistic exploration in mammalian CNS.

Example 3: Electron Microscopy of Activated and Deactivated Frog Sciatic Nerve

To assess the structures involved in activation and deactivation of the frog sciatic nerves visualized using DBSI and T2 spectral methods as described above, the following experiments were conducted. The frog sciatic nerves obtained as described above in Example 2 were fixed and subjected to imaging using electron microscopy as described below.

Tissue Fixation and Electron Microscopy

The fixative used for perfusion fixation contained 2% glutaraldehyde, 2 mM calcium acetate and 20 mM sodium cacodylate. After 1 hour in fixative at room temperature, the nerve-containing fixative solution was transferred to a refrigerator and stored at 4° C. for a total of 12 hours. After fixation, the nerve tissue was diced into 3-mm segments and rinsed in 0.10 M cacodylate buffer at pH 7.4 with 2 mM calcium chloride 3 times for 10 minutes each time. Samples were then subjected to a secondary fixation step for one hour in 1% osmium textroxide/1.5% potassium ferrocyanide in cacodylate buffer. Subsequently, samples were rinsed in 0.10 M maleate buffer at pH 6.0 three times for 10 minutes per rinse and en bloc stained for 1 hour with 1% uranyl acetate in maleate buffer. At the completion of staining, samples were briefly washed in ultrapure water, dehydrated in a graded acetone series (50%, 70%, 90%, 100%×2) for 10 minutes each step, infiltrated with microwave assistance (Pelco BioWave Pro, Redding, Calif.) into LX112 resin, and flat embedded in a silicone mold to orient the nerve segment for cross-sectioning. Samples were cured in an oven at 60° C. for 48 hours. Once the resin was cured, 70 nm thin sections were taken. TEM imaging was performed at 80 keV using a JEOL JEM-1400 Plus microscope (JEOL, Tokyo, Japan).

EM images of individual axons were segmented using a semi-automatic image segmentation method to define the cross-sectional area occupied by myelin, axoplasm and periaxonal vacuole for each axon. The Axon/Myelin/Vacuole segmentation method was a region or pixel-based image segmentation method that involved the selection of initial seed points. A seed pixel marker was manually placed in myelin, axon, and possibly vacuole regions (depending upon whether or not they were seen in a given image). In practice, the segmented areas of vacuole typically overlapped with axon.

The images were first pre-processed to enhance the contrast between the low intensity myelin and relatively higher intensity axonal regions, with default parameters of the built-in MATLAB® (2015b) function, imadjust. Images were then filtered to smooth the intensities as well as sharpened boundaries/edges of the axon and myelin regions. Filtering was done in the frequency domain. Smoothing the intensities was implemented using a Gaussian low pass filter (~1.3% of the width of the Fourier transform of the image) and the edges were sharpened using a Gaussian high pass filter (~0.6% of the width of the Fourier transform of the image). This preprocessing step was thought to improve segmentation and demarcate their edges from surrounding regions.

A region growing segmentation approach was then used to examine neighboring pixels of initial seed points and determine whether the pixel neighbors should be added to a region based on pixel intensity. The region growing segmentation was based on MATLAB® (2015b) built-in function grayconnected, which finds connected regions of similar intensity in the grayscale image, within a range of intensity values determined by a threshold or tolerance that can be user-controlled. The user specifies the intensity value to use as a starting point, the seed pixel, and the function grayconnected generates a binary mask image, where all of the foreground pixels are 8-connected to the seed pixel by pixels of similar intensity.

The area of the binary mask image, representing a segmented region corresponding to axon, vacuole or myelin area, was measured using the MATLAB® (2015b) built-in function region props. The diameter of each segmented region was also obtained from the area using the formula for area of an equivalent circle, $A=(\pi/4)^2$, where $A$=area of segmented region and $D$=equivalent diameter of segmented region. The measurements (area and diameter) for each axon and myelin segmented were recorded or saved into a table/spreadsheet in .csv format. Areas were reported in pixel units.

The myelin area reported in the .csv output was representative of the total area bounded by the myelin, including the enclosed axon and vacuole roi's. Conversion from image pixels to areas in $\mu m^2$ were performed offline based upon the known magnification/scale of the acquired EM images.

Statistics

Statistical tests of the electron microscopy images were performed using Statistica 13.2 (Tibco Software, Inc., Palo Alto, Calif.). The distributions of sub-myelinic vacuole radii in stimulation-fixed versus rested-fixed frog nerve axons, which followed roughly exponential distributions, were compared via the Cox-Mantel test within the Survival and Failure Time Analysis Module of Statistica.

Electron Microscopy

The two sciatic nerves of a single bullfrog were excised and assembled in separate perfusion flow cells on the benchtop. One of the nerves was stimulated for 40 min×100 Hz (as in the in-magnet diffusion fMRI studies) and perfusion-fixed immediately at the end of the stimulation period. The other nerve was rested and perfusion fixed at the same time as the stimulation-fixed nerve.

Figure 8C:
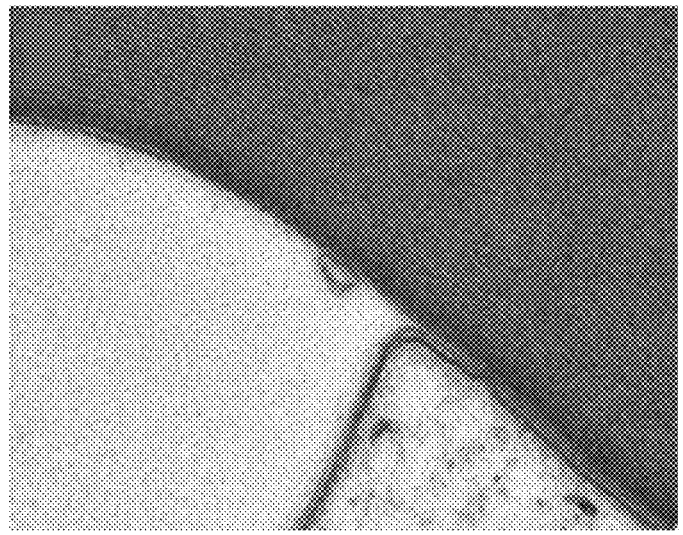
FIG. 8C is an image containing further magnification (30,000×) of the outlined region in FIG. 8B (scale bar: 200 nm)

Transverse EM images of the two sciatic nerves showed clear microstructural differences. At relatively low magnification, the myelin in both nerves was observed to be well-preserved and intact. A low-magnification image of the stimulation-fixed nerve is shown in FIG. 8A. FIGS. 8B and 8C images containing enlarged portions of the EM shown in FIG. 8A. Closer examination of the stimulation-fixed perfused frog sciatic nerve revealed the presence of numerous, fluid-filled vacuoles in the periaxonal space, and in some instances confined within the first few layers of myelin. The sub-myelinic vacuoles were observed to be larger and more prevalent than in the rest-fixed perfused frog sciatic nerve. The vacuole region shown in FIG. 8B was observed to be clear, devoid of the microtubules and positioned within the axoplasm. The 30,000×EM image of FIG. 8C illustrated a fluid-filled vacuole that had opened up between the innermost wraps of the myelin.

Figure 8D:
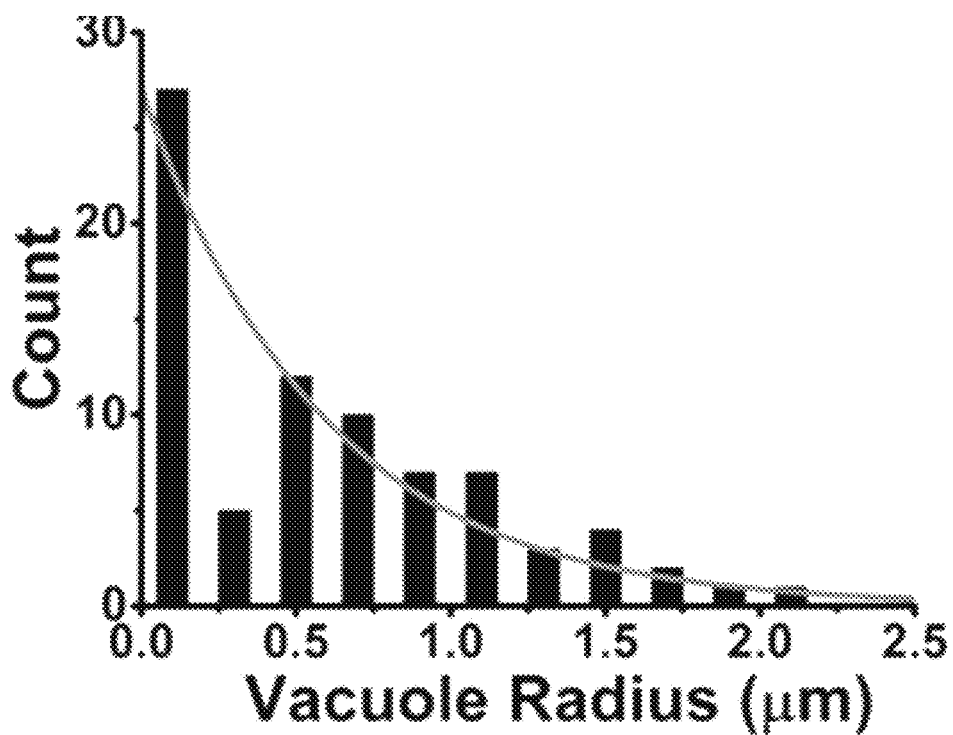
FIG. 8D is a histogram of the equivalent radius of vacuoles in sampled axons from stimulation-fixed perfused frog sciatic nerves.
Figure 8E:
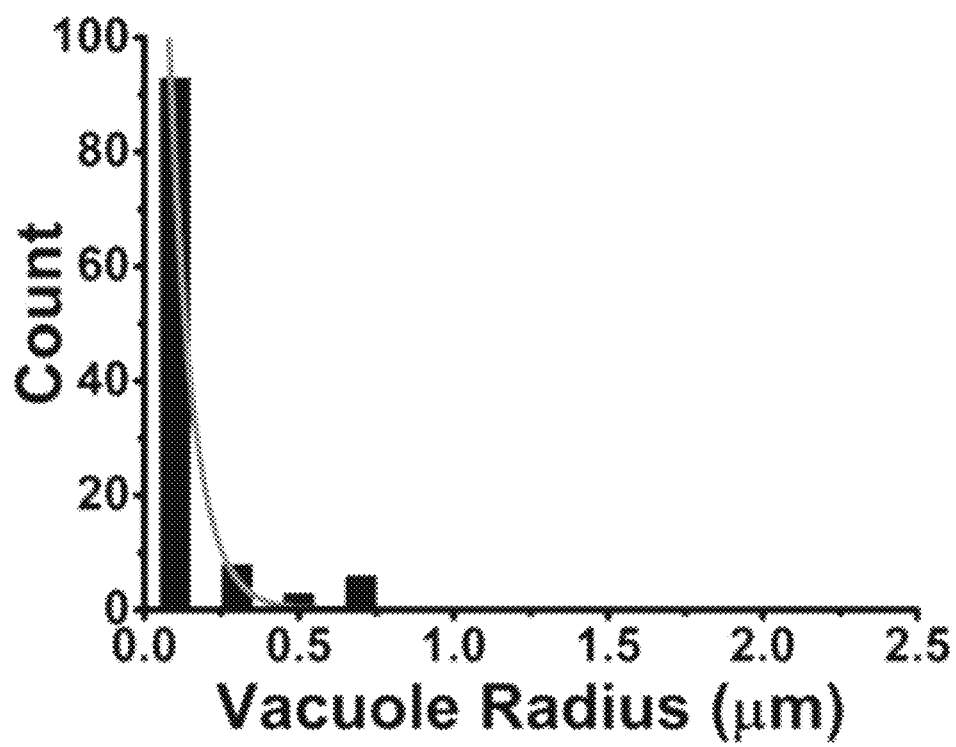
FIG. 8E is a histograms of the equivalent radius of vacuoles in sampled axons from rest-fixed perfused frog sciatic nerves.

In the stimulation-fixed axons, the sub-myelinic vacuoles were both more prevalent and larger in size than in the rest-fixed axons (FIGS. 8D and 8E). The difference between the stimulation-fixed and rest-fixed exponentially-distributed histograms was found to be highly statistically-significant via the Cox-Mantel test ($p<10^{-6}$). This observation suggested that sub-myelinic vacuoles were likely the cause of the transiently-elevated restricted component, $f_R$, observed in the DBSI time-course data.

Transient paranodal intramyelinic vacuoles induced by repetitive in situ electrical stimulation of the frog sciatic nerve have been reported previously, although previous studies have specifically focused on microstructural alterations of the paranodal myelin by examination of electron microscopy (EM) images of longitudinally-sectioned nodes of Ranvier. Without being limited to any particular theory, the spacings between nodes of Ranvier in frog sciatic nerves are known to be proportional to axonal diameter and may be as large as 1.5 mm. Thus, successfully sampling enough nodes of Ranvier via EM for statistical analysis may be exceptionally time-consuming in longitudinally-sectioned specimens.

Examining transverse-sectioned EM images of fixed frog sciatic nerves enabled more time-efficient sampling of axons. However, this sampling is not restricted to any unique axial position (nodal, paranodal, internodal, etc.). Even with the introduction of variation due to differences in axial position of various samples, the distribution of vacuole radii in the sampling of stimulation-fixed and rest-fixed axons were statistically-significantly different.

The amalgamated results from diffusion fMRI described above and electron microscopy results of this experiment suggested that sub-myelinic vacuole formation was prominent in the microstructural rearrangements that occurred with repetitive electrical activity in the frog sciatic nerve model system.

Without being limited to any particular theory, a biophysical mechanism that likely accounts for the observed microstructural changes may include localization of $K^+$ voltage-gated channels, which open up to allow egress of potassium ions from the axon during the re-polarization step of action potential conduction, to the sub-myelinic axonal membrane when the nerve is activated. In the bullfrog sciatic nerve, these $K_v$ channels are known to be distributed along the length of the internodal axonal membrane. According to this biophysical mechanism, repetitive electrical activity in myelinated axons results in an accumulation of $K^+$ and its osmotically-associated water in the confined space. The stimulation-induced sub-myelinic vacuoles observed via electron microscopy and transient post-stimulus DBSI restricted diffusion signal component supported this biophysical model for the perfused frog sciatic nerve model system.

Example 4: Electrophysiology of Activated and Deactivated Frog Sciatic Nerve Ex Vivo To assess the physiological mechanisms involved in activation and deactivation of the frog sciatic nerves visualized using DBSI and T2 spectral methods as described above, the following experiments were conducted. The CAP recordings of the frog sciatic nerves obtained as described in Ex. 2 were analyzed and correlated against T2 and diffusion MRI measurements as described below.

Electrophysiology of the Frog Sciatic Nerve

A universal observation in the perfused nerve electrophysiology experiments was that sustained, repetitive electrical stimulation produced a decrease in the compound action potential (CAP) conduction velocity during the stimulation period. In concert with the conduction velocity decrease, the CAP waveform was observed to broaden with a concomitant decrease in peak-to-peak amplitude (FIGS. 9A, 9B, and 9C).

Correlations Amongst Electrophysiology, $T_2$, and Diffusion fMRI Changes

For linear correlations amongst dynamic $T_2$ spectroscopy, diffusion fMRI, and electrophysiology measures of nerve response, $p<0.05$ was taken as the threshold for statistical significance. Repeated-measures ANOVA with Tukey post-hoc testing was used to identify the time-point at which diffusion MRI parameters differed from pre-stimulus values.

Figure 12A:
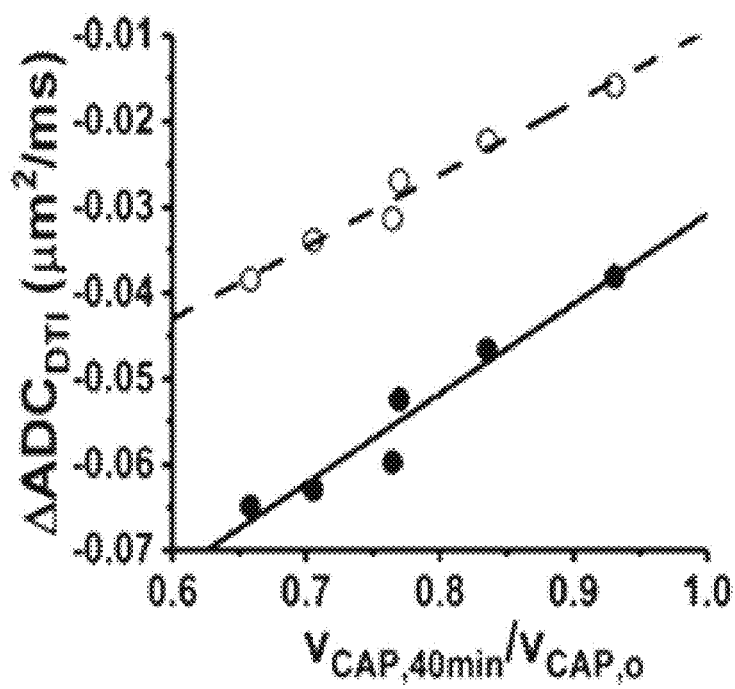
FIG. 12A is a graph showing DTI-based metrics of diffusion fMRI response $\Delta ADC_{DTI}$, with statistically-significant correlations with normalized CAP conduction velocity in the 40 min×100 Hz stimulus nerves (post-stimulation: filled circles/solid-line fits, $R^2$=0.94, p=0.0013)
Figure 12B:
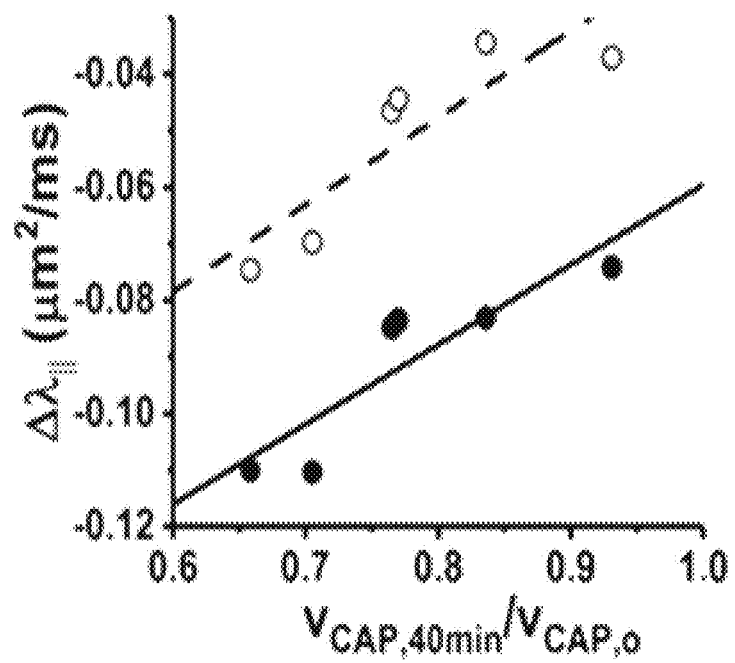
FIG. 12B is a graph showing DTI-based $\Delta\lambda_\parallel$, with statistically-significant correlations with normalized CAP conduction velocity in the 40 min×100 Hz stimulus nerves (post-stimulation: filled circles/solid-line fits, $R^2$=0.79, p=0.018)
Figure 12C:
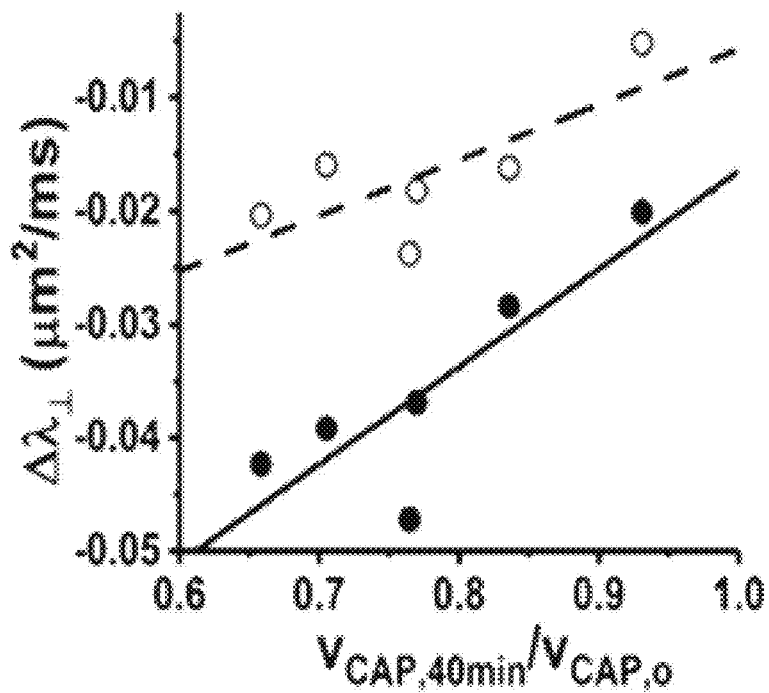
FIG. 12C is a graph showing DTI-based $\Delta\lambda_\perp$), with a statistically-significant correlation with normalized CAP conduction velocity in the 40 min×100 Hz stimulus nerves (post-stimulation: filled circles/solid-line fits, $R^2$=0.71, p=0.035)

Statistically-significant correlations were observed between the normalized axonal CAP conduction velocity measured at the end of the 40 min×100 Hz stimulation period ($v_{CAP,40\ min}/v_{CAP,0}$) and DTI-based diffusion fMRI response measures (FIGS. 12A, 12B, and 12C). Measured at the stimulus-on time-point (open circles/dashed lines), $\Delta ADC_{DTI}$ was statistically-significantly correlated with $v_{CAP},40$ min,norm ($R^2=0.97$, $p=0.0003$) (see FIG. 12A). Measured at the stimulus-on time-point (open circles/dashed lines), $\Delta\lambda_\parallel$ was statistically-significantly correlated with $v_{CAP},40$ min,norm ($R^2=0.77$, $p=0.023$) (see FIG. 12B). Measured at the stimulus-on time-point (open circles/dashed lines), $\Delta\lambda_\perp$ was not statistically-significantly correlated with $v_{CAP},40$ min,norm (see FIG. 12C). Data are shown for diffusion parameters $\Delta ADC_{DTI}$, $\Delta\lambda_\parallel$, and $\Delta\lambda_\perp$ measured during the applied stimulation time-point and at the post-stimulus time-point. From DBSI modeling of the same diffusion data, the change in the restricted isotropic diffusion component ($\Delta f_R$) did not correlate with normalized conduction velocity, but did correlate with the normalized peak-to-peak CAP amplitude (FIG. 12F). However, an increase in the DBSI restricted isotropic diffusion component did correlate with reduced CAP peak-to-peak amplitude (broadening out of the CAP waveform, $R^2=0.88$, $p=0.006$).

Figure 12D:
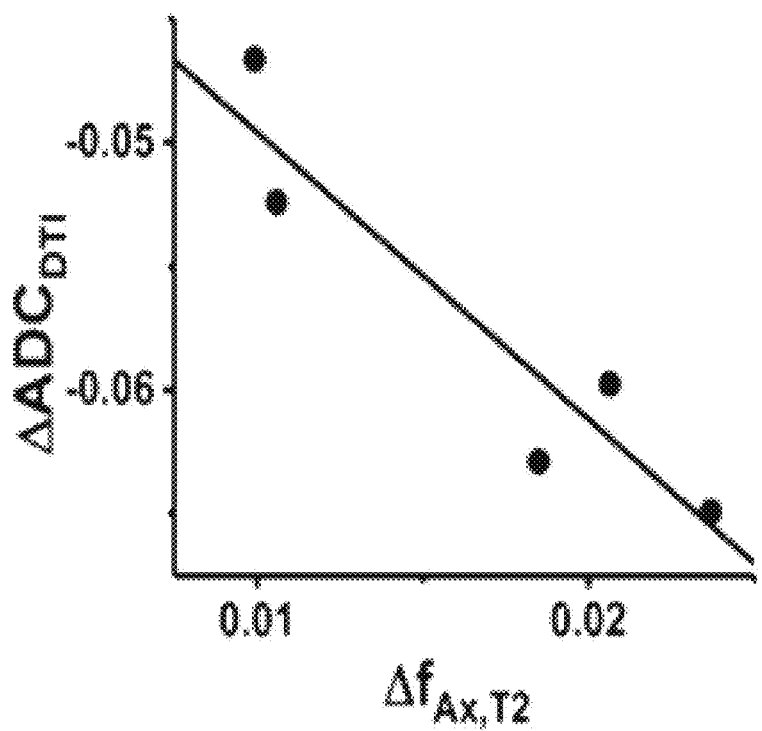
FIG. 12D is a graph showing $\Delta ADC_{DTI}$ correlated with respect to axonal water fraction in dynamic T2 spectra.
Figure 12E:
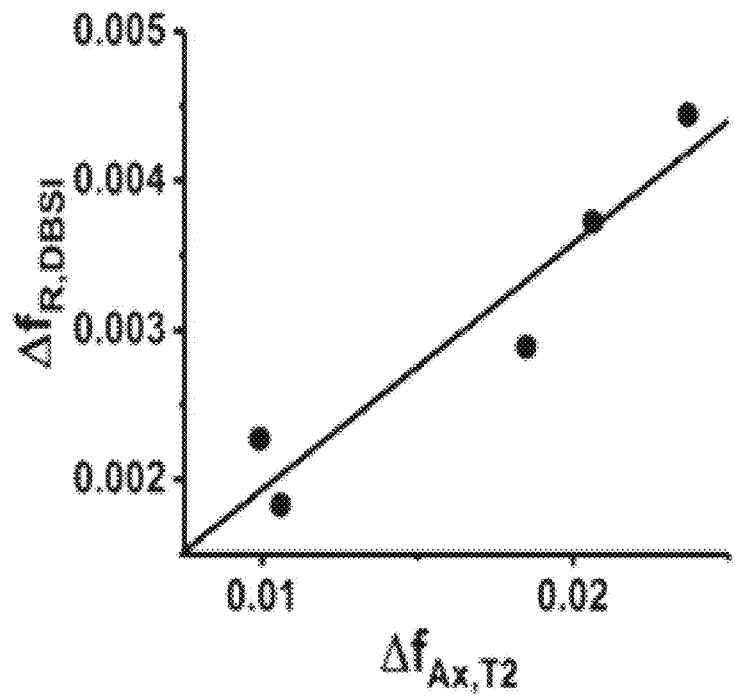
FIG. 12E is a graph showing DBSI restricted diffusion component correlated with respect to axonal water fraction in dynamic T2 spectra.
Figure 12F:
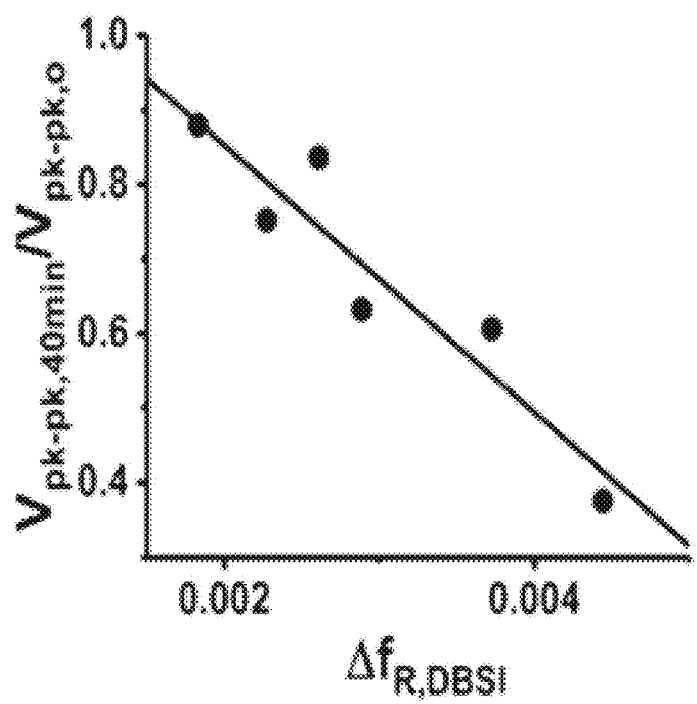
FIG. 12F is a graph showing CAP peak-to-peak amplitude correlated with respect to DBSI restricted isotropic diffusion component.

FIGS. 12D and 12E illustrated the statistically-significant correlation between dynamic $T_2$ spectroscopy and diffusion fMRI with 40-minute 100 Hz electrical stimulation. A larger shift of water into the $T_2$ axonal signal component was associated with a proportional decrease in overall ADC from DTI (FIG. 12D, $R^2=0.87$, $p=0.02$). Increasing axonal water fraction in dynamic T2 spectra is associated with an increase in the DBSI restricted diffusion component ($R^2=0.91$, $p=0.013$). A statistically-significant correlation was observed between $\Delta f_{Ax,T2}$ and the increase in DBSI restricted diffusion component, $\Delta f_R$ (FIG. 12E).

As described above, sub-myelinic vacuole formation was prominent in the microstructural rearrangements that occurred with repetitive electrical activity in the frog sciatic nerve model system. This phenomenon was consistent with observed changes in nerve electrophysiology and dynamic $T_2$ spectroscopy described above.

Without being limited to any particular theory, from a mechanistic standpoint, the electrical disturbance of the action potential (AP) wave-front charges up the next downstream node of Ranvier to its threshold potential as it propagates down a given axon. As each node of Ranvier reaches threshold potential, sodium voltage-gated channels node open, depolarizing the axon and sustaining the AP propagation. The physical parameters that dictate τ, the exponential time-constant describing the charging at a node of Ranvier, are $r_i$ (the longitudinal ohmic resistance to current flow in the axoplasm) and $c_n$ (the nodal membrane capacitance), such that $\tau=r_i \cdot c_n$.

Without being limited to any particular theory, the CAP waveforms observed in these experiments are summations of action potentials arising from the entire ensemble of conducting axons within the nerve, with the larger-gauge axons conducting more rapidly than the finer-gauge axons. As a result, a proportional decrease in action potential conduction velocity across the ensemble of axons accounts for the broadening of the CAP waveform.

Without being limited to any particular theory, the ballooning sub-myelinic vacuoles of the activated sciatic nerve, observed via EM (FIGS. 3A, 3B, and 3C) and suggested by the transient positive $\Delta f_R$ from DBSI (FIG. 7C), may exert enough mechanical force on the myelin sheath to subtly retract the paranodal myelin. If this were the case, this myelin retraction may increase the nodal membrane capacitance, $c_n$ and consequently increase the nodal charging time-constant, thus slowing down conduction of the AP at each node of Ranvier encountered by the propagating AP disturbance. This interpretation is consistent with previous published observations that the potassium channel-blocker, 4-aminopyridine (4-AP), is able to access $K_c$ channels that are normally sequestered underneath the paranodal myelin in perfused mouse sciatic nerves subjected to repetitive electrical stimulation (15 min×200 Hz). It has been previously observed that in unstimulated nerves, 4-AP does not have access to these normally-concealed $K_v$ channels.

Example 5: DBSI Detection of Axonal Conduction Blockage

To demonstrate the visualization of axonal conduction blockage using the DBSI and T2 spectrum methods described above the following experiments were conducted.

Figure 13A:
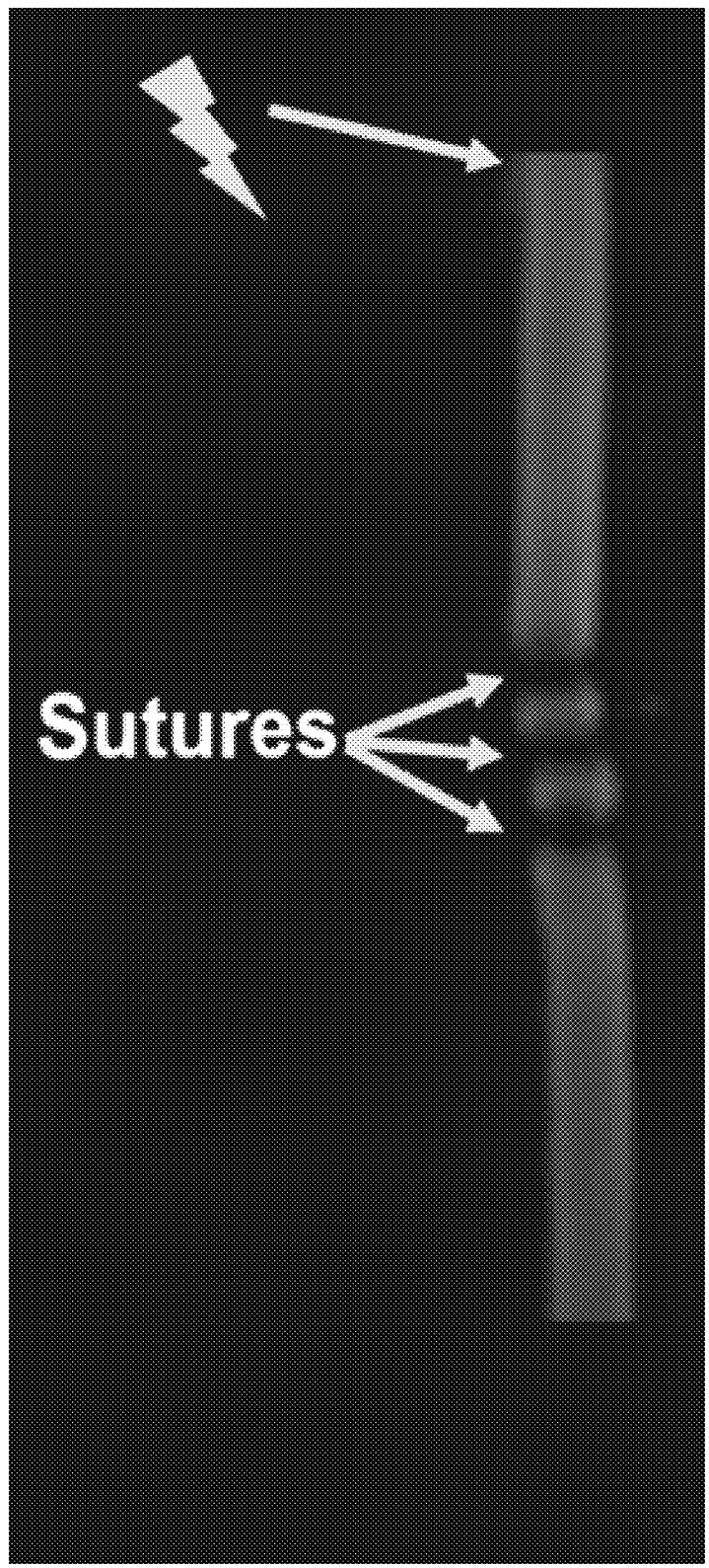
FIG. 13A is a T2-weighted MRI image of a perfused nerve that was tied off in the middle by three silk sutures and stimulation applied via suction electrode at the proximal end, as indicated, for a period of 60 minutes at 100 Hz frequency.

A perfused frog sciatic nerve tied off in the center with three sutures (FIG. 13A) was prepared using methods similar to those described in Ex. 2. The ligation of the nerve served as a surrogate model for a WM lesion or nerve crush, as might be encountered in various clinical situations.

Figure 13B:
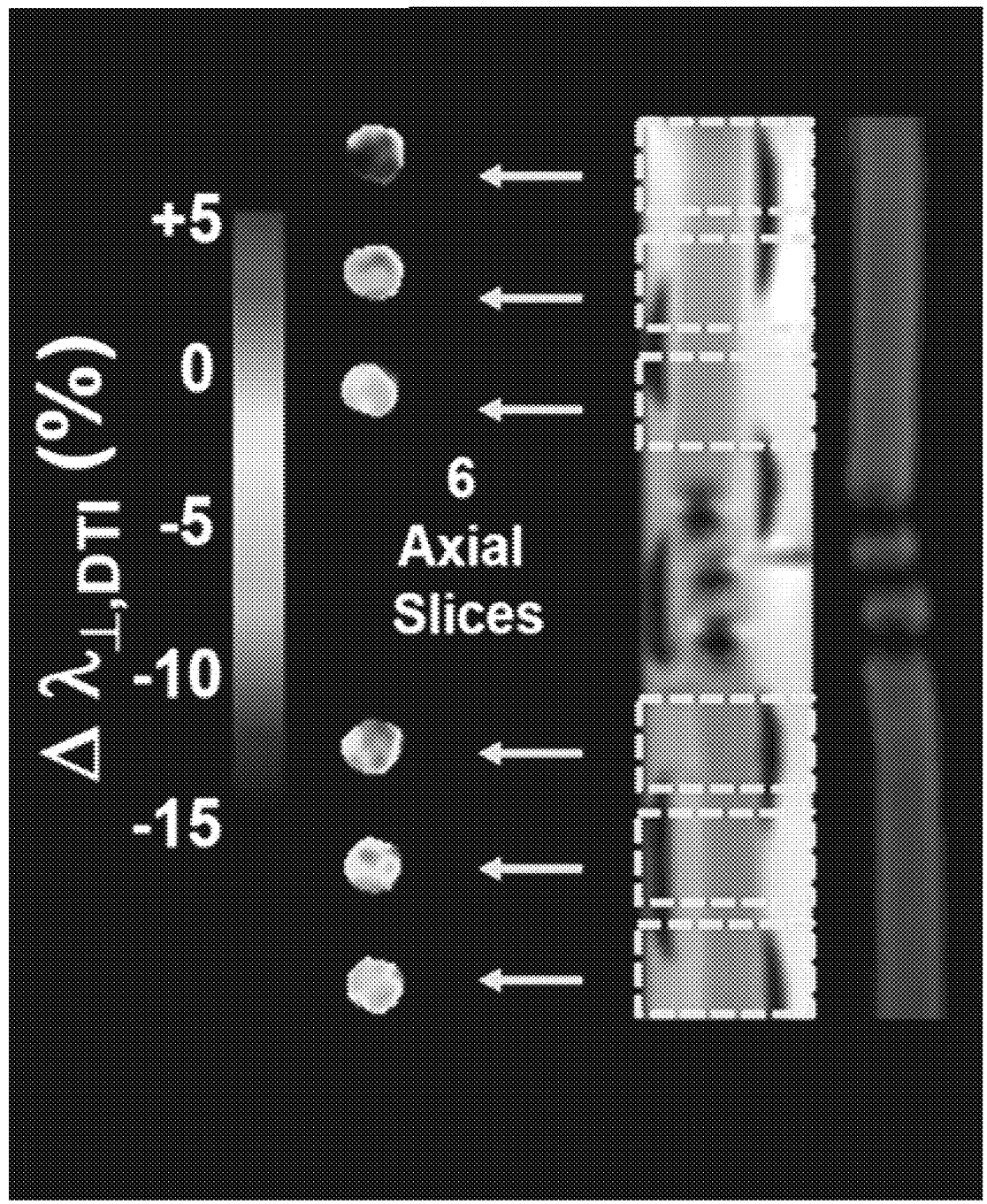
FIG. 13B is an image showing maps of the percent change in $\Delta\lambda_\perp$ pre- to post-stimulation obtained from DTI analysis of the 25-direction diffusion imaging data acquired in six axial image slices shown in FIG. 13C.
Figure 13C:
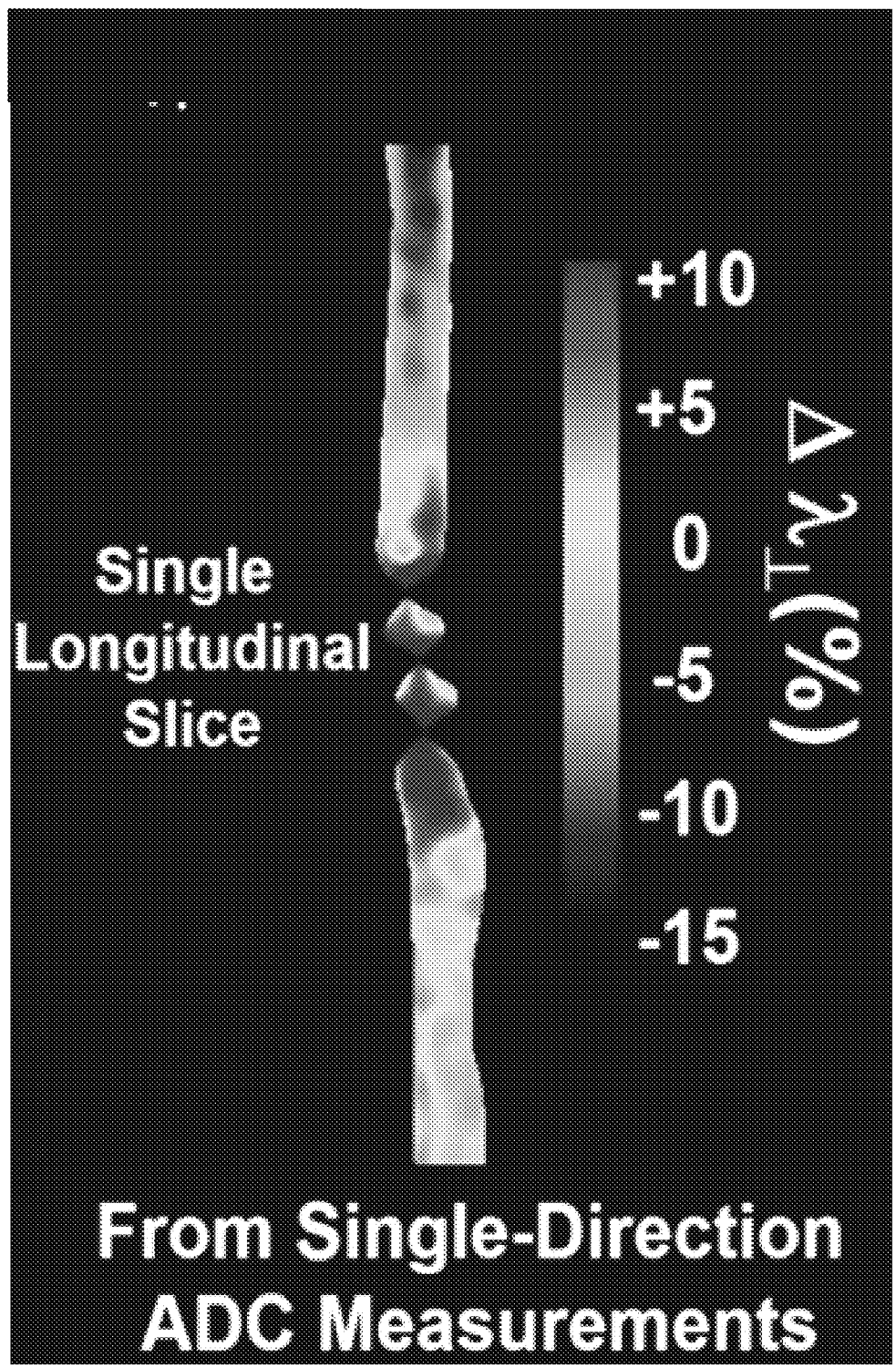
FIG. 13C is an image showing two diffusion-weighted longitudinal slice images along the length of the nerve with diffusion-encoding gradients applied orthogonal to the axonal fibers with b values of 0.15 ms/µm² and 1.5 ms/µm².
Figure 13D:
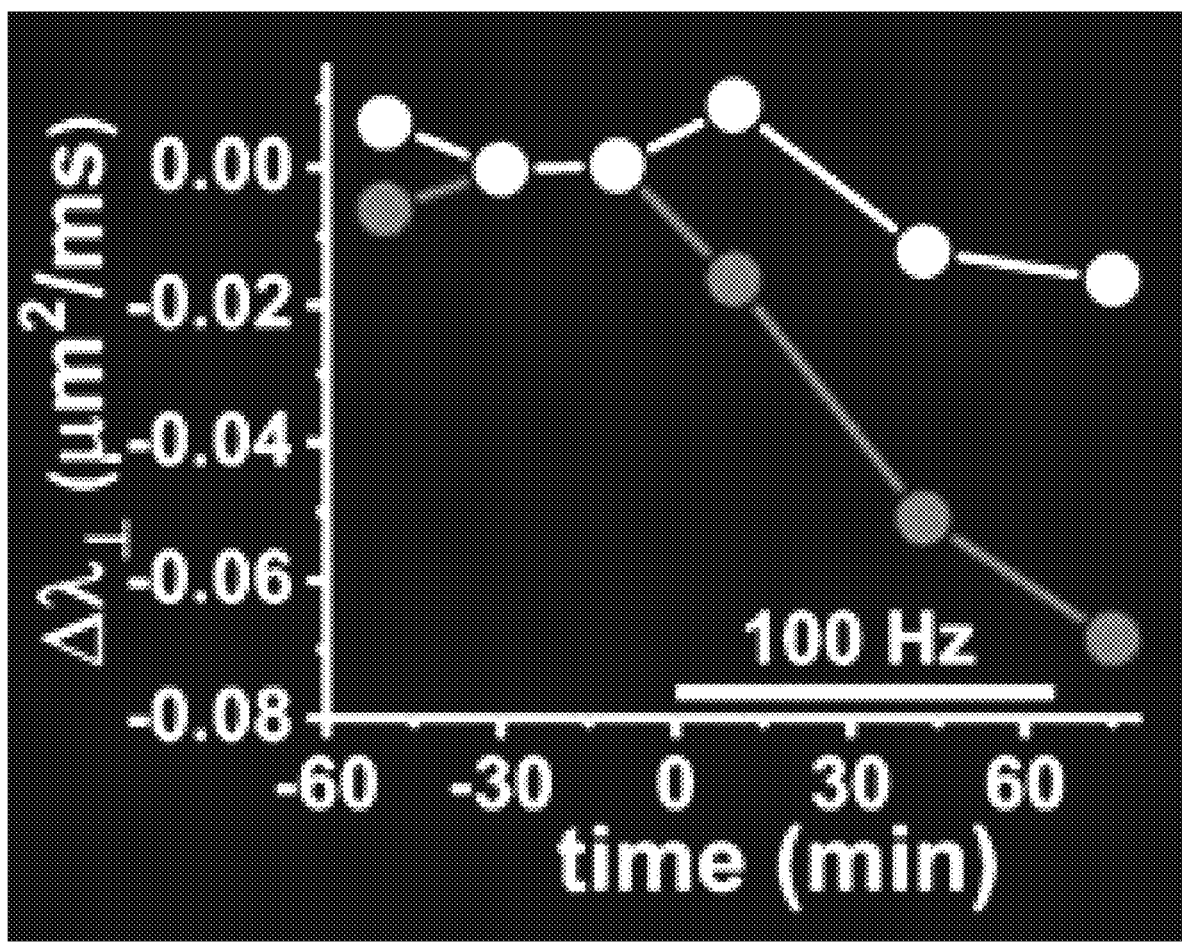
FIG. 13D is an image showing the diffusion fMRI response $\Delta\lambda_\perp$ (% change) from pre-stimulus and post-stimulus single-direction $\lambda_\perp$ maps.

Two types of diffusion MR images of the perfused nerve were acquired before and after applying electrical stimulation to the proximal end of the nerve (100 Hz×60 min). One image set consisted of six axial slices through the nerve (3 proximal to the conduction blockage and 3 distal to the sutures/conduction blockage, FIG. 13C) acquired with 25-direction diffusion weighting; these two diffusion-weighted images were used to generate maps of $\lambda_\perp$ from this single-diffusion-direction measurement. In FIG. 13B, the slice-by-slice differences (post- vs. pre-stimulation) in $\lambda_\perp$ are shown. FIG. 13D illustrates the resulting $\Delta\lambda_\perp$ in a single longitudinal slice through the nerve with diffusion weighting applied in a single direction (perpendicular to the axonal fibers). Both types of images showed the same trend. At the proximal end, the expected drop in $\lambda_\perp$ was observed, while at the distal end the $\Delta\lambda_\perp$ response was muted. Also observed, most clearly in the longitudinal-slice diffusion fMRI data (FIG. 13D), was that the region of attenuated functional response extended several millimeters proximal to the first nerve ligation.

Example 6: DBSI Detection of Optic Neuropathies

To demonstrate the diagnosis of an optic neuropathy using the DBSI methods described above, the following experiments were conducted.

Axon damage is frequently seen in optic neuropathies such as glaucoma and optic neuritis (ON). Glaucoma is a group of optic neuropathies characterized by progressive degeneration of retinal ganglion cells (RGCs) and their axons and is the leading cause of irreversible blindness worldwide. Although pathogenesis of glaucoma remains incompletely understood, optic nerve axon injury appears to play a crucial role in RGC axon and cell body degeneration. Optic neuritis is an autoimmune optic neuropathy, frequently the presenting feature of multiple sclerosis (MS). Although inflammatory demyelination is the hallmark pathology of ON, the axonal and neuronal injury has been widely observed. Despite differing etiologies, axonal injury in the optic nerves of both glaucoma and ON patients could potentially advance and cause neuronal damage. With the simultaneous and noninvasive assessment of optic nerve pathology and function afforded by the DBSI methods described above, an enhanced understanding of the underlying pathophysiology in glaucoma and ON may lead to the improved patient care and a surrogate end point for future clinical trials.

Figure 14:
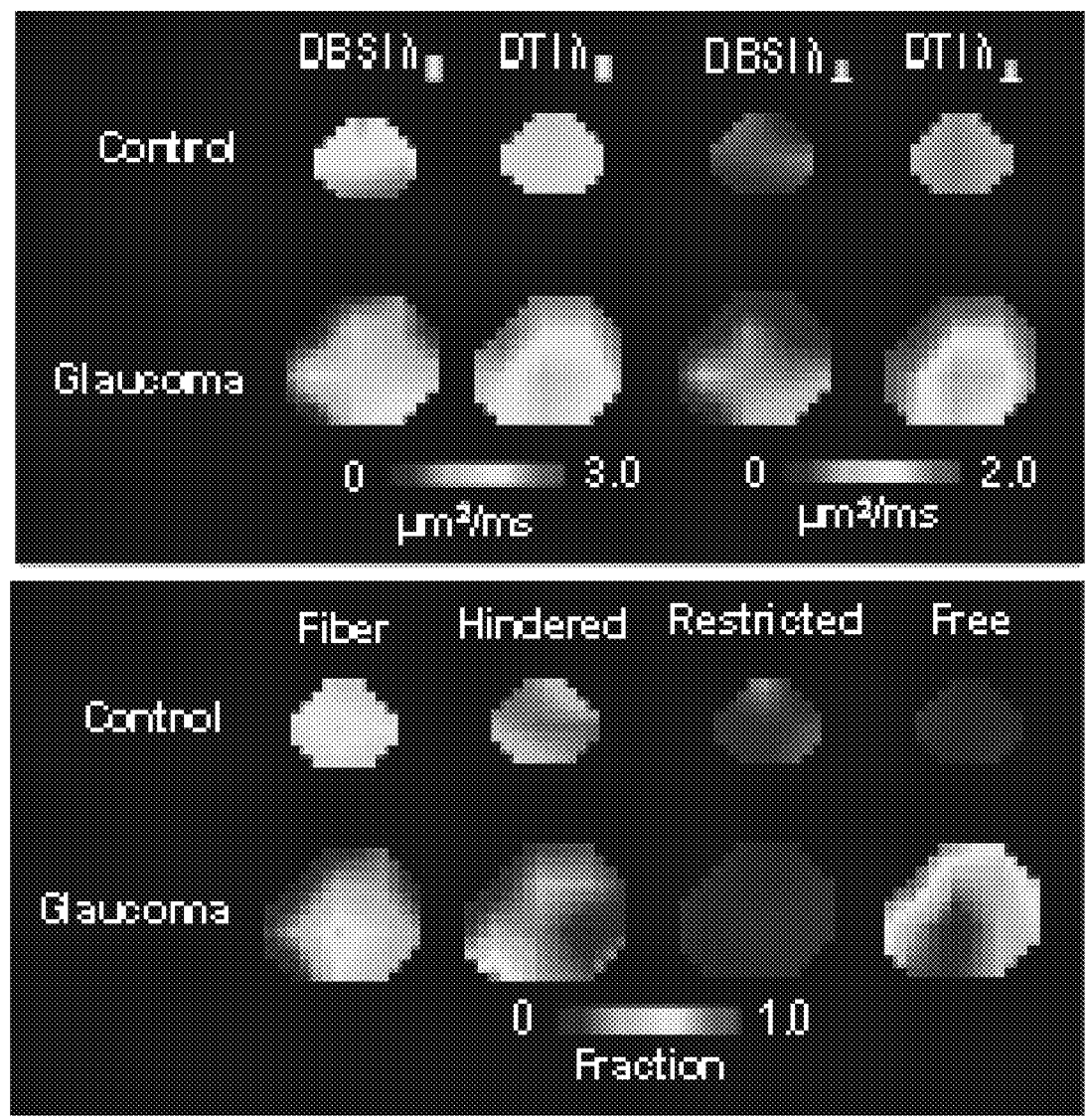
FIG. 14 contains a series of diffusion MRI pathological metric maps derived from modified DBSI comparing the DBSI metrics of healthy (CTL) subjects and subjects with glaucoma (Glaucoma)
Figure 15A:
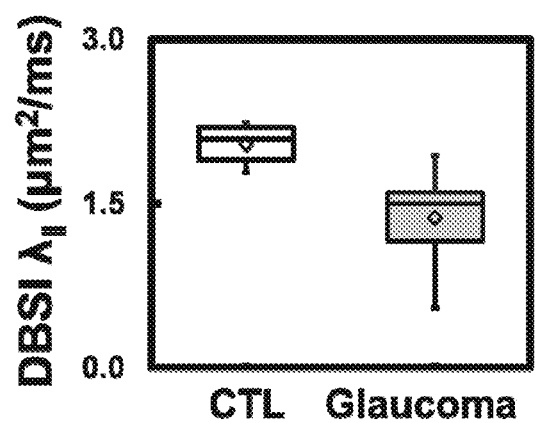
FIG. 15A is a bar graph comparing a mean DBSI-$\lambda_\parallel$ for healthy (CTL) subjects and subjects with glaucoma (Glaucoma)
Figure 15B:
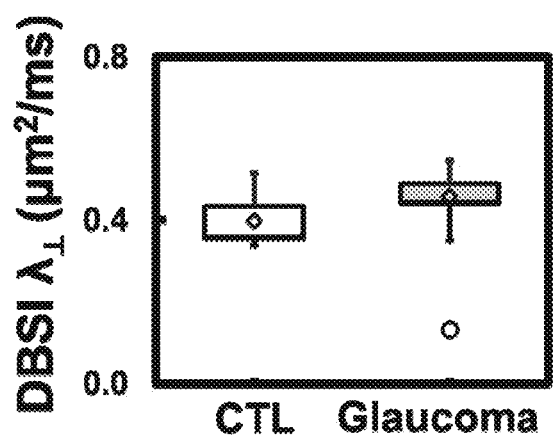
FIG. 15B is a bar graph comparing a mean DBSI-$\lambda_\perp$ for healthy (CTL) subjects and subjects with glaucoma (Glaucoma)
Figure 15C:
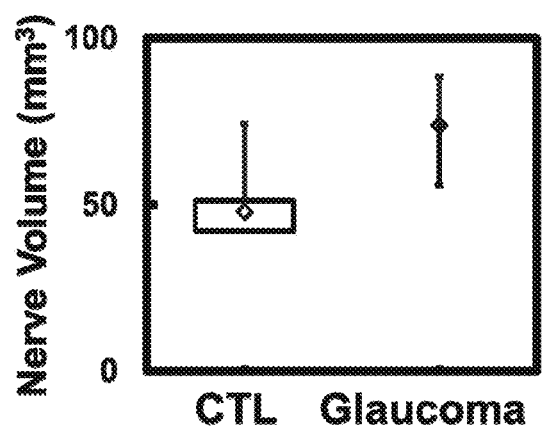
FIG. 15C is a bar graph comparing a mean DBSI-derived nerve volume for healthy (CTL) subjects and subjects with glaucoma (Glaucoma)
Figure 15D:
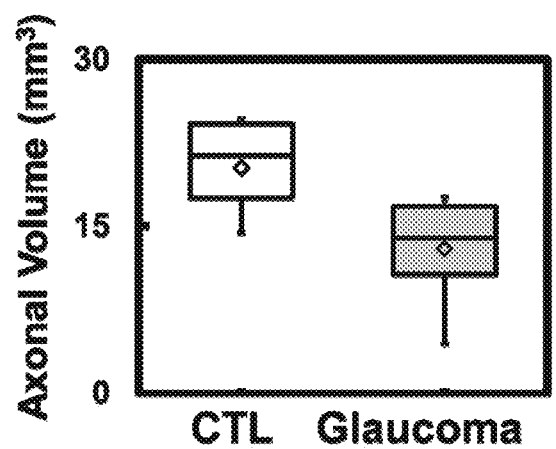
FIG. 15D is a bar graph comparing a mean DBSI-derived axonal volume for healthy (CTL) subjects and subjects with glaucoma (Glaucoma)

Four glaucoma patients (1 male, 3 female, ages ranging 58-76) were subjected to DBSI assessment of optic nerves using the DBSI methods described above. Among the glaucoma patient population, two patients were low tension glaucoma and two patients were primary open angle glaucoma. FIG. 14 is a comparison of DBSI-derived pathological metric maps for a representative control subject and a subject from the glaucoma population. Preliminary results indicate that both DBSI-$\lambda_\parallel$ and DBSI-$\lambda_\perp$ correlated with OCT-RNFL thickness while either DTI-$\lambda_\parallel$ or DTI-$\lambda_\perp$ correlated with OCT-RNFL thickness, reveal optic nerve pathology in a representative glaucoma patients. Optic nerve swelling was apparent in the glaucoma patients. The DBSI-derived pathological metrics illustrated in FIG. 14 demonstrated coexisting axonal injury, demyelination, and inflammation.

FIGS. 15A, 15B, 15C, and 15D summarize a quantitative assessment of the mean DBSI-derived pathological metric values from the four glaucoma patients as compared with the 7 healthy control subjects. This assessment revealed that the glaucoma patients exhibited axonal injury characterized by decreased DBSI-$\lambda_\parallel$ (see FIG. 15A), demyelination characterized by increased DBSI-$\lambda_\perp$ (see FIG. 15B), and axonal loss characterized by decreased axonal volume (see FIG. 15D) in the presence of nerve swelling characterized by increased nerve volume (see FIG. 15C).

Example 7: Comparison of DTI and DBSI Detection of Frog Sciatic Nerve Activation and Deactivation Ex Vivo To compare the effectiveness of the DBSI and DTI analysis models for the detection of nerve activation and deactivation using of fMRI, the following experiments were conducted.

A cross-validation (CV) of the DTI and DBSI model fits of the data was carried out on data from two pre-stimulus MRI measurements previously analyzed in Example 2 ((the second and third time points in FIGS. 6A-6C and 7B-7H) for a 3×3 voxel region of interest (ROI) placed at the center of the nerve. These points were chosen because the diffusion signal was not evolving in time, as was the case post-stimulation. The DBSI and DTI models were used to analyze the first pre-stimulus MR measurement and to predict the signal intensities of the second pre-stimulus MR measurements.

Figure 23A:
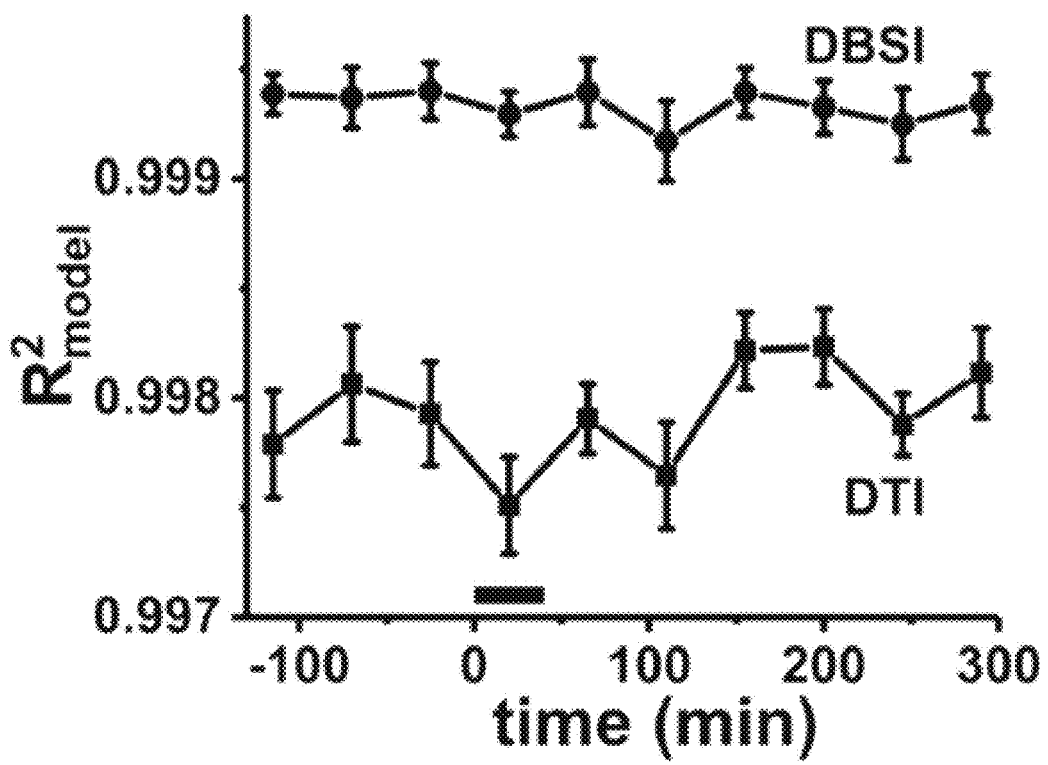
FIG. 23A is a graph comparing $R^2$ for fitting of data vs. model across a time-series for six nerves undergoing 40 min×100 Hz stimulation (closed circles=DBSI model, closed squares=DTI model, applied stimulus indicated by the horizontal black bar)

FIG. 23A compares the $R^2$ for fitting of data vs. model across the time-series for the six nerves undergoing 40 min×100 Hz stimulation for the DBSI model (closed circles) and for the DTI model (closed squares). As illustrated in FIG. 23A, the reproducibility of MR signal intensity in repeat measurements was high ($R^2$ repeat=0.99933±0.00009, mean±SD).

Figure 23B:
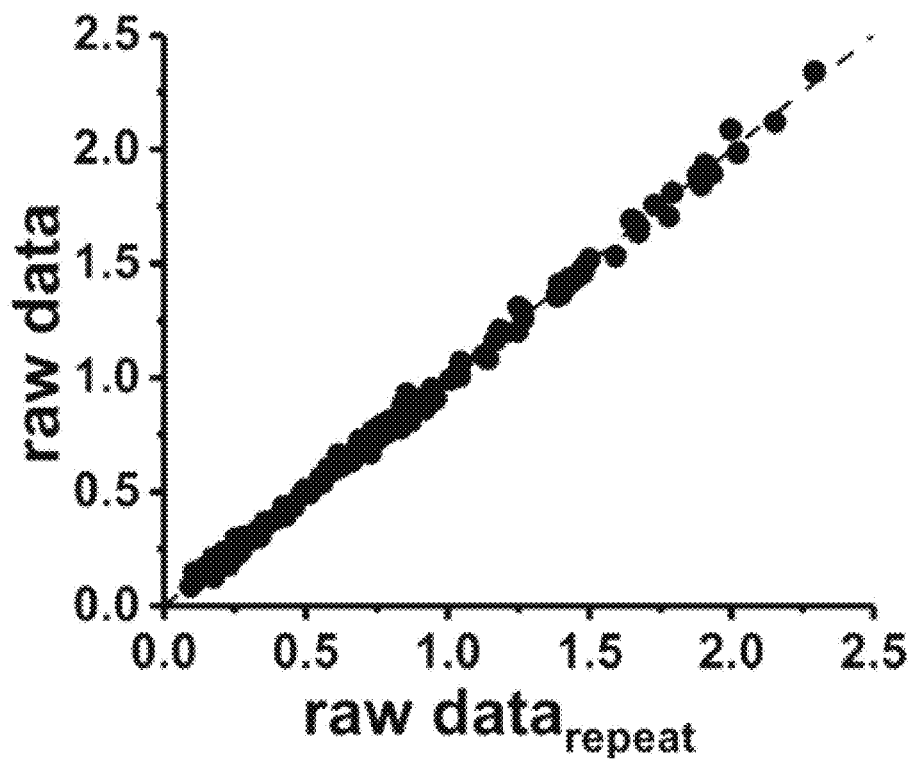
FIG. 23B is a graph summarizing the signal intensity of a repeat pre-stimulus MRI measurement as a function of the signal intensity of an initial first pre-stimulus MRI measurement (line of identity (y=x) is plotted as a dashed line)
Figure 23C:
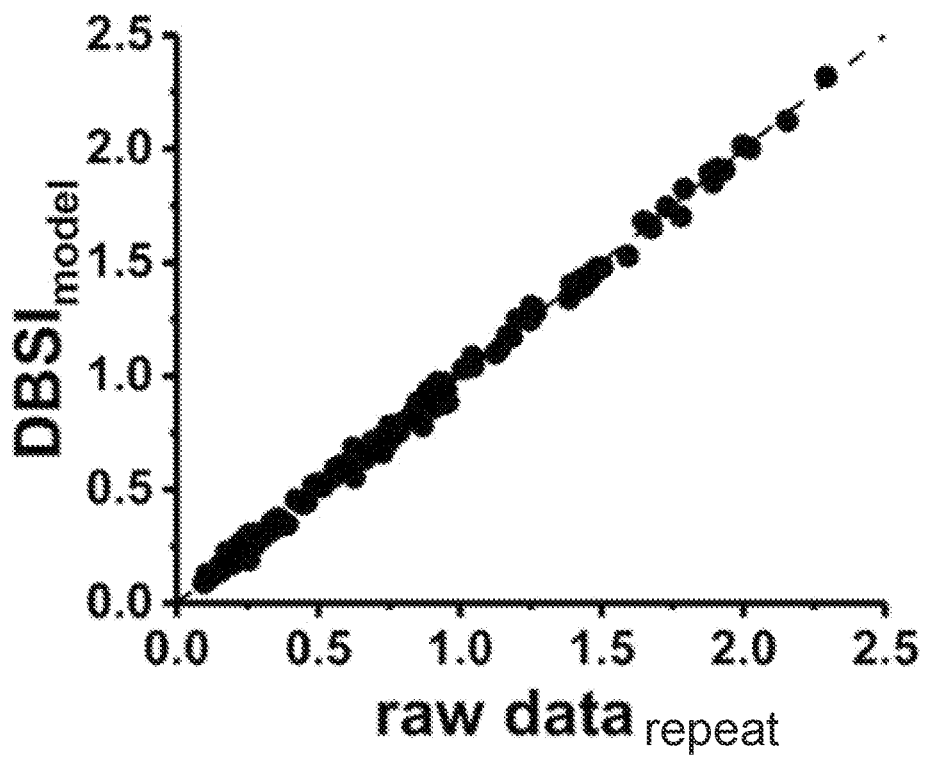
FIG. 23C is a graph summarizing the DBSI-predicted signal intensity of a repeat pre-stimulus MRI measurement as a function of the signal intensity of the initial first pre-stimulus MRI measurement from FIG. 23B (line of identity (y=x) is plotted as a dashed line)
Figure 23D:
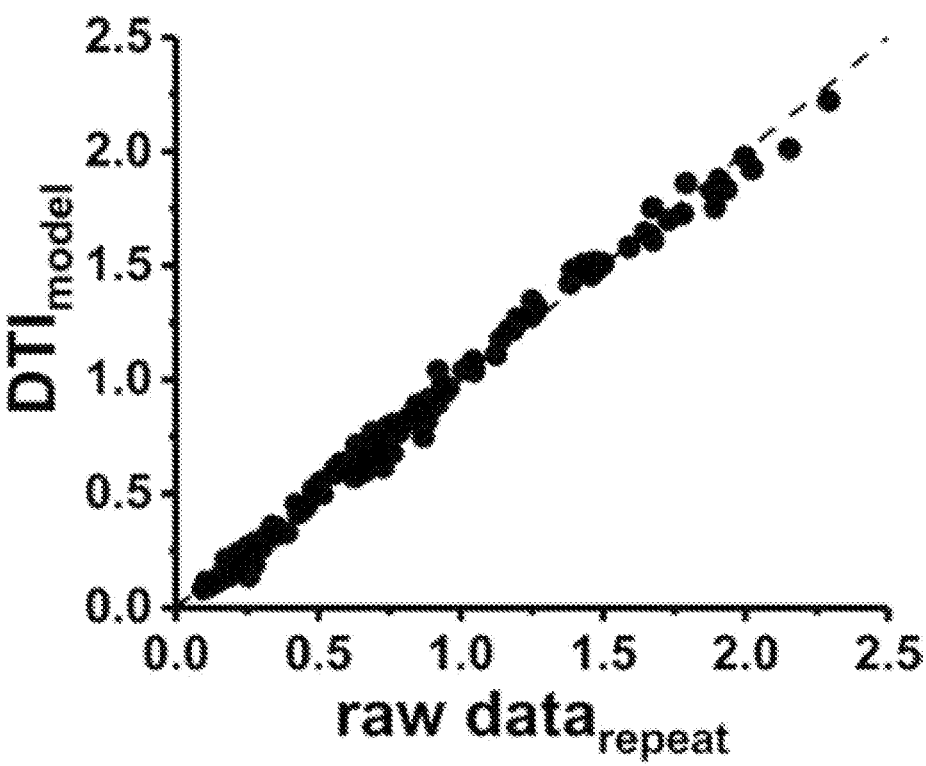
FIG. 23D is a graph summarizing the DTI-predicted signal intensity of a repeat pre-stimulus MRI measurement as a function of the signal intensity of the initial first pre-stimulus MRI measurement from FIG. 23B (line of identity (y=x) is plotted as a dashed line)

Signal intensities (in scanner signal intensity units) of each of the 25 different diffusion weightings/directions from each of the six nerves were compared and analyzed using the DBSI and DTI models. For each data point in FIGS. 23B-23D, the x coordinate corresponds to the intensity measured in the second baseline (pre-stimulus) MRI measurement and the y coordinate corresponds to the intensity measured in the subsequent repeat pre-stimulus baseline measurement (FIG. 23B), the signal intensity predicted by the DBSI model (FIG. 23C), and the signal intensity predicted by the DTI model (FIG. 23D). The line of identity (y=x) is plotted as a dashed line in FIGS. 23B-23D.

FIG. 23A demonstrates that data Reproducibility in repeat measurements was very high due to high SNR and absence of bulk physiological motion. As illustrated in FIG. 23B, the DBSI-predicted MR signal intensities were comparable to the measurement reproducibility ($R^2$ CV, DBSI=0.99926±0.00044, mean±SD). In four of the six cases analyzed in this experiment, the DBSI model made a better prediction of the repeat measure data than when the first dataset was used to predict signal intensities in the second dataset. For all time points across the serial measurements, the DBSI model of the multi-direction/multi-b-value diffusion data provided excellent fits to the data ($R^2 \geq 0.99859$). As shown FIG. 23D, the DTI model, with fewer parameters, did not fit the MR signal data as well as the DBSI model, nor did DTI perform as well as DBSI in the CV assessment described above. Across the time series of measurements the DTI model produces very high-quality fits to the data ($0.99696 \leq R^2 \leq 0.99868$).

Example 8: Assessment of Human Optic Nerve Function Using Diffusion Basis Spectrum Imaging (DBSI)

To compare the effectiveness of the DBSI and DTI analysis models for the detection of optic nerve function non-invasively in human subjects, the following experiments were conducted. DTI and diffusion basis spectrum imaging (DBSI) were used to assess human optic nerve activation during exposure to a flashing checkerboard stimulation.

Previously, single-direction diffusion-weighted MRI of optic nerves in mice demonstrated that the mouse optic nerves exhibited decreased apparent diffusion coefficient perpendicular to axonal fibers ($ADC_\perp$) during flashing-light stimulation. Unlike blood-oxygen level dependent (BOLD) fMRI, the activation induced $ADC_\perp$ decrease was independent of alterations in blood flow and more directly associated with axonal activation. In a subsequent study, we observed that the decrease in $ADC_\perp$ was attenuated in optic nerves affected by optic neuritis in mice.[2] We speculate this is due, in part, to the presence of inflammation confounding $ADC_\perp$ measurements which may have masked the effects of actual axonal activation.

We claim the following:

1. A computer-implemented method of detecting nerve activity from a time series of diffusion MRI images, the method comprising:

obtaining, using an MRI scanner, a time-series of diffusion MRI datasets from a nerve including diffusion functional MRI datasets obtained while the nerve is under stimulation during at least part of acquisition of the diffusion functional MRI datasets, each diffusion MRI dataset comprising a plurality of voxels and associated diffusion MRI signals, wherein the stimulation includes task-specific stimulation;

applying, using a computing device, a diffusion basis spectrum imaging (DBSI) model to each diffusion MRI dataset of the time-series to obtain a time-series of at least one DBSI parameter;

detecting, using the computing device, the nerve activity in response to the stimulation at each voxel of the plurality of voxels based on changes in at least one value within the time series of the at least one DBSI parameter according to a nerve activity detection rule;

transforming, using the computing device, the detected nerve activity into a spatial map of nerve activity at each voxel position of the diffusion MRI dataset; and displaying to a user, using a display device operatively coupled to the computing device, the spatial map of nerve activity.

2. The method of claim 1, wherein the nerve activity detection rule further comprises detecting a nerve activity in response to the stimulation for at least one of:

an increase of a fiber component ($f_{fiber}$) value above a first threshold value;

an increase of a restricted component ($f_R$) value above a second threshold value;

a decrease of an axial diffusivity ($\lambda_\parallel$) value below a third threshold value;

a decrease of a radial diffusivity ($\lambda_\perp$) value below a fourth threshold value;

a decrease of a hindered isotropic spectral component ($D_H$) value below a fifth threshold value; or an increase of a restricted isotropic spectral component ($D_R$) value above a sixth threshold value.

3. The method of claim 2, wherein:

the first threshold value is 1% of a total diffusion signal higher than a baseline $f_{fiber}$ value associated with a non-stimulated nerve;

the second threshold value is 0.3% of the total diffusion signal higher than a baseline $f_R$ value associated with a non-stimulated nerve;

the third threshold value is 0.06 $\mu m^2$/ms less than a baseline $\lambda_\parallel$ value associated with a non-stimulated nerve;

the fourth threshold value is 0.02 $\mu m^2$/ms less than a baseline $\lambda_\perp$ value associated with a non-stimulated nerve;

the fifth threshold value is 0.1 $\mu m^2$/ms less than a baseline $D_H$ value associated with a non-stimulated nerve; and the sixth threshold value is 0.03 $\mu m^2$/ms less than a baseline $D_R$ value associated with a non-stimulated nerve.

4. The method of claim 2, further comprising estimating, using the computing device, an intensity of nerve activation based on changes in at least one value within the time series of the at least one DBSI parameter according to a nerve activity intensity rule.

5. The method of claim 4, wherein the nerve activity intensity rule comprises an empirically-derived relationship between a change in the axial diffusivity ($\lambda_\parallel$) value and a nerve activity intensity, wherein further increases of axial diffusivity ($\lambda_\perp$) value below the third threshold value are indicative of increased nerve activity intensity.

6. A computer-implemented method of detecting optic nerve activity in a human subject from a time series of diffusion MRI images, the method comprising:

obtaining, using an MRI scanner, a time-series of diffusion MRI datasets from an optic nerve including diffusion functional MRI datasets obtained while the optic nerve is under stimulation during at least part of acquisition of the diffusion functional MRI datasets, each diffusion MRI dataset comprising a plurality of voxels and associated diffusion MRI signals, wherein the stimulation includes task-specific stimulation;

applying, using a computing device, a diffusion basis spectrum imaging (DBSI) model to each diffusion MRI dataset of the time-series to obtain a time-series of at least one DBSI parameter;

detecting, using the computing device, the nerve activity in response to the stimulation at each voxel of the plurality of voxels based on changes in at least one value within the time series of the at least one DBSI parameter according to a nerve activity detection rule;

transforming, using the computing device, the detected nerve activity into a spatial map of nerve activity at each voxel position of the diffusion MRI dataset; and displaying to a user, using a display device operatively coupled to the computing device, the spatial map of nerve activity.

7. The method of claim 6, wherein the nerve activity detection rule further comprises detecting a nerve activity for at least one of:

a decrease of an axial diffusivity ($\Delta_\parallel$) value below a third threshold value; and a decrease of a radial diffusivity ($\lambda_\perp$) value below a fourth threshold value.

8. The method of claim 7, wherein:

the third threshold value is 0.2 $\mu m^2$/ms less than a baseline $\lambda_\parallel$ value associated with a non-stimulated nerve; and the fourth threshold value is 0.3 $\mu m^2$/ms less than a baseline $\lambda_\perp$ value associated with a non-stimulated nerve.

9. A computer-implemented method of detecting optic nerve pathology in a human subject from a time series of diffusion MRI images, the method comprising:

obtaining, using an MRI scanner, a diffusion MRI dataset from an optic nerve including diffusion functional MRI datasets obtained while the optic nerve is under stimulation during at least part of acquisition of the diffusion functional MRI datasets, the diffusion MRI dataset comprising a plurality of voxels and associated diffusion MRI signals, wherein the stimulation includes task-specific stimulation;

applying, using a computing device, a diffusion basis spectrum imaging (DBSI) model to the diffusion MRI dataset to obtain at least one DBSI parameter;

detecting, using the computing device, the optic nerve pathology on nerve function in response to the simulation at each voxel of the plurality of voxels based on at least one value of the at least one DBSI parameter according to an optic nerve pathology detection rule;

transforming, using the computing device, the detected optic nerve pathology into a spatial map of optic nerve pathology at each voxel position of the diffusion MRI dataset; and displaying to a user, using a display device operatively coupled to the computing device, the spatial map of optic nerve pathology.

10. The method of claim 9, wherein the optic nerve pathology detection rule further comprises detecting an optic nerve pathology for at least one of:

a decrease of an axial diffusivity ($\lambda_\parallel$) value below a third threshold value; and an increase of a radial diffusivity ($\lambda_\perp$) value above a fourth threshold value.

11. The method of claim 10, wherein:

the third threshold value is 0.5 $\mu m^2/ms$ less than a baseline $\lambda_\parallel$ value associated with a non-stimulated nerve; and the fourth threshold value is 0.1 $\mu m^2/ms$ greater than a baseline $\lambda_\perp$ value associated with a non-stimulated nerve.

* * * * *